US012655466B2

(12) United States Patent
Gagrat et al.

(10) Patent No.: US 12,655,466 B2
(45) Date of Patent: Jun. 16, 2026

(54) STRUCTURE AND TEMPERATURE-DEPENDENT FLAP ENDONUCLEASE SUBSTRATES

(71) Applicant: Exact Sciences Corporation, Madision, WI (US)

(72) Inventors: Zubin Gagrat, Madison, WI (US); Michael B. Matter, Madison, WI (US); Nicholas J. Domanico, Madison, WI (US); Michael J. Domanico, Madison, WI (US)

(73) Assignee: Exact Sciences Corporation, Madison, WI (US)

( * ) Notice: Subject to any disclaimer, the term of this patent is extended or adjusted under 35 U.S.C. 154(b) by 1042 days.

(21) Appl. No.: 17/760,709

(22) PCT Filed: Sep. 16, 2020

(86) PCT No.: PCT/US2020/051118
§ 371 (c)(1),
(2) Date: Mar. 15, 2022

(87) PCT Pub. No.: WO2021/055508
PCT Pub. Date: Mar. 25, 2021

(65) Prior Publication Data
US 2023/0046033 A1 Feb. 16, 2023

Related U.S. Application Data

(60) Provisional application No. 62/901,085, filed on Sep. 16, 2019.

(51) Int. Cl.
*C12Q 1/6818* (2018.01)
*C12Q 1/686* (2018.01)
*C12Q 1/6876* (2018.01)

(52) U.S. Cl.
CPC ........... *C12Q 1/6818* (2013.01); *C12Q 1/686* (2013.01); *C12Q 1/6876* (2013.01)

(58) Field of Classification Search
CPC ............... C12Q 1/6818; C12Q 1/6876; C12Q 2525/301; C12Q 2561/109
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |

(Continued)

FOREIGN PATENT DOCUMENTS

| | | |
|---|---|---|
| WO | WO 92/002258 | 2/1992 |
| WO | WO 93/10820 | 6/1993 |

(Continued)

OTHER PUBLICATIONS

Olivier, Michael, "The Invader® assay for SNP genotyping," Mutation Research, vol. 573, pp. 103-110. (Year: 2005).*

(Continued)

*Primary Examiner* — Young J Kim
(74) *Attorney, Agent, or Firm* — Casimir Jones, S.C.; Mary Ann D. Brow

(57) ABSTRACT

5' hairpin oligonucleotide substrates for reversible repression, e.g., by temperature shift, of cleavage by flap endonucleases, and methods using 5' hairpin oligonucleotides.

12 Claims, 38 Drawing Sheets
Specification includes a Sequence Listing.

5′ Hairpin

Released Flap

C6/3′-

BELOW REACTION TEMP. → CLEAVAGE REPRESSED

(56) References Cited

U.S. PATENT DOCUMENTS

| | | | |
|---|---|---|---|
| 4,965,188 | A | 10/1990 | Mullis et al. |
| 5,011,769 | A | 4/1991 | Duck et al. |
| 5,124,246 | A | 6/1992 | Urdea et al. |
| 5,288,609 | A | 2/1994 | Engelhardt et al. |
| 5,338,671 | A | 8/1994 | Scalice et al. |
| 5,403,711 | A | 4/1995 | Walder et al. |
| 5,409,818 | A | 4/1995 | Davey et al. |
| 5,432,272 | A | 7/1995 | Benner |
| 5,494,810 | A | 2/1996 | Barany et al. |
| 5,508,169 | A | 4/1996 | Deugau et al. |
| 5,624,802 | A | 4/1997 | Urdea et al. |
| 5,639,611 | A | 6/1997 | Wallace et al. |
| 5,660,988 | A | 8/1997 | Duck et al. |
| 5,710,264 | A | 1/1998 | Urdea et al. |
| 5,773,258 | A | 6/1998 | Birch et al. |
| 5,792,614 | A | 8/1998 | Western et al. |
| 5,846,717 | A | 12/1998 | Brow et al. |
| 5,849,481 | A | 12/1998 | Urdea et al. |
| 5,851,770 | A | 12/1998 | Babon et al. |
| 5,882,867 | A | 3/1999 | Ullman et al. |
| 5,914,230 | A | 6/1999 | Liu et al. |
| 5,958,692 | A | 9/1999 | Cotton et al. |
| 5,965,408 | A | 10/1999 | Short |
| 5,985,557 | A | 11/1999 | Prudent et al. |
| 5,994,069 | A | 11/1999 | Hall et al. |
| 6,001,567 | A | 12/1999 | Brow et al. |
| 6,001,983 | A | 12/1999 | Benner |
| 6,013,170 | A | 1/2000 | Meade |
| 6,063,573 | A | 5/2000 | Kayyem |
| 6,090,543 | A | 7/2000 | Prudent et al. |
| 6,110,677 | A | 8/2000 | Western et al. |
| 6,110,684 | A | 8/2000 | Kemper et al. |
| 6,121,001 | A | 9/2000 | Western et al. |
| 6,150,097 | A | 11/2000 | Tyagi et al. |
| 6,150,510 | A | 11/2000 | Seela et al. |
| 6,183,960 | B1 | 2/2001 | Lizardi |
| 6,210,884 | B1 | 4/2001 | Lizardi |
| 6,221,583 | B1 | 4/2001 | Kayyem et al. |
| 6,235,502 | B1 | 5/2001 | Weissman et al. |
| 6,248,229 | B1 | 6/2001 | Meade |
| 6,329,178 | B1 | 12/2001 | Patel et al. |
| 6,395,524 | B2 | 5/2002 | Loeb et al. |
| 6,399,397 | B1 | 6/2002 | Zarling et al. |
| 6,562,611 | B1 | 5/2003 | Kaiser et al. |
| 6,602,695 | B2 | 8/2003 | Patel et al. |
| 6,872,816 | B1 | 3/2005 | Hall et al. |
| 7,122,364 | B1 | 10/2006 | Lyamichev et al. |
| 7,482,118 | B2 | 1/2009 | Allawi et al. |
| 7,662,594 | B2 | 2/2010 | Kong et al. |
| 8,361,720 | B2 | 1/2013 | Oldham-Haltom et al. |
| 8,445,238 | B2 | 5/2013 | Hall et al. |
| 8,715,937 | B2 | 5/2014 | Zou et al. |
| 8,916,344 | B2 | 12/2014 | Zou et al. |
| 9,000,146 | B2 | 4/2015 | Bruinsma et al. |
| 9,096,893 | B2 | 8/2015 | Allawi et al. |
| 9,212,392 | B2 | 12/2015 | Allawi et al. |
| 10,648,025 | B2 | 5/2020 | Allawi et al. |
| 10,704,081 | B2 | 7/2020 | Lidgard et al. |
| 11,299,766 | B2 | 4/2022 | Lidgard et al. |
| 2006/0147955 | A1 | 7/2006 | Allawi et al. |
| 2006/0183207 | A1 | 8/2006 | Lyamichev et al. |
| 2007/0048748 | A1 | 3/2007 | Williams et al. |
| 2007/0202525 | A1 | 8/2007 | Quake et al. |
| 2008/0293045 | A1 | 11/2008 | Piepenburg et al. |
| 2009/0253142 | A1 | 10/2009 | Allawi et al. |
| 2018/0073064 | A1 | 3/2018 | Kozlov et al. |
| 2019/0177769 | A1* | 6/2019 | Allawi ............... C12Q 1/6827 |

FOREIGN PATENT DOCUMENTS

| | | |
|---|---|---|
| WO | WO 94/22892 | 10/1994 |
| WO | WO 94/24144 | 10/1994 |
| WO | WO 02/070755 | 9/2002 |
| WO | WO 05/023091 | 3/2005 |
| WO | WO 2006/122208 | 11/2006 |
| WO | WO 2011/008530 | 1/2011 |
| WO | WO 2014/160117 | 10/2014 |
| WO | WO 2015/021460 | 2/2015 |
| WO | WO 2015/066695 | 5/2015 |
| WO | WO 2017/075061 | 4/2017 |
| WO | WO 2020/112869 | 6/2020 |

OTHER PUBLICATIONS

Liu et al., "Controllable extension of hairpin-structured flaps to allow low-background cascade invasive reaction for a sensitive DNA logic sensor for mutation detection," Chem. Sci., December, vol. 9, pp. 1666-1673. (Year: 2017).*

Liu et al., Supplemental Information, Chem. Sci., December, pp. 1-20. (Year: 2017).*

International Search Report and Written Opinion for PCT/US2020/051118. Mailed Dec. 29, 2020. 16 pages.

International Preliminary Report on Patentability for PCT/US2020/051118. Mailed Mar. 31, 2020. 9 pages.

Allawi et al., Invader plus method detects herpes simplex virus in cerebrospinal fluid and simultaneously differentiates types 1 and 2. J Clin Microbiol. Sep. 2006;44(9):3443-7.

Allawi et al., Modeling of flap endonuclease interactions with DNA substrate. J Mol Biol. May 2, 2003;328(3):537-54.

Antao et al., A thermodynamic study of unusually stable RNA and DNA hairpins. Nucl. Acids Res. 1991. 19; 21: 5901-5905.

Ballabio et al., Screening for steroid sulfatase (STS) gene deletions by multiplex DNA amplification. Hum Genet. May 1990;84(6):571-3.

Barany. Genetic disease detection and DNA amplification using cloned thermostable ligase. Proc Natl Acad Sci U S A. Jan. 1, 1991;88(1):189-93.

Bustin. Absolute quantification of mRNA using real-time reverse transcription polymerase chain reaction assays. J Mol Endocrinol. Oct. 2000;25(2):169-93.

Ceska et al., Structure-specific DNA cleavage by 5' nucleases. Trends Biochem Sci. Sep. 1998;23(9):331-6.

Chamberlain et al., Deletion screening of the Duchenne muscular dystrophy locus via multiplex DNA amplification. Nucleic Acids Res. Dec. 9, 1988;16(23):11141-56.

Chapados et al., Structural basis for FEN-1 substrate specificity and PCNA-mediated activation in DNA replication and repair. Cell. Jan. 9, 2004;116(1):39-50.

Corstjens et al., Infrared up-converting phosphors for bioassays. IEE Proc Nanobiotechnol. Apr. 2005;152(2):64-72.

Don et al., 'Touchdown' PCR to circumvent spurious priming during gene amplification. Nucleic Acids Res. Jul. 25, 1991;19(14):4008.

Dorjsuren et al., Complementary non-radioactive assays for investigation of human flap endonuclease 1 activity. Nucleic Acids Res. Jan. 2011;39(2):e11. 11 pages.

FASMAN. Practical Handbook of Biochemistry and Molecular Biology. CRC Press, Boca Raton. 1989, pp. 385-394.

Finger et al., The wonders of flap endonucleases: structure, function, mechanism and regulation. Subcell Biochem. 2012;62:301-26.

Guilfoyle et al., Ligation-mediated PCR amplification of specific fragments from a class-II restriction endonuclease total digest. Nucleic Acids Res. May 1, 1997;25(9):1854-8.

Hall et al., Sensitive detection of DNA polymorphisms by the serial invasive signal amplification reaction. Proc Natl Acad Sci U S A. Jul. 18, 2000;97(15):8272-7.

Hayden et al., Multiplex-Ready Pcr: A new method for multiplexed SSR and SNP genotyping. BMC Genomics. 2008; 9:80. 1-12.

Hecker et al., High and low annealing temperatures increase both specificity and yield in touchdown and stepdown PCR. Biotechniques. Mar. 1996;20(3):478-85.

Herman et al., Methylation-specific PCR: a novel PCR assay for methylation status of CpG islands. Proc Natl Acad Sci U S A. Sep. 3, 1996;93(18):9821-6.

Higuchi et al., A general method of in vitro preparation and specific mutagenesis of DNA fragments: study of protein and DNA interactions. Nucleic Acids Res. Aug. 11, 1988;16(15):7351-67.

(56) References Cited

OTHER PUBLICATIONS

Higuchi et al., Kinetic PCR analysis: real-time monitoring of DNA amplification reactions. Biotechnology (N Y). Sep. 1993;11(9):1026-30.

Higuchi et al., Simultaneous Amplification and Detection of Specific DNA Sequences. Bio/TechnoLogy, 1992; 10(4), 413-417.

Hirao et al., Most compact hairpin-turn structure exerted by a short DNA fragment, d(GCGAAGC) in solution: an extraordinarily stable structure resistant to nucleases and heat. Nucleic Acids Res. Feb. 25, 1994;22(4):576-82.

Hyone-Myong Eun, Enzymology Primer for Recombinant DNA Technology, Academic Press, 1996. TOC only. 6 pages.

Kaiser et al., A comparison of eubacterial and archaeal structure-specific 5'-exonucleases. J Biol Chem. Jul. 23, 1999;274(30):21387-94.

Kalinina et al., Nanoliter scale PCR with TaqMan detection. Nucleic Acids Res. May 15, 1997;25(10):1999-2004.

Lin et al., Synthesis and duplex stability of oligonucleotides containing cytosine-thymine analogues. Nucleic Acids Res. Dec. 25, 1989;17(24):10373-83.

Lin et al., Synthesis of oligodeoxyribonucleotides containing degenerate bases and their use as primers in the polymerase chain reaction. Nucleic Acids Res. Oct. 11, 1992;20(19):5149-52.

Liu et al., Flap endonuclease 1: a central component of DNA metabolism. Annu Rev Biochem. 2004;73:589-615.

Lyamichev et al., Comparison of the 5' nuclease activities of taq DNA polymerase and its isolated nuclease domain. Proc Natl Acad Sci USA. May 25, 1999;96(11):6143-8.

Lyamichev et al., Experimental and theoretical analysis of the invasive signal amplification reaction. Biochemistry. Aug. 8, 2000;39(31):9523-32.

Lyamichev et al., Polymorphism identification and quantitative detection of genomic DNA by invasive cleavage of oligonucleotide probes. Nat Biotechnol. Mar. 1999;17(3):292-6.

Olivier et al., The Invader assay for SNP genotyping. Mutat Res. Jun. 3, 2005;573(1-2):103-10.

Orpana. Fluorescence resonance energy transfer (FRET) using ssDNA binding fluorescent dye. Biomol Eng. Apr. 2004;21(2):45-50.

Ostermayer. Preparation and properties of infrared-to-visible conversion phosphors. Metall. Trans. 1971; 2(3): 747-755.

Patel et al., Flap endonucleases pass 5'-flaps through a flexible arch using a disorder-thread-order mechanism to confer specificity for free 5'-ends. Nucleic Acids Res. May 2012;40(10):4507-19.

Roux et al., Using mismatched primer-template pairs in touchdown PCR. Biotechniques. May 1994;16(5):812-4.

Schouten et al., Relative quantification of 40 nucleic acid sequences by multiplex ligation-dependent probe amplification. Nucleic Acids Res. Jun. 15, 2002;30(12):e57. 13 pages.

Schweitzer et al., Aromatic Nonpolar Nucleosides as Hydrophobic Isosteres of Pyrimidine and Purine Nucleosides. J Org Chem. Dec. 1, 1994;59(24):7238-7242.

Schweitzer et al., Hydrophobic, Non-Hydrogen-Bonding Bases and Base Pairs in DNA. J Am Chem Soc. Feb. 22, 1995;117(7):1863-1872.

Selvin. Fluorescence resonance energy transfer. Methods Enzymol. 1995;246:300-34.

Shen et al., Multiple but dissectible functions of FEN-1 nucleases in nucleic acid processing, genome stability and diseases. Bioessays. Jul. 2005;27(7):717-29.

Stryer. Fluorescence energy transfer as a spectroscopic ruler. Annu Rev Biochem. 1978;47:819-46.

Triglia et al., A procedure for in vitro amplification of DNA segments that lie outside the boundaries of known sequences. Nucleic Acids Res. Aug. 25, 1988;16(16):8186.

Tsutakawa et al., Human flap endonuclease structures, DNA double-base flipping, and a unified understanding of the FEN1 superfamily. Cell. Apr. 15, 2011;145(2):198-211.

Tumey et al., The identification and optimization of a N-hydroxy urea series of flap endonuclease 1 inhibitors. Bioorg Med Chem Lett. Jan. 17, 2005;15(2):277-81.

Van De Rijke et al., Up-converting phosphor reporters for nucleic acid microarrays. Nat Biotechnol. Mar. 2001;19(3):273-6.

Vogelstein et al., Digital PCR. Proc Natl Acad Sci U S A. Aug. 3, 1999;96(16):9236-41.

Liu et al., Controllable extension of hairpin-structured flaps to allow low-background cascade invasive reaction for a sensitive DNA logic sensor for mutation detection. Chem Sci. Dec. 14, 2017;9(6):1666-1673.

Lyamichev et al., Structure-specific endonucleolytic cleavage of nucleic acids by eubacterial DNA polymerases. Science. May 7, 1993;260(5109):778-83.

Extended European Search Report for EP20865312, mailed Dec. 19, 2023, 10 pages.

* cited by examiner

F   Q
                        |   |
5'-CAGTTTTCTGTTCTTAGCCGGTTTTCCGGCTAAGACGTCCGTGGCCT-C6  3'

5' hairpin FRET Reporter #1

(SEQ ID NO:7)

F   Q
                        |   |
5'-CAACTTTTGTTGTTCTTAGCCGGTTTTCCGGCTAAGACGTCCGTGGCCT-C6  3'

5' hairpin FRET Reporter #2

(SEQ ID NO:8)

F   Q
                        |   |
5'-GCGGTTTTCGCTTCTTAGCCGGTTTTCCGGCTAAGACGTCCGTGGCCT-C6  3'

5' hairpin FRET Reporter #3

(SEQ ID NO:9)

FIG. 3B

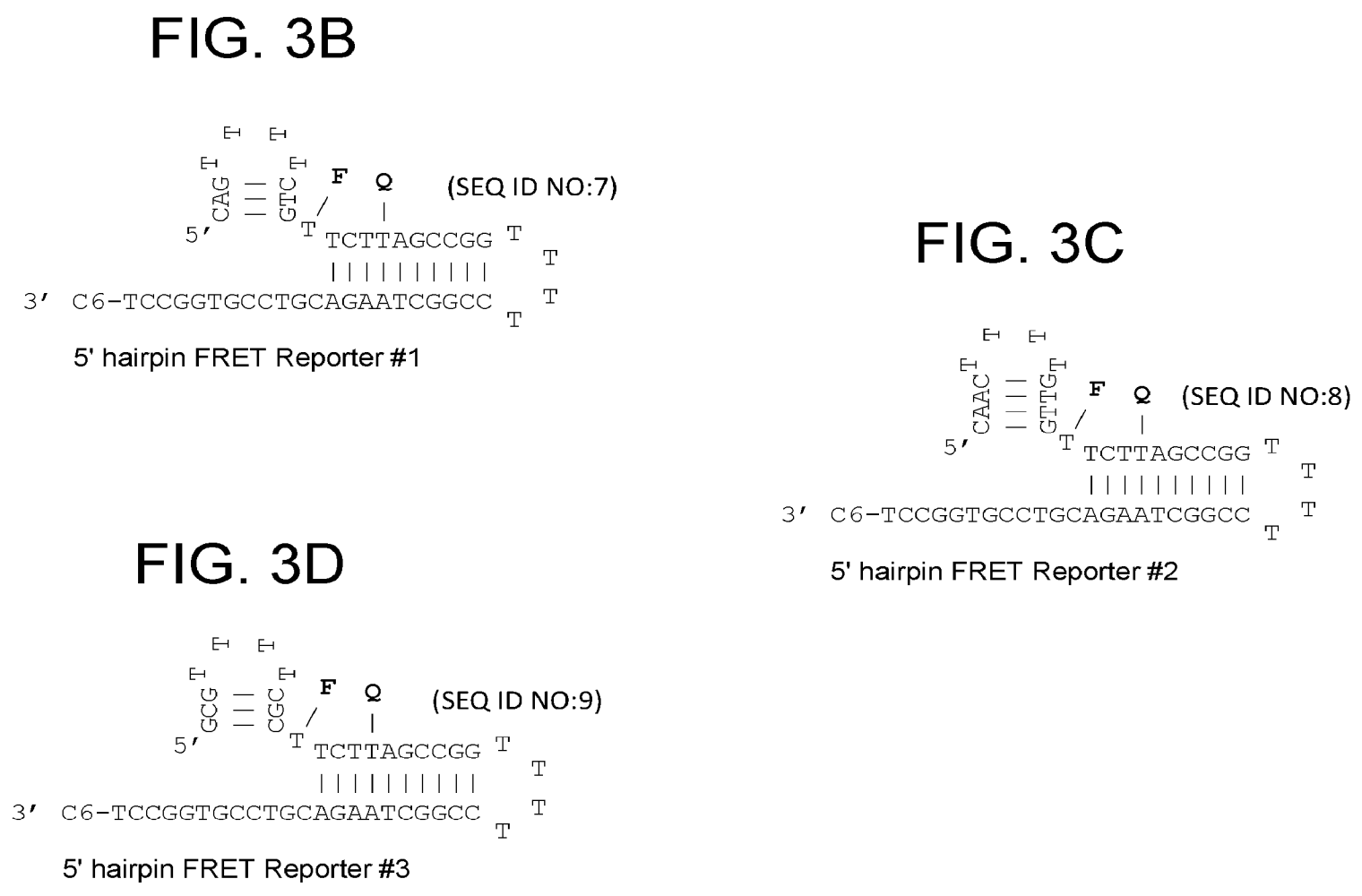

```
         T T
       L T
     L C GTC
     G | | | T
     T CAG  T   F   Q        (SEQ ID NO:7)
     5'    F /  |
              T TCTTAGCCGG T
                |||||||||||      T
3' C6—TCCGGTGCCTGCAGAATCGGCC    T
                              T
```

5' hairpin FRET Reporter #1

FIG. 3C

```
    T T
  L T
L C GTT
G | | | | L
T CAAC  T    F   Q        (SEQ ID NO:8)
5'   F /  |
         T TCTTAGCCGG T
           |||||||||||      T
3' C6—TCCGGTGCCTGCAGAATCGGCC    T
                         T
```

5' hairpin FRET Reporter #2

FIG. 3D

```
         T T
       L T
     L C GGC
     G | | | T
     T GCG  T   F   Q        (SEQ ID NO:9)
     5'    F /  |
              T TCTTAGCCGG T
                |||||||||||      T
3' C6—TCCGGTGCCTGCAGAATCGGCC    T
                              T
```

5' hairpin FRET Reporter #3

Reporting Cleavage Site

Quencher

Fluorophore

5' Hairpin

C6/3'-

5' Hairpin

Released Flap

C6/3'-

BELOW REACTION TEMP. → CLEAVAGE REPRESSED

Fluorescence Signal

C6/3'-

Cleavage

Unfolded 5' hairpin

C6/3'-

AT REACTION TEMP. → CLEAVABLE SUBSTRATE

BELOW REACTION TEMP. → CLEAVAGE REPRESSED

AT REACTION TEMP. → CLEAVABLE SUBSTRATE (SEQ ID NO:15)

5' HAIRPIN

TARGET CLEAVAGE SITE

UPSTREAM DUPLEX

DOWNSTREAM DUPLEX

FIG. 13B

Linear Fit:    Log(RFU/s) = 2.9544416 + 0.771237*Log(FEN1(nM))

Summary of Fit

| | |
|---|---|
| RSquare | 0.999447 |
| RSquare Adj | 0.999263 |
| Root Mean Square Error | 0.008293 |
| Mean of Response | 4.346062 |
| Observations (or Sum Wgts) | 5 |

Analysis of Variance

| Source | DF | Sum of Squares | Mean Square | F Ratio |
|---|---|---|---|---|
| Model | 1 | 0.37303559 | 0.373036 | 5423.618 |
| Error | 3 | 0.00020634 | 0.000069 | Prob > F |
| C. Total | 4 | 0.37324193 | | <.0001* |

Parameter Estimates

| Term | Estimate | Std Error | t Ratio | Prob>|t| |
|---|---|---|---|---|
| Intercept | 2.9544416 | 0.019257 | 153.42 | <.0001* |
| Log(FEN1(nM)) | 0.771237 | 0.010472 | 73.65 | <.0001* |

FIG. 14A
Target Cleavage Site
5' hairpin probe
Flap Assay Target Strand
5' Flap
BELOW REACTION TEMP. → CLEAVAGE REPRESSED
FIG. 14B
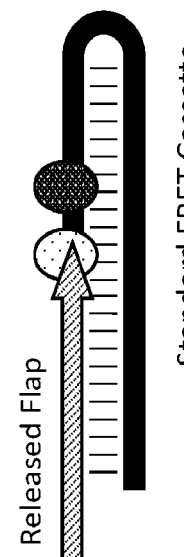
Released Flap
Standard FRET Cassette
FIG. 14C
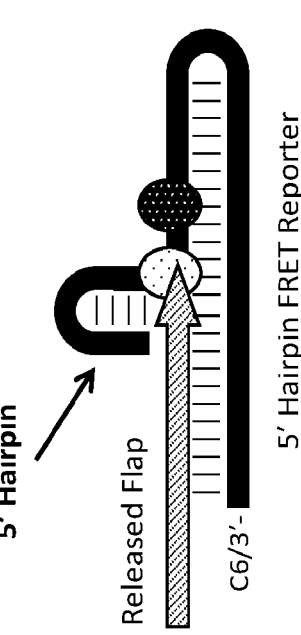
5' Hairpin
Released Flap
C6/3'-
5' Hairpin FRET Reporter 180 min at 50C, isothermal reaction at 63C (High Target)

180 min at 50C, isothermal reaction at 63C (High Target, Zoomed)

180 min at 50C, isothermal reaction at 63C (High Target, Zoomed)

180 min at 50C, isothermal reaction at 63C (High Target, Zoomed)

FIG. 15E 180 min at 50C, isothermal reaction at 63C (Mid Target)

180 min at 50C, isothermal reaction at 63C (Mid Target) Zoomed 180 min at 50C, isothermal reaction at 63C (Mid Target) Zoomed 180 min at 50C, isothermal reaction at 63C (Mid Target) Zoomed 180 min at 50C, isothermal reaction at 63C (Low Target)

180 min at 50C, isothermal reaction at 63C (Low Target), Zoomed 180 min at 50C, isothermal reaction at 63C (Low Target), Zoomed 180 min at 50C, isothermal reaction at 63C (Low Target), Zoomed 180 min at 50C, isothermal reaction at 63C (No Target)

180 min at 50C, isothermal reaction at 63C (No Target), Zoomed 180 min at 50C, isothermal reaction at 63C (No Target), Zoomed 180 min at 50C, isothermal reaction at 63C (No Target), Zoomed

SEQUENCE LISTING

<160> NUMBER OF SEQ ID NOS: 17

<210> SEQ ID NO 1
<211> LENGTH: 85
<212> TYPE: DNA
<213> ORGANISM: ArtIficial Sequence
<220> FEATURE:
<223> OTHER INFORMATION: Synthetic

<400> SEQUENCE: 1
caccaacctc ataaccttat cacacaaacc aatattaata cctacaccca caacactatc        60
ttaaacacct aatcaaaaaa acaaa                                             85

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
gtgtttgttt ttttgattag gtgtttaaga                                        30

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
ctttacacca acctcataac cttatc                                            26

<210> SEQ ID NO 4

-continued

```
<211> LENGTH: 21
<212> TYPE: DNA
<213> ORGANISM: Artificial Sequence
<220> FEATURE:
<223> OTHER INFORMATION: Synthetic

<400> SEQUENCE: 4
gacgcggaga tagtgttgtg g                                           21

<210> SEQ ID NO 5
<211> LENGTH: 10
<212> TYPE: DNA
<213> ORGANISM: Artificial Sequence
<220> FEATURE:
<223> OTHER INFORMATION: Synthetic

<400> SEQUENCE: 5
gacgcggaga                                                        10

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
tctagccggt tttccggctg agactccgcg tc                               32

<210> SEQ ID NO 7
<211> LENGTH: 47
<212> TYPE: DNA
<213> ORGANISM: Artificial Sequence
<220> FEATURE:
<223> OTHER INFORMATION: Synthetic

<400> SEQUENCE: 7
cagttttctg ttcttagccg gttttccggc taagacgtcc gtggcct              47

<210> SEQ ID NO 8
<211> LENGTH: 49
<212> TYPE: DNA
<213> ORGANISM: Artificial Sequence
<220> FEATURE:
<223> OTHER INFORMATION: Synthetic

<400> SEQUENCE: 8
caacttttgt tgttcttagc cggttttccg gctaagacgt ccgtggcct            49

<210> SEQ ID NO 9
<211> LENGTH: 48
<212> TYPE: DNA
<213> ORGANISM: Artificial Sequence
<220> FEATURE:
<223> OTHER INFORMATION: Synthetic

<400> SEQUENCE: 9
cgcttttctc gttcttagcc ggttttccgg ctaagacgtc cgtggcct             48

<210> SEQ ID NO 10
<211> LENGTH: 41
<212> TYPE: DNA
<213> ORGANISM: Artificial Sequence
<220> FEATURE:
<223> OTHER INFORMATION: Synthetic

<400> SEQUENCE: 10
```
tcttagccgg ttttccggct gagactccgc ttttgcggag g                          41

<210> SEQ ID NO 11
<211> LENGTH: 53
<212> TYPE: DNA
<213> ORGANISM: Artificial Sequence
<220> FEATURE:
<223> OTHER INFORMATION: Synthetic

<400> SEQUENCE: 11
tcttagccgg ttttccggct gagacgtccg tggccttttt aggccacgga cgg            53

<210> SEQ ID NO 12
<211> LENGTH: 68
<212> TYPE: DNA
<213> ORGANISM: Artificial Sequence
<220> FEATURE:
<223> OTHER INFORMATION: Synthetic

<400> SEQUENCE: 12
tccttattac ttttgtaata aggattcttc agccggtttt ccggctgaag actccgcttt     60
tgcggagg                                                              68

<210> SEQ ID NO 13
<211> LENGTH: 64
<212> TYPE: DNA
<213> ORGANISM: Artificial Sequence
<220> FEATURE:
<223> OTHER INFORMATION: Synthetic

<400> SEQUENCE: 13
tccttattac gtaataagga ttcttcagcc ggttttccgg ctgaagactc cgcttttgcg     60
gagg                                                                  64

<210> SEQ ID NO 14
<211> LENGTH: 64
<212> TYPE: DNA
<213> ORGANISM: Artificial Sequence
<220> FEATURE:
<223> OTHER INFORMATION: Synthetic

<400> SEQUENCE: 14
tccttattac gtaataagga ttcttcagcc ggttttccgg ctgaagactc cgcttttgcg     60
gagg                                                                  64

<210> SEQ ID NO 15
<211> LENGTH: 54
<212> TYPE: DNA
<213> ORGANISM: Artificial Sequence
<220> FEATURE:
<223> OTHER INFORMATION: Synthetic

<400> SEQUENCE: 15
gtcttttgac ttcttcagcc ggttttccgg ctgaagacgc cgcttttgcg gcgg           54

<210> SEQ ID NO 16
<211> LENGTH: 56
<212> TYPE: DNA
<213> ORGANISM: Artificial Sequence
<220> FEATURE:
<223> OTHER INFORMATION: Synthetic

<400> SEQUENCE: 16

-continued

```
gtcatttttg acttcttcag ccggtttttcc ggctgaagac gccgcttttg cggcgg          56

<210> SEQ ID NO 17
<211> LENGTH: 54
<212> TYPE: DNA
<213> ORGANISM: Artificial Sequence
<220> FEATURE:
<223> OTHER INFORMATION: Synthetic

<400> SEQUENCE: 17
gtcacgtgac ttcttcagcc ggttttccgg ctgaagacgc cgcttttgcg gcgg           54
```

STRUCTURE AND TEMPERATURE-DEPENDENT FLAP ENDONUCLEASE SUBSTRATES

The present application is a § 371 National Entry application of PCT/US2020/051118, filed Sep. 16, 2020, which claims priority to U.S. Provisional Application Ser. No. 62/901,085, filed Sep. 16, 2019, each of which is incorporated herein by reference.

SEQUENCE LISTING

The text of the computer readable sequence listing filed herewith, titled "37800-252 SEQUENCE LISTING", created Mar. 15, 2022, having a file size of 3,723 bytes, is hereby incorporated by reference in its entirety.

FIELD OF THE INVENTION

The invention relates to flap endonuclease enzymes and the modulation of enzymatic activity of these enzymes using structures in the nucleic acid substrate that repress enzymatic cleavage at a reporting cleavage site at lower temperatures and that change structure to permit cleavage of the substrate at the reporting cleavage site at elevated temperature.

BACKGROUND OF THE INVENTION

Eubacteria, Eukarya and Archaea comprise enzymes having 5' exo- and endonuclease functions that participate in DNA repair. These enzymatic activities are found, for example, in the 5'-exonuclease domain of DNA polymerase I (DNA Pol I) in eubacteria, and in the FEN-1 proteins of eukaryotes and archaeal organisms. These enzymes recognize and cleave a variety of nucleic acid structures comprising duplexed and single-stranded regions, with a preferred structure being displaced 5' strands formed by templated polymerase extension of the 3' end of an upstream strand. The resulting structure, comprising a template strand that is base-paired to an upstream strand having a 3' terminal end, and to a downstream strand having a single-stranded 5' flap may be referred to as a flap structure, and the enzymes that recognize and cleave the structure may be referred to generally as flap endonucleases or FENs. (See, e.g., Kaiser M. W., et al, J. Biol. Chem. 274(30): 21387-94 (1999); Shen, B., et al., BioEssays 27:717-729, (2005); and Finger D. L. et al., Subcell Biochem. 62: 301-326 (2012), each of which is incorporated herein by reference in its entirety for all purposes) Optimal structures comprise an overlap between the upstream and downstream duplexes. The overlap may be one or more nucleotides of sequence overlap, as would occur when the sequence at the end of an extending primer duplicates the sequence of a displaced 5' flap, or it may be physical, as occurs when a 3' terminal nucleotide of in invasive oligonucleotide overlaps with the downstream duplex of a flap strand, but is not complementary to a corresponding template nucleotide, resulting in a double flap structure (see, e.g., Kaiser, supra). Flap endonuclease recognize the 5' end of the flap strand, and cleavage of the preferred substrate structure typically occurs one nucleotide into the downstream duplex, in a process that comprises threading or clamping the single-stranded 5' flap to position the molecules for precise cleavage (Shen, supra).

Flap endonucleases are useful in in vitro detection assays. For example, QuARTS and INVADER flap assays makes use of Archaeal flap endonucleases to cleave synthetic flap probes in response to the presence of target nucleic acid strands.

SUMMARY OF THE INVENTION

Provided herein are compositions and methods directed to flap oligonucleotides that are modified to provide control of FEN activity, e.g., in an assay. For example, in some embodiments, modifications on a flap oligonucleotide are thermolabile, such that cleavage of the flap substrate is repressed at a first temperature and is de-repressed at elevated temperature, e.g., when an assay reaction is moved from room temperature to a higher temperature for an incubation period. Accordingly, in some embodiments, the technology provides oligonucleotides that comprise a 5' flap modification, e.g., a duplexed region, preferably a hairpin-forming region, that represses cleavage of the modified oligonucleotide at a target cleavage site by flap endonucleases at ambient temperature, and that is convertible to cleavable form under conditions in which the 5' flap modification does not repress cleavage, e.g., under an increase in temperature in which the 5' flap is not in a duplexed or hairpin form.

In some embodiments the technology provides a composition comprising a 5' hairpin invasive cleavage structure having a target cleavage site, the 5' hairpin cleavage structure comprising a 5' flap, a downstream duplex stem, and an upstream duplex stem that define an invasive cleavage structure, wherein the 5' flap comprises a hairpin-forming region, and wherein formation of a hairpin in the hairpin-forming region suppresses flap endonuclease cleavage of the 5' hairpin invasive cleavage structure at the target cleavage site. In certain embodiments, the 5' hairpin invasive cleavage structure is cleavable at the target cleavage site by a FEN-1 endonuclease, preferably by Afu FEN-1 in a $Mg^{++}$ flap assay buffer. In preferred embodiments, the target cleavage site is in the downstream duplex stem.

In certain preferred embodiments, the 5' hairpin invasive cleavage structure is selected from:

i) an invasive cleavage structure comprising an invasive oligonucleotide, a 5' hairpin probe oligonucleotide and a target nucleic acid, wherein the annealing of the 5' hairpin probe oligonucleotide to the target nucleic acid forms the downstream duplex stem and annealing of the invasive oligonucleotide to the target nucleic acid forms the upstream duplex stem;

ii) a structure comprising a 5' hairpin reporter and a nucleic acid molecule, the 5' hairpin reporter comprising the 5' flap comprising 5' hairpin-forming region, a downstream duplex stem, and a 3' portion complementary to a 3' terminal portion of the nucleic acid molecule, wherein annealing of the 3' terminal portion of the nucleic acid molecule to the 3' portion of the 5' hairpin reporter forms the upstream duplex of the invasive cleavage structure; and iii) an oligonucleotide 5' hairpin test substrate the oligonucleotide comprising a 5' flap comprising a 5' hairpin-forming region, a downstream duplex stem, and an upstream duplex stem that define an invasive cleavage structure.

In some embodiments of the structure comprising a 5' hairpin reporter and a nucleic acid molecule, the nucleic acid molecule also comprises a 5' hairpin forming region. For example, in some embodiments, the nucleic acid molecule is a 5' flap released from a 5' hairpin probe.

In some embodiments, the 5' hairpin invasive cleavage structure comprises a FRET labeling system. Preferably, a first member of a FRET labeling system is attached at a first position on the 5' hairpin invasive cleavage structure and a second member of a FRET labeling system is attached at a second position on the 5' hairpin invasive cleavage structure, and the target cleavage site is between the first position and the second position.

The positions of members of FRET labeling systems are not limited to any particular sites on the 5' hairpin invasive cleavage structure. In some embodiments, the first position and the second position are separated in the invasive cleavage structure, e.g., along a length of nucleic acid in the 5' hairpin invasive cleavage structure, by no more than 20 nucleotides, preferably no more than 10 nucleotides, more preferably no more than 9, 8, 7, 6, 5, 4, or 3 nucleotides.

In some embodiments, the 5' hairpin invasive cleavage structure comprises an oligonucleotide comprising a 3' blocker, and in preferred embodiments the 3' blocker is selected from a 3' amine, a 3' phosphate, a 3' biotin, a 3' hexanediol, and a 3' dideoxynucleotide.

In some embodiments of the technology, the composition comprises a solution, e.g., a buffer. In certain embodiments, the buffer solution comprises a cation, and in preferred embodiments, the buffer solution comprising a cation is a $Mg^{++}$ flap assay buffer.

In some embodiments, the technology of any of the compositions described above further comprises a flap endonuclease. In preferred embodiments, the flap endonuclease comprises a FEN-1 endonuclease, preferably a thermostable FEN-1 endonuclease, more preferably a thermostable FEN-1 endonuclease from an Archaeal organism. In particularly preferred embodiments, the FEN-1 endonuclease comprises one or more of Afu FEN-1, Ave FEN-1, and Pfu FEN-1.

In embodiments of any of the embodiments described above, it is contemplated that embodiments of the composition may comprising one or more PCR-flap assay reagents, including but not limited to PCR-flap assay reagents comprising one or more of: DNA polymerase; deoxynucleoside triphosphates; a flap oligonucleotide; and primers. In some embodiments, PCR reagents further comprise reverse transcriptase.

In some embodiments, the technology provides a composition comprising an oligonucleotide 5' hairpin reporter for forming an invasive cleavage structure with a nucleic acid molecule (e.g., a target molecule to be detected, or a cleavage product in a flap assay), the invasive cleavage structure having a target cleavage site, the 5' hairpin reporter comprising a 5' hairpin-forming region, a downstream duplex stem, and a 3' portion complementary to a 3' terminal portion of the nucleic acid molecule, wherein annealing of the 3' terminal portion of the nucleic acid molecule to the 3' portion of the 5' hairpin reporter forms an upstream duplex of an invasive cleavage structure. In certain embodiments, the invasive cleavage structure is cleavable at the target cleavage site by a FEN-1 endonuclease, preferably by Afu FEN-1 in a $Mg^{++}$ flap assay buffer. In preferred embodiments, the target cleavage site is in the downstream duplex stem of the 5' hairpin reporter, and in particularly preferred embodiments, the downstream duplex stem is a hairpin stem comprising a loop. In preferred embodiments, cleavage of the 5' hairpin reporter is repressed at room temp. For example, in such embodiments, the 5' hairpin forming region of the 5' hairpin reporter may be in the form of a hairpin when the composition is at room temperature.

In some embodiments, the composition further comprises a nucleic acid molecule comprising a 3' terminal portion complementary to the 3' portion of the 5' hairpin reporter.

In some embodiments, the 5' hairpin reporter comprises a label. In certain embodiments, the 5' hairpin reporter comprises a FRET labeling system. In preferred embodiments, a first member of a FRET labeling system is attached at a first position on the 5' hairpin reporter and a second member of a FRET labeling system is attached at a second position on the 5' hairpin reporter, and the target cleavage site is between the first position and the second position. The positions of members of FRET reporter system are not limited to any particular distance along the strand of the 5' hairpin reporter molecule and may be at the termini of the molecule. In some embodiments, the first position and the second position are separated along the length of the 5' hairpin reporter by no more than 20, 19, 18, 17, 16, 15, 14, 13, 12, 11, 10, 9, 8, 7, 6, 5, 4, or 3 nucleotides.

In some embodiments, 5' hairpin reporter further comprises a 3' blocker. Preferably, the 3' blocker is selected from a 3' amine, a 3' phosphate, a 3' biotin, a 3' hexanediol, and a 3' dideoxynucleotide.

In some embodiments, the composition further comprises a buffer solution comprising a cation. In certain preferred embodiments, the buffer solution comprising a cation is a $Mg^{++}$ flap assay buffer. In some embodiments, the composition further comprises a flap endonuclease, e.g., a FEN-1 endonuclease, preferably a thermostable FEN-1 endonuclease, more preferably a thermostable FEN-1 endonuclease from an Archaeal organism. In particularly preferred embodiments, the FEN-1 endonuclease comprises one or more of Afu FEN-1, Ave FEN-1, and Pfu FEN-1.

In some embodiments, a composition of the technology comprises one or more PCR-flap assay reagents. In certain preferred embodiments, the PCR-flap assay reagents comprise one or more of DNA polymerase, deoxynucleoside triphosphates, a flap oligonucleotide, and primers. In some embodiments, the composition comprises a target nucleic acid.

Also provided herein are methods of using compositions such as those described above. For example, embodiments of the technology provide method a comprising:
  i) providing
    a) an oligonucleotide 5' hairpin reporter for forming an invasive cleavage structure with a nucleic acid molecule, the invasive cleavage structure having a target cleavage site; and
    b) a nucleic acid molecule;
  wherein the 5' hairpin reporter comprises a 5' hairpin-forming region, a downstream duplex stem, and a 3' portion complementary to a 3' terminal portion of the nucleic acid molecule, and wherein annealing of the 3' terminal portion of the nucleic acid molecule to the 3' portion of the 5' hairpin reporter forms an upstream duplex of an invasive cleavage structure;
  and
  ii) annealing the 3' terminal portion of the nucleic acid molecule to the 3' portion of the 5' hairpin reporter.

In some embodiments, thee invasive cleavage structure is cleavable at the target cleavage site by Afu FEN-1 in a $Mg^{++}$ flap assay buffer. In preferred embodiments, the target cleavage site is in the downstream duplex stem of the 5' hairpin reporter, and in particularly preferred embodiments, the downstream duplex stem is a hairpin stem comprising a loop. In some embodiments, the composition further comprises a nucleic acid molecule comprising a 3' terminal portion complementary to the 3' portion of the 5' hairpin reporter. In preferred embodiments, cleavage of the 5' hairpin reporter is repressed at room temp. For example, in such embodiments, the 5' hairpin forming region of the 5' hairpin reporter may be in the form of a hairpin when the composition is at room temperature.

In some embodiments, the 5' hairpin reporter comprises a label. In certain embodiments, the 5' hairpin reporter comprises a FRET labeling system. In preferred embodiments, a first member of a FRET labeling system is attached at a first position on the 5' hairpin reporter and a second member of a FRET labeling system is attached at a second position on the 5' hairpin reporter, and the target cleavage site is between the first position and the second position. The positions of members of FRET reporter system are not limited to any particular distance along the strand of the 5' hairpin reporter molecule and may be at the termini of the molecule. In some embodiments, the first position and the second position are separated along the length of the 5' hairpin reporter by no more than 20, 19, 18, 17, 16, 15, 14, 13, 12, 11, 10, 9, 8, 7, 6, 5, 4, or 3 nucleotides.

In some embodiments, 5' hairpin reporter further comprises a 3' blocker. Preferably, the 3' blocker is selected from a 3' amine, a 3' phosphate, a 3' biotin, a 3' hexanediol, and a 3' dideoxynucleotide.

In some embodiments, the method comprises cleaving the invasive cleavage structure in a reaction mixture, e.g., a reaction mixture comprising a cation. In preferred embodiments, the reaction mixture comprises a $Mg^{++}$ flap assay buffer. In preferred embodiments, the reaction mixture comprises a flap endonuclease, e.g., a flap endonuclease comprising a FEN-1 endonuclease, preferably a thermostable FEN-1 endonuclease, more preferably a thermostable FEN-1 endonuclease from an Archaeal organism. In particularly preferred embodiments, the FEN-1 endonuclease comprises one or more of Afu FEN-1, Ave FEN-1, and Pfu FEN-1.

The technology also finds application in PCR-flap assays. Accordingly, in some embodiments, the reaction mixture comprises one or more PCR-flap assay reagents. In certain preferred embodiments, the PCR-flap assay reagents comprise one or more of DNA polymerase, deoxynucleoside triphosphates, a flap oligonucleotide, and primers. In some embodiments, the composition comprises a target nucleic acid.

The technology also finds application in test substrates, e.g., for characterizing flap endonucleases, flap assay conditions, etc. For example, in some embodiments, the technology provides a composition comprising an oligonucleotide 5' hairpin test substrate for forming an invasive cleavage structure having a target cleavage site, the 5' hairpin test substrate comprising a 5' flap, a downstream duplex stem, and an upstream duplex stem that define an invasive cleavage structure cleavable at the target cleavage site by Afu FEN-1 endonuclease in a Mg' flap assay buffer, wherein the 5' flap comprises a hairpin-forming region, and wherein formation of a hairpin in the hairpin-forming region suppresses FEN-1 endonuclease cleavage of the 5' hairpin test substrate at the target cleavage site. In preferred embodiments, the target cleavage site is in the downstream duplex stem of the 5' hairpin test substrate. In some embodiments, the downstream duplex stem is a hairpin stem comprising a loop. In preferred embodiments, cleavage of the 5' hairpin test substrate is repressed at room temp. For example, in such embodiments, the 5' hairpin forming region of the 5' hairpin test substrate may be in the form of a hairpin when the composition is at room temperature.

In some embodiments, the 5' hairpin test substrate comprises a label, such as a FRET labeling system. In preferred embodiments, first member of a FRET labeling system is attached at a first position on the 5' hairpin test substrate and a second member of a FRET labeling system is attached at a second position on the 5' hairpin test substrate, wherein the target cleavage site is between the first position and the second position. The positions of members of FRET reporter system are not limited to any particular distance along the strand of the 5' hairpin test substrate molecule, and may be at the termini of the molecule. In some embodiments, the first position and the second position are separated along the length of the 5' hairpin test substrate by no more than 20, 19, 18, 17, 16, 15, 14, 13, 12, 11, 10, 9, 8, 7, 6, 5, 4, or 3 nucleotides.

In some embodiments, the composition further comprises a buffer solution comprising a cation. In certain preferred embodiments, the buffer solution comprising a cation is a $Mg^{++}$ flap assay buffer. In some embodiments, the composition further comprises a flap endonuclease, e.g., a FEN-1 endonuclease, preferably a thermostable FEN-1 endonuclease, more preferably a thermostable FEN-1 endonuclease from an Archaeal organism. In particularly preferred embodiments, the FEN-1 endonuclease comprises one or more of Afu FEN-1, Ave FEN-1, and Pfu FEN-1.

Also provided herein are methods of using compositions such as those described above. For example, embodiments of the technology provide method of testing a flap endonuclease, comprising:

i) providing an oligonucleotide 5' hairpin test substrate for forming an invasive cleavage structure having a target cleavage site, the 5' hairpin test substrate comprising:

a) a 5' flap, b) a downstream duplex stem and an upstream duplex stem that define an invasive cleavage structure cleavable at the target cleavage site by Afu FEN-1 endonuclease in a $Mg^{++}$ flap assay buffer, wherein the 5' flap comprises a hairpin-forming region, and wherein formation of a hairpin in the hairpin-forming region suppresses FEN-1 endonuclease cleavage of the 5' hairpin test substrate at the target cleavage site;

ii) exposing the 5' hairpin test substrate to a flap endonuclease in a reaction mixture; and iii) detecting the presence or absence of cleavage of the 5' hairpin test substrate.

In preferred embodiments, the target cleavage site is in the downstream duplex stem of the 5' hairpin test substrate, and in certain particularly preferred embodiments, the downstream duplex stem is a hairpin stem comprising a loop.

In some embodiments, the 5' hairpin test substrate comprises a label, such as a FRET labeling system. In preferred embodiments, first member of a FRET labeling system is attached at a first position on the 5' hairpin test substrate and a second member of a FRET labeling system is attached at a second position on the 5' hairpin test substrate, wherein the target cleavage site is between the first position and the second position. The positions of members of FRET reporter system are not limited to any particular distance along the strand of the 5' hairpin test substrate molecule, and may be at the termini of the molecule. In some embodiments, the first position and the second position are separated along the length of the 5' hairpin test substrate by no more than 20, 19, 18, 17, 16, 15, 14, 13, 12, 11, 10, 9, 8, 7, 6, 5, 4, or 3 nucleotides.

In some embodiments, the method comprises cleaving the 5' hairpin test substrate in a reaction mixture, e.g., a reaction mixture comprising a cation. In preferred embodiments, the reaction mixture comprises a Mg$^{++}$ flap assay buffer. In preferred embodiments, the reaction mixture comprises a flap endonuclease, e.g., a flap endonuclease comprising a FEN-1 endonuclease, preferably a thermostable FEN-1 endonuclease, more preferably a thermostable FEN-1 endonuclease from an Archaeal organism. In particularly preferred embodiments, the FEN-1 endonuclease comprises one or more of Afu FEN-1, Ave FEN-1, and Pfu FEN-1. In preferred embodiments, cleavage of the 5' hairpin test substrate is repressed at room temp. For example, in such embodiments, the 5' hairpin forming region of the 5' hairpin test substrate may be in the form of a hairpin when the composition is at room temperature.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein in reference to non-target DNA, the term "exogenous" refers to non-target DNA that is isolated and purified from a source other than the source or sample containing the target DNA. For example, purified fish DNA is exogenous DNA with respect to a sample comprising human target DNA, e.g., as described in U.S. Pat. No. 9,212,392, which is incorporated herein by reference. Exogenous DNA need not be from a different organism than the target DNA. For example, purified fish DNA obtained commercially would be exogenous if added to a reaction configured to detect a target nucleic acid in a sample from a particular fish. In preferred embodiments, exogenous DNA is selected to be undetected by an assay configured to detect and/or quantify the target nucleic acid in the reaction into which the exogenous DNA is added.

As used herein, a "DNA fragment" or "small DNA" or "short DNA" means a DNA that consists of no more than approximately 200 base pairs or nucleotides in length.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically. In some embodiments, an oligonucleotide primer is used with a template nucleic acid and extension of the primer is template dependent, such that a complement of the template is formed.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al., (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured, and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the "INVADER" flap assay, or invasive cleavage assay, (Hologic, Inc.) described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and in combined PCR/invasive cleavage assays (Hologic, Inc., e.g., in U.S. Patent Publications 2006/0147955 and 2009/0253142), each of which is herein incorporated by reference in its entirety for all purposes); enzyme mismatch cleavage methods (e.g., Variagenics, U.S. Pat. Nos. 6,110,684, 5,958, 692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barany Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893 B2 (application. Ser. No. 13/941,122), incorporated herein by reference in its entirety for all purposes, and as diagrammed in FIG. 1. Because many copies of the FRET cassette are cleaved for each copy of the target amplicon produced, the assay is said to produce "signal amplification" in addition to target amplification. See also Allawi H T, et al. *J of Clin Microbio* 2006; vol 44, no. 9: 3443-3447. Additional amplification plus invasive cleavage detection configurations, termed the QuARTS method, are described in U.S. Pat. Nos. 8,361,720, 8,715,937, and 8,916,344, incorporated herein by reference in their entireties for all purposes.

A "flap oligonucleotide" refers to an oligonucleotide cleavable in a detection assay, such as an invasive cleavage assay, by a flap endonuclease. In preferred embodiments, a flap oligonucleotide forms an invasive cleavage structure with other nucleic acids, e.g., a target or template nucleic acid and an invasive oligonucleotide. Flap assay reagents may optionally contain a target or template nucleic acid to which an invasive oligonucleotide and flap oligonucleotide bind. In particularly preferred embodiments, flap assay reagents comprise a $Mg^{++}$ flap assay buffer, as discussed herein.

As used herein, the term "flap endonuclease" refers to a structure-specific nucleolytic enzyme that cleaves a nucleic acid flap structure, e.g., an invasive cleavage structure. Flap endonuclease include, e.g., 5'-exonuclease domains of the DNA polymerase I proteins of Eubacteria and the FEN-1 proteins of Eukarya and Archaea. (Kaiser, et al., supra). Flap endonuclease may cleave additional structures, e.g., pseudo-Y, 5' overhang, and gap structures. See, e.g., Shen, B., BioEssays 27:717-729 (2005), and Finger, L D., Subcell Biochem. 62:301-326 (2012), each of which is incorporated herein in its entirety.

The terms "FEN-1" as used herein in reference to an enzyme refers to a non-polymerase flap endonuclease from a eukaryote or archaeal organism, as encoded by a FEN-1 (Flap Structure-Specific Endonuclease 1) gene. See, e.g., Kaiser, et al., supra, WO 02/070755, and U.S. Pat. No. 7,122,364, which are incorporated by reference herein in their entireties for all purposes. The term "FEN-1 activity" refers to any enzymatic activity of a FEN-1 enzyme. FEN-1 endonucleases also comprise modified FEN-1 proteins, e.g., chimerical proteins comprising portions of FEN-1 enzymes from different organisms, and enzymes comprising one or more mutations (e.g., substitutions, deletions, insertions, etc.), as described in WO 02/070755, and U.S. Pat. No. 7,122,364. The term "FEN1" is used interchangeably with "FEN1" herein.

As used herein, the term "PCR-flap assay" is used interchangeably with the term "PCR-invasive cleavage assay" and refers to an assay configuration combining PCR target amplification and detection of the amplified DNA by formation of a first overlap cleavage structure comprising amplified target DNA, and a second overlap cleavage structure comprising a cleaved 5' flap from the first overlap cleavage structure and a labeled reporter oligonucleotide, e.g., a "FRET cassette" or 5' hairpin FRET reporter oligonucleotide. In the PCR-flap assay as used herein, the assay reagents comprise a mixture containing DNA polymerase, FEN-1 endonuclease, a primary probe comprising a portion complementary to a target nucleic acid, and a FRET cassette or 5' hairpin FRET reporter, and the target nucleic acid is amplified by PCR and the amplified nucleic acid is detected simultaneously (i.e., detection occurs during the course of target amplification). PCR-flap assays include the QuARTS assays described in U.S. Pat. Nos. 8,361,720; 8,715,937; and 8,916,344, and the amplification assays of U.S. Pat. No. 9,096,893 (for example, as diagrammed in FIG. 1 of that patent.) LQAS assays are flap assays using probe oligonucleotides having a longer target-specific region (Long probe Quantitative Amplified Signal, "LQAS") and TELQAS assays combine the LQAS probe oligos with a pre-amplification step (Target Enrichment Long probe Quantitative Amplified Signal), as is described in U.S. Pat. No. 10,648,025, and in WO 2020/112869, each of which is incorporated herein by reference in its entirety.

As used herein in reference to 5' hairpin forming regions and reduction of cleavage of invasive cleavage structures, the term "repress" and derivatives thereof are used interchangeably with "suppress" and derivatives thereof as indicating reduction or inhibition of cleavage, e.g., by a flap endonuclease, for example, by formation of a hairpin in a 5' hairpin forming region. Repression and suppression are indicative of reversible inhibition or reduction of cleavage generally, without being limited to any particular mechanism of inhibiting or reducing cleavage of an invasive cleavage structure.

As used herein, the term "PCR-flap assay reagents" refers to one or more reagents for detecting target sequences in a PCR-flap assay, the reagents comprising nucleic acid molecules capable of participating in amplification of a target nucleic acid and in formation of a flap cleavage structure in the presence of the target sequence, in a mixture containing DNA polymerase, FEN-1 endonuclease and a FRET cassette or 5' hairpin FRET reporter.

As used herein, the term "invasive cleavage structure" refers to a cleavage structure comprising a template nucleic acid, an upstream nucleic acid (e.g., an invasive oligonucleotide, or a 3' portion of a template strand folded back and hybridized to form a hairpin), and iii) a downstream nucleic acid (e.g., a probe, or a 5' portion of a template strand folded back and hybridized to form a hairpin), where the upstream and downstream nucleic acids anneal to adjacent regions of the template strand (i.e., regions of a template strand that are next to each other on the strand, not separated by intervening nucleotides or base pairs) and where an overlap forms between the 3' end of the upstream nucleic acid and the duplex formed between the downstream nucleic acid and the template nucleic acid. An overlap occurs where one or more bases from the upstream and downstream nucleic acids occupy the same position with respect to a particular nucleotide in a template strand, whether or not the overlapping base(s) of the upstream nucleic acid are complementary with corresponding nucleotide in the template strand, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No.

6,090,543, incorporated herein by reference in its entirety. As used herein in reference to an invasive cleavage structure, the term "upstream duplex" refers to a duplex formed between a template strand and a hybridized upstream nucleic acid strand having a 3' end, and the term "downstream duplex" refers to a duplex formed between a template strand and a hybridized downstream nucleic acid having a 5' end, such that an overlapping flap endonuclease substrate is formed by the adjacent hybridized regions of the upstream and downstream nucleic acid strands. In some embodiments, the upstream nucleic acid, the downstream nucleic acid, or both, are part of the same strand of nucleic acid as the template strand. See, e.g., FIGS. 1A, 1B, and 1C, which illustrates the upstream and downstream duplex regions of invasive cleavage structures formed from 3 strands, 2 strands, or 1 strand of nucleic acid, respectively. In some embodiments, one or more of the nucleic acid strands may be attached to each other through a non-nucleic acid chemical linkage (e.g., a multi-carbon chain). See, e.g., U.S. Pat. No. 8,445,238, which is incorporated herein by reference in its entirety.

As used herein in reference to cleavage of an invasive cleavage structure, the term "target cleavage site" refers to a preferred site (or sites) of cleavage on a nucleic acid structure (e.g., an invasive cleavage structure) by a structure-specific nuclease (e.g., a FEN-1 endonuclease) that recognizes the structure as a cleavage substrate. For example, as discussed by Kaiser, et al., 5' flap endonucleases, including FEN-1 endonucleases, typically cleave an invasive cleavage structure in the downstream nucleic acid, generally after the first base-paired nucleotide, i.e., one nucleotide into the downstream duplex. In preferred embodiments described herein, a target cleavage site may be used as a reporting cleavage site in a flap assay. For example, in certain preferred embodiments, donor and acceptor moieties of a FRET labeling system (e.g., fluorophore and a quencher moieties) are positioned such that they are separated upon cleavage of the invasive cleavage structure at a target cleavage site, such that an increase in fluorescence in the reaction mixture reports the cleavage at the target cleavage site. The technology is not limited by any particular placement of moieties of the FRET system on the cleavage structure. For example, in some embodiments, moieties of a FRET system are attached to a probe or reporter at positions that closely flank the reporting cleavage site, e.g., that are within 1, 2, or a few nucleotides on either side of a reporting cleavage site, while in other embodiments, moieties of a FRET system are more widely spaced, e.g., 5, 6, 7, 8, 9, 10, etc., nucleotides apart on a nucleic acid strand. In some embodiments, one or more moieties of a FRET system are at or near the termini of a nucleic acid strand that is cleaved in an invasive cleavage structure. In preferred embodiments, an invasive cleavage structure is cleavable at a target cleavage site by a FEN-1 endonuclease from *Archaeoglobus fulgidus* ("Afu FEN-1") in a $Mg^{++}$ flap assay buffer, as discussed below. See also, e.g., U.S. Pat. No. 6,562,611 to Kaiser, et al., and Kaiser M. W., et al. (1999) J. Biol. Chem., 274:21387, each of which is incorporated herein by reference in its entirety for all purposes.

As used herein in reference to nucleic acid substrate structures for flap endonucleases, a "5' hairpin" refers to a hairpin or hairpin-forming sequence that is on the same strand as a target cleavage site, and that is in the 5' direction from the target cleavage site, along the same strand of nucleic acid. A 5' hairpin is not limited to any particular location on the strand 5' of the target cleavage site. In some embodiments, a 5' hairpin-forming region may comprise the 5' terminal nucleotide of a 5' flap, while in other embodiments, a 5' hairpin-forming region may be flanked by non-self-complementary regions on one or both sides (i.e., in the 5' and/or 3' directions) of the 5' hairpin-forming sequence. In some embodiments, an entire 5' flap is composed of a hairpin-forming sequence.

The term "template" as used in reference to a nucleic acid strand of a flap structure, e.g., an invasive cleavage structure, refers to the strand to which upstream and downstream nucleic acids or nucleic acid regions hybridize to form an invasive cleavage structure. While a template strand may serve as template for extension of a primer by a polymerase, e.g., in a PCR flap endonuclease assay, use of the term is not limited to polymerizing assays or reactions.

As used herein, the term "3' end blocker" refers to a 3' end modification, e.g., on an oligonucleotide, that suppresses cleavage by a flap endonuclease of an invasive cleavage structure when the 3' end blocker is present on the 3' end of an upstream nucleic acid in the cleavage structure. For example, 3' amines, 3' phosphate (3'-PO$_4$), 3' biotin, 3' C$_6$ (a 6-carbon glycol spacer, also referred to as "3' hexanediol"), and 3' dideoxynucleotides suppress flap cleavage if present on an upstream nucleic acid. See, e.g., Kaiser, et al., supra.

As used herein, the term "Mg$^{++}$ flap assay buffer" refers to a buffer solution for a flap endonuclease that includes Mg$^{++}$ as the predominant or essentially only divalent cation in the buffer, such that assay reactions performed in the buffer, e.g., flap assays, exhibit characteristics of the presence of Mg$^{++}$ (e.g., high specificity of some flap endonucleases for invasive cleavage structures as compared to, e.g., Y-structures, pseudo Y structures), and do not exhibit characteristics associated with the presence of other divalent cations (e.g., alternative cleavage activities of flap endonucleases associated with use of Mn$^{++}$ with or in place of Mg$^{++}$), as described, e.g., by Kaiser, et al., supra. In some embodiments the flap assay buffer has very low or no KCl and comprises elevated Mg$^{++}$ as compared to standard PCR buffer, (e.g., a flap assay buffer of the technology comprises >6 mM, preferably >7 mM, more preferably 7.5 mM Mg$^{++}$, while PCR buffers typically comprise about 1.5 to 2.5 mM Mg$^{++}$.)

As used herein, the term "flap assay reagents" or "invasive cleavage assay reagents" refers to a collection of all reagents required for performing a flap assay or invasive cleavage assay on a substrate. As is known in the art, flap assays generally include oligonucleotides for forming an invasive cleavage structure, a flap endonuclease and, optionally, a FRET cassette or 5' hairpin FRET reporter.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "FRET system" refers to a pair or group of moieties that together act as donor-acceptor or donor-quencher partners for FRET-based analysis of molecules, e.g., flap oligonucleotides or assay reporter molecules. While embodiments of the technology are illustrated with a fluorophore in one particular position and a quencher or other FRET acceptor moiety in a particular second position, e.g., in a FRET assay reporter as illustrated in FIGS. 1-5, the illustrated embodiments provided as non-limiting examples of the technology. The moieties of a FRET system finding application in the technology are not limited to these placements and may, for example, be switched in position, may be positioned on different parts of the illustrated molecules, or may comprise additional donor or acceptor moieties that are the same or different.

As used herein, the term "reporting cleavage site" refers to a cleavage site that generates signal in a flap endonuclease assay. For example, flap oligonucleotides configured to use a FRET effect to indicate release of a 5' flap by a flap endonuclease may comprise fluorophore moiety and quencher moieties that are positioned to be separated by flap endonuclease cleavage when the flap oligonucleotide hybridizes to a target molecule. Cleavage between the fluorophore and quencher moieties separates the FRET system moieties and removes the quenching effect from the fluorophore such that successful cleavage is reported, i.e., is made detectable, by an increase in fluorescence from the fluorophore. Thus, a site between fluorophore and quencher moieties of a FRET system is a reporting cleavage site, while any site on that oligonucleotide that may be cleaved by an activity of a flap endonuclease but that is not between the FRET moieties would not be a reporting cleavage site. In preferred embodiments, a "reporting cleavage site" in a substrate structure used in an assay is a target cleavage site for the flap endonuclease used in the assay.

As used herein, the term "FRET cassette" refers to a hairpin oligonucleotide that contains a fluorophore moiety and a nearby quencher moiety that quenches the fluorophore. Hybridization of a cleaved flap (e.g., from cleavage of a target-specific probe in a PCR-flap assay assay) with a FRET cassette produces a secondary substrate for the flap endonuclease, e.g., a FEN-1 enzyme. Once this substrate is formed, the 5' fluorophore-containing base can be cleaved from the cassette by the flap endonuclease, thereby generating a fluorescence signal. In preferred embodiments, a FRET cassette comprises an unpaired 3' portion to which a cleavage product, e.g., a portion of a cleaved flap oligonucleotide, can hybridize to from an invasive cleavage structure cleavable by a FEN-1 endonuclease.

A nucleic acid "hairpin" as used herein refers to a region of a nucleic acid containing an intra-strand, base-paired stem closed at one end by a loop. In preferred embodiments, the loop comprises a plurality of unpaired nucleotides. A hairpin may be formed, e.g., when a nucleic acid strand comprises two portions that are sufficiently complementary to each other to form a plurality of base pairs, preferably consecutive base pairs, e.g., 2, 3, 4, 5, 6, 7, 8, 9, 10 or more consecutive base pairs. A 5' hairpin of a 5' hairpin FRET reporter, 5' hairpin flap oligonucleotide, or of 3-hairpin flap endonuclease substrate comprises at least two, preferably at least 3 consecutive base pairs in the stem of a 5' hairpin.

The terms "hairpin-forming region" and "hairpin-forming sequence" are used interchangeably herein and refer to a region of a nucleic acid strand that comprises self-complementary sequences that may base pair to form a double-stranded "stem" region, the strands of the stem optionally connected at one end by a loop sequence. A stem of a hairpin region generally comprises at least two consecutive base pairs, preferably standard Watson-Crick base pairs. A stem of a hairpin formed by the self-complementary sequences of a hairpin-forming region are not limited to any particular number of consecutive or non-consecutive base pairs. In some embodiments, a stem may comprise 3, 4, 5, 6, 7, . . . 10, 20, 30, . . . 50, 100, 150, or any integer in therebetween, or more, base pairs. In some embodiments, stems may comprise one or more base analogs and the hairpins may comprise one or more non-standard base pairs. In hairpin reporter molecules, e.g., FRET cassettes, 5' hairpin FRET reporter molecules, and single molecule substrates, different hairpins may have different preferred stem lengths. For example, a hairpin forming region that forms a downstream duplex in a flap cleavage substrate preferably comprises complementary sequences that may form 10 or more base pairs, preferable 10 or more consecutive base pairs, preferably Watson-Crick base pairs, for efficient cleavage by a flap endonuclease, while a stem region of a hairpin that provides an upstream duplex for a flap endonuclease may be substantially shorter, e.g., as few as 2 or 3 base pairs. (see, e.g., Kaiser M. W., et al. supra). In preferred embodiments, a hairpin-forming region forming a 5' hairpin is selected to form a number of base pairs in stem that represses cleavage at a target cleavage site under some conditions (e.g., below an assay reaction temperature) and does not repress cleavage at the target cleavage site under other conditions (e.g., at an assay reaction temperature). In some embodiments, hairpin stems may comprise mismatches, deletions, insertions, bulged nucleotides, side-stems (e.g., forming 3-way and 4-way junctions), etc. The loop end of a hairpin stem-loop may comprise a sequence of nucleotides, or may comprise a non-nucleotide connector, e.g., one or more abasic spacers or linkers, carbon chains, etc.

In some embodiments, a stabilizing loop, e.g., a DNA tetraloop (Antao et al., Nucl. Acids Res., 19:5901 [1991]) or triloop (Hiraro et al., Nuc. Acids Res., 22:576 [1994]) at the loop end of the stem may be used. For synthetic hairpin probes, such as FRET cassettes, 5' hairpin FRET reporters, and 5' hairpin test substrates, design elements for consideration in hairpin-forming regions include the length of region of self-complementarity, the stability of a hairpin or stem/loop structure as predicted by Watson-Crick base pairing, the presence of non-standard bases and base pairings, and the presence or absence of any particularly stable loop sequence (e.g., a tetraloop [Tinoco et al., supra], or a triloop [Hirao et al., supra]).

As used herein, the term "5' hairpin FRET reporter" refers to a type of FRET cassette that comprises a 5' hairpin-forming region upstream of a target cleavage site, and that comprises FRET labeling moieties that are separated upon cleavage of the reporter at the target cleavage site. In certain embodiments, a 5' hairpin FRET reporter comprises a region that can form a downstream duplex in an invasive cleavage structure. In preferred embodiments, a 5' hairpin FRET reporter further comprises a region that can hybridize to a 3' terminal portion of a nucleic acid strand to form an upstream duplex of an invasive cleavage structure, such that the 5' hairpin FRET reporter is cleavable at the target cleavage site under conditions in which cleavage is not repressed by a 5' hairpin, e.g., under conditions in which the 5' hairpin-forming region is not in a hairpin form. In particularly preferred embodiments, a 5' hairpin FRET reporter complexed with one or more additional nucleic acids to form an invasive cleavage structure is cleavable by Afu FEN-1 in a $Mg^{++}$ flap assay buffer under conditions in which cleavage is not repressed by a 5' hairpin. As used herein the term "5' hairpin test substrate," e.g., for a flap endonuclease, refers to a single strand of nucleic acid, preferably synthetic nucleic acid, that forms a structure cleavable with a flap endonuclease, preferably FEN-1 flap endonuclease, under certain conditions, and that contains a 5' hairpin-forming region. In preferred embodiments, a 5' hairpin test substrate forms an intramolecular structure that is not cleavable or is poorly cleavable by a FEN-1 endonuclease under conditions in which a 5' hairpin may be present (e.g., at a low temperature), and that is cleavable by the same endonuclease under conditions in which a 5' hairpin is less likely to be present (e.g., at higher temperature.) In preferred embodiments, a structure formed by a 5' hairpin test substrate is cleavable using Afu FEN-1 endonuclease under conditions that a maximally specific for invasive cleavage structures, e.g., in a buffer that comprises $Mg^{++}$ as essentially the only divalent cation in the reaction, and/or that is substantially free of $Mn^{++}$. Preferably, a 5' hairpin test substrate comprises sequences to form upstream and downstream duplexes of an invasive cleavage structure, and a 5' hairpin-forming region upstream of a target cleavage site, i.e., the test substrate of the technology can form 3 hairpins: an upstream duplex hairpin, a downstream duplex hairpin, and a 5' hairpin e.g., as illustrated in FIG. 8A. In some embodiments, a 5' hairpin test substrate comprises FRET labeling moieties that are separated upon cleavage of the test substrate at the target cleavage site. In preferred embodiments, the 5' hairpin test substrate is cleavable at the target cleavage site under conditions in which cleavage is not repressed by a 5' hairpin, e.g., under conditions in which the 5' hairpin-forming region is not in a hairpin form. In particularly preferred embodiments, a 5' hairpin test substrate is cleavable by Afu FEN-1 in a $Mg^{++}$ flap assay buffer under conditions in which cleavage is not repressed by a 5' hairpin.

As used herein, the term "primer annealing" refers to conditions that permit oligonucleotide primers to hybridize to template nucleic acid strands. Conditions for primer annealing vary with the length and sequence of the primer and are generally based upon the $T_m$ that is determined or calculated for the primer. For example, an annealing step in an amplification method that involves thermocycling involves reducing the temperature after a heat denaturation step to a temperature based on the $T_m$ of the primer sequence, for a time sufficient to permit such annealing.

As used herein, the term "amplifiable nucleic acid" is used in reference to nucleic acids that may be amplified by any amplification method. It is contemplated that "amplifiable nucleic acid" will usually comprise "sample template."

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "abundance of nucleic acid" refers to the amount of a particular target nucleic acid sequence present in a sample or aliquot. The amount is generally referred to in terms of mass (e.g., µg), mass per unit of volume (e.g., µg/µL); copy number (e.g., 1000 copies, 1 attomole), or copy number per unit of volume (e.g., 1000 copies per mL, 1 attomole per µL). Abundance of a nucleic acid can also be expressed as an amount relative to the amount of a standard of known concentration or copy number. Measurement of abundance of a nucleic acid may be on any basis understood by those of skill in the art as being a suitable quantitative representation of nucleic acid abundance, including physical density or the sample, optical density, refractive property, staining properties, or on the basis of the intensity of a detectable label, e.g. a fluorescent label.

The term "amplicon" or "amplified product" refers to a segment of nucleic acid, generally DNA, generated by an amplification process such as the PCR process. The terms are also used in reference to RNA segments produced by amplification methods that employ RNA polymerases, such as NASBA, TMA, etc.

The term "amplification plot" as used in reference to a thermal cycling amplification reaction refers to the plot of signal that is indicative of amplification, e.g., fluorescence signal, versus cycle number. When used in reference to a non-thermal cycling amplification method, an amplification plot generally refers to a plot of the accumulation of signal as a function of time.

The term "baseline" as used in reference to an amplification plot refers to the detected signal coming from assembled amplification reactions prior to incubation or, in the case of PCR, in the initial cycles, in which there is little change in signal.

The term "$C_t$" or "threshold cycle" as used herein in reference to real time detection during an amplification reaction that is thermal cycled refers to the fractional cycle number at which the detected signal (e.g., fluorescence) passes the fixed threshold.

The term "no template control" and "no target control" (or "NTC") as used herein in reference to a control reaction refers to a reaction or sample that does not contain template or target nucleic acid. It is used to verify amplification quality.

As used herein, the term "sample template" refers to nucleic acid originating from a sample that is analyzed for the presence of "target." In contrast, "background template" is used in reference to nucleic acid other than sample template that may or may not be present in a sample. The presence of background template is most often inadvertent. It may be the result of carryover, or it may be due to the presence of nucleic acid contaminants sought to be purified away from the sample. For example, nucleic acids from organisms other than those to be detected may be present as background in a test sample.

A sample "suspected of containing" a nucleic acid may contain or not contain the target nucleic acid molecule.

As used herein, the term "sample" is used in its broadest sense. For example, in some embodiments, it is meant to include a specimen or culture (e.g., microbiological culture), whereas in other embodiments, it is meant to include both biological and environmental samples (e.g., suspected of comprising a target sequence, gene or template). In some embodiments, a sample may include a specimen of synthetic origin. Samples may be unpurified or may be partially or completely purified or otherwise processed.

The present technology is not limited by the type of biological sample used or analyzed. The present technology is useful with a variety of biological samples including, but not limited to, tissue (e.g., organ (e.g., heart, liver, brain, lung, stomach, intestine, spleen, kidney, pancreas, and reproductive organs), glandular, skin, and muscle), cell (e.g., blood cell (e.g., lymphocyte or erythrocyte), muscle cell, tumor cell, and skin cell), gas, bodily fluid (e.g., blood or portion thereof, serum, plasma, urine, semen, saliva, etc.), or solid (e.g., stool) samples obtained from a human (e.g., adult, infant, or embryo) or animal (e.g., cattle, poultry, mouse, rat, dog, pig, cat, horse, and the like). In some embodiments, biological samples may be solid food and/or feed products and/or ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, pinnipeds, etc.

Biological samples also include biopsies and tissue sections (e.g., biopsy or section of tumor, growth, rash, infection, or paraffin-embedded sections), medical or hospital samples (e.g., including, but not limited to, blood samples, saliva, buccal swab, cerebrospinal fluid, pleural fluid, milk, colostrum, lymph, sputum, vomitus, bile, semen, oocytes, cervical cells, amniotic fluid, urine, stool, hair, and sweat), laboratory samples (e.g., subcellular fractions), and forensic samples (e.g., blood or tissue (e.g., spatter or residue), hair and skin cells containing nucleic acids), and archeological samples (e.g., fossilized organisms, tissue, or cells).

Environmental samples include, but are not limited to, environmental material such as surface matter, soil, water (e.g., freshwater or seawater), algae, lichens, geological samples, air containing materials containing nucleic acids, crystals, and industrial samples, as well as samples obtained from food and dairy processing instruments, apparatus, equipment, utensils, disposable and non-disposable items.

Samples may be prepared by any desired or suitable method. In some embodiments, nucleic acids are analyzed directly from bodily fluids, stool, or other samples using the methods described in U.S. Pat. No. 9,000,146, which is herein incorporated by reference in its entirety for all purposes.

The above described examples are not, however, to be construed as limiting the sample (e.g., suspected of comprising a target sequence, gene or template (e.g., the presence or absence of which can be determined using the compositions and methods of the present technology)) types applicable to the present technology.

The terms "nucleic acid sequence" and "nucleic acid molecule" as used herein refer to an oligonucleotide, nucleotide or polynucleotide, and fragments or portions thereof. The terms encompass sequences that include analogs of DNA and RNA nucleotides, including those listed above, and also including, but not limited to, 4-acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, and pyrazolo[3,4-d]pyrimidines such as guanine analogue 6 amino 1H-pyrazolo[3,4d]pyrimidin 4(5H) one (ppG or PPG, also Super G) and the adenine analogue 4 amino 1H-pyrazolo[3,4d]pyrimidine (ppA or PPA). The xanthine analogue 1H-pyrazolo[5,4d]pyrimidin 4(5H)-6(7H)-dione (ppX) can also be used. These base analogues, when present in an oligonucleotide, strengthen hybridization and improve mismatch discrimination. All tautomeric forms of naturally occurring bases, modified bases and base analogues may be included in the oligonucleotide conjugates of the technology. Other modified bases useful in the present technology include 6-amino-3-prop-1-ynyl-5-hydropyrazolo[3,4-d]pyrimidine-4-one, PPPG; 6-amino-3-(3-hydroxyprop-1-yny)1-5-hydropyrazolo[3,4-d]pyrimidine-4-one, HOPPPG; 6-amino-3-(3-aminoprop-1-ynyl)-5-hydropyrazolo[3,4-d]pyrimidine-4-one, NH2PPPG; 4-amino-3-(prop-1-ynyl)pyrazolo[3,4-d]pyrimidine, PPPA; 4-amino-3-(3-hydroxyprop-1-ynyl)pyrazolo[3,4-d]pyrimidine, HOPPPA; 4-amino-3-(3-aminoprop-1-ynyl)pyrazolo[3,4-d]pyrimidine, NH2 PPPA; 3-prop-1-ynylpyrazolo[3,4-d]pyrimidine-4,6-diamino, $(NH_2)_2$ PPPA; 2-(4,6-diaminopyrazolo[3,4-d]pyrimidin-3-yl)ethyn-1-ol, $(NH_2)_2$ PPPAOH; 3-(2-aminoethynyl)pyrazolo[3,4-d]pyrimidine-4,6-diamine, $(NH_2)_2$ PPPANH2; 5-prop-1-ynyl-1,3-dihydropyrimidine-2,4-dione, PU; 5-(3-hydroxyprop-1-ynyl)-1,3-dihydropyrimidine-2,4-dione, HOPU; 6-amino-5-prop-1-ynyl-3-dihydropyrimidine-2-one, PC; 6-amino-5-(3-hydroxyprop-1-yny)-1,3-dihydropyrimidine-2-one, HOPC; and 6-amino-5-(3-aminoprop-1-yny)-1,3-dihydropyrimidine-2-one, NH$_2$PC; 5-[4-amino-3-(3-methoxyprop-1-ynyl) pyrazol[3,4-d]pyrimidinyl]-2-(hydroxymethyl)oxolan-3-ol, CH3 OPPPA; 6-amino-1-[4-hydroxy-5-(hydroxymethyl) oxolan-2-yl]-3-(3-methoxyprop-1-ynyl)-5-hydropyrazolo [3,4-d]pyrimidin-4-one, CH3 OPPPG; 4, (4,6-Diamino-1H-pyrazolo[3,4-d]pyrimidin-3-yl)-but-3-yn-1-ol, Super A; 6-Amino-3-(4-hydroxy-but-1-ynyl)-1,5-dihydro-pyrazolo [3,4-d]pyrimidin-4-one; 5-(4-hydroxy-but-1-ynyl)-1H-pyrimidine-2,4-dione, Super T; 3-iodo-1H-pyrazolo[3,4-d]pyrimidine-4,6-diamine ((NH$_2$)$_2$PPAI); 3-bromo-1H-pyrazolo [3,4-d]pyrimidine-4,6-diamine ((NH$_2$)$_2$PPABr); 3-chloro-1H-pyrazolo[3,4-d]pyrimidine-4,6-diamine ((NH$_2$)$_2$ PPACl); 3-Iodo-1H-pyrazolo[3,4-d]pyrimidin-4-ylamine (PPAI); 3-Bromo-1H-pyrazolo[3,4-d]pyrimidin-4-ylamine (PPABr); and 3-chloro-1H-pyrazolo[3,4-d]pyrimidin-4-ylamine (PPACl). The term encompasses base analogs that provide alternative hydrogen bonding configurations (e.g., Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include modified forms of deoxyribonucleotides as well as ribonucleotides.

A nucleic acid sequence or molecule may be DNA or RNA, of either genomic or synthetic origin, that may be single or double stranded, and represent the sense or antisense strand. Thus, nucleic acid sequence may be dsDNA, ssDNA, mixed ssDNA, mixed dsDNA, dsDNA made into ssDNA (e.g., through melting, denaturing, helicases, etc.), A-, B-, or Z-DNA, triple-stranded DNA, RNA, ssRNA, dsRNA, mixed ss and dsRNA, dsRNA made into ssRNA (e.g., via melting, denaturing, helicases, etc.), messenger RNA (mRNA), ribosomal RNA (rRNA), transfer RNA (tRNA), catalytic RNA, snRNA, microRNA, or protein nucleic acid (PNA).

The present technology is not limited by the type or source of nucleic acid (e.g., sequence or molecule (e.g. target sequence and/or oligonucleotide)) utilized. For example, the nucleic acid sequence may be amplified or created sequence (e.g., amplification or creation of nucleic acid sequence via synthesis (e.g., polymerization (e.g., primer extension (e.g., RNA-DNA hybrid primer technology)) and reverse transcription (e.g., of RNA into DNA)) and/or amplification (e.g., polymerase chain reaction (PCR), rolling circle amplification (RCA), nucleic acid sequence based amplification (NASBA), transcription mediated amplification (TMA), ligase chain reaction (LCR), cycling probe technology, Q-beta replicase, strand displacement amplification (SDA), branched-DNA signal amplification (bDNA), hybrid capture, and helicase dependent amplification).

The terms "nucleotide" and "base" are used interchangeably when used in reference to a nucleic acid sequence, unless indicated otherwise herein. A "nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, LO), all herein incorporated by reference in their entireties.

The term "oligonucleotide" as used herein is defined as a molecule comprising two or more nucleotides (e.g., deoxyribonucleotides or ribonucleotides), preferably at least 5 nucleotides, more preferably at least about 10-15 nucleotides and more preferably at least about 15 to 30 nucleotides, or longer (e.g., oligonucleotides are typically less than 200 residues long (e.g., between 15 and 100 nucleotides), however, as used herein, the term is also intended to encompass longer polynucleotide chains). The exact size will depend on many factors, which in turn depend on the ultimate function or use of the oligonucleotide. Oligonucleotides are often referred to by their length. For example, a 24-residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes. Oligonucleotides may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' terminus" or 5' end if its 5' phosphate is not linked to the 3' oxygen of a mononucleotide pentose ring and as the "3' terminus or 3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. As distinct from the 3' and 5' ends of a nucleic acid molecule, the 3' and 5' ends of a nucleic acid sequence need not be at the 3' and 5' termini of the molecule strand. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

As used herein, "base pairing rules" refers to the rules for the pairing of nucleotide bases established by Watson and Crick. In standard Watson-Crick geometry, large purines (A and G bases) base pair with a small pyrimidine bases (T and C), with A pairing with T (or U) and G pairing with C, so that the A-T base pair is essentially the same size as the G-C base pair. This means that the rungs of a DNA ladder, formed from either A-T (or A-U) or G-C base pairs, all have the same length across the helix. Under the standard Watson-Crick rules for base pairing, A-T and A-U base pairs form two hydrogen bonds between the base moieties, and G-C base pairs form three hydrogen bonds.

Nucleotides may pair in non-standard ways, such as in "wobble" base pairing, in which one or more hydrogen bonds are formed but the geometry of the base pair does not fit within the standard Watson-Crick geometry. Among the most common of wobble base pairs are G-T (or U) base pairing, in which a single hydrogen bond is formed between G and T (or G and U). Non-Watson-Crick base pairing also include base pairs formed by inosine (I) with C, T, or A, purine base pairs A-G (or I), A-A, and G-C, and the reverse Watson-Crick base pair A-T, in which the T ring is rotated 180° from the normal Watson-Crick pair. See, e.g., Hyone-Myong Eun, *Enzymology Primer for Recombinant DNA Technology*, Academic Press, (1996).

As used herein, "standard base pair/base pairing" refers to base pairs having standard Watson-Crick geometry, and encompassing A-T, A-U, and G-C base pairs. The term encompasses base pairing of modified analogs of these nucleotides in which the modification (e.g., an attached dye or other moiety) does not substantially alter the hydrogen bonding between the bases (e.g., the number, positions, or acceptor/donor pairs of the hydrogen bonds.) As used herein, "non-standard base pair/base pairing" refers to pairing between nucleotides e.g., natural nucleotides, nucleotide analogs, that does not fall within standard base pairing having standard Watson-Crick geometry.

As used herein, the terms "complementary" or "complementarity" are used in reference to polynucleotides (e.g., a sequence of two or more nucleotides (e.g., an oligonucleotide or a target nucleic acid)) related by the base-pairing rules. For example, the sequence "5'-A-G-T-3'," is complementary to the sequence "3'-T-C-A-5'." Complementarity may be "partial," in which only some of the nucleic acid bases are matched according to the base pairing rules. Or, there may be "complete" or "total" complementarity between the nucleic acid bases. The degree of complementarity between nucleic acid strands has significant effects on the efficiency and strength of hybridization between nucleic acid strands. This is of particular importance in amplification reactions, as well as detection methods that depend upon the association of two or more nucleic acid strands. Either term may also be used in reference to individual nucleotides, especially within the context of polynucleotides. For example, a particular nucleotide within an oligonucleotide may be noted for its complementarity, or lack thereof, to a nucleotide within another nucleic acid sequence (e.g., a target sequence), in contrast or comparison to the complementarity between the rest of the oligonucleotide and the nucleic acid sequence.

The complement of a nucleic acid sequence as used herein refers to an oligonucleotide which, when aligned with the nucleic acid sequence such that the 5' end of one sequence is paired with the 3' end of the other, is in "antiparallel association." Nucleotide analogs, as discussed above, may be included in the nucleic acids of the present technology and include, for example, inosine, 7-deazaguanine, iso-C, and iso-G. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. As used herein, the term "label" refers to any moiety (e.g., chemical species) that can be detected or can lead to a detectable response. In some preferred embodiments, detection of a label provides quantifiable information. Labels can be any known detectable moiety, such as, for example, a radioactive label (e.g., radionuclides), a ligand (e.g., biotin or avidin), a chromophore (e.g., a dye or particle that imparts a detectable color), a hapten (e.g., digoxygenin), a mass label, latex beads, metal particles, a paramagnetic label, a luminescent compound (e.g., bioluminescent, phosphorescent or chemiluminescent labels) or a fluorescent compound.

A label may also comprise a phosphor particle for detection. In particularly preferred embodiments, the phosphor particle is an up-converting phosphor particle (see, e.g., Ostermayer, F. W. Preparation and properties of infrared-to-visible conversion phosphors. Metall. Trans. 752, 747-755 [1971]). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. While the present invention is not limited to any particular mechanism, in some embodiments the UPT up-converts infrared light to visible light by multi-photon absorption and subsequent emission of dopant-dependent phosphorescence. See, e.g., U.S. Pat. No. 6,399,397, Issued Jun. 4, 2002 to Zarling, et al.; van De Rijke, et al., Nature Biotechnol. 19(3):273-6

[2001]; Corstjens, et al., IEE Proc. Nanobiotechnol. 152(2): 64 [2005], each incorporated by reference herein in its entirety.

As used herein, the term "distinct" in reference to signals, e.g., from different labels, refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

A label may be joined, directly or indirectly, to an oligonucleotide or other biological molecule. Direct labeling can occur through bonds or interactions that link the label to the oligonucleotide, including covalent bonds or non-covalent interactions such as hydrogen bonding, hydrophobic and ionic interactions, or through formation of chelates or coordination complexes. Indirect labeling can occur through use of a bridging moiety or "linker", such as an antibody or additional oligonucleotide(s), which is/are either directly or indirectly labeled.

Labels can be used alone or in combination with moieties that can suppress (e.g., quench), excite, or transfer (e.g., shift) emission spectra (e.g., fluorescence resonance energy transfer (FRET)) of a label (e.g., a luminescent label).

A "polymerase" is an enzyme generally for joining 3'-OH 5'-triphosphate nucleotides, oligomers, and their analogs. Polymerases include, but are not limited to, template-dependent DNA-dependent DNA polymerases, DNA-dependent RNA polymerases, RNA-dependent DNA polymerases, and RNA-dependent RNA polymerases. Polymerases include but are not limited to T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), Bst DNA Polymerase Large Fragment, Stoeffel Fragment, 9° N DNA Polymerase, Pfu DNA Polymerase, Tfl DNA Polymerase, RepliPHI Phi29 Polymerase, Tli DNA polymerase, eukaryotic DNA polymerase beta, telomerase, Therminator polymerase (New England Biolabs), KOD HiFi DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in US 2007/0048748, U.S. Pat. Nos. 6,329,178; 6,602,695; and 6,395,524 (incorporated by reference). These polymerases include wild-type, mutant isoforms, and genetically engineered variants.

A "DNA polymerase" is a polymerase that produces DNA from deoxynucleotide monomers (dNTPs). "Eubacterial DNA polymerase" as used herein refers to the Pol A type DNA polymerases (repair polymerases) from Eubacteria, including but not limited to DNA Polymerase I from *E. coli*, Taq DNA polymerase from *Thermus aquaticus* and DNA Pol I enzymes from other members of genus *Thermus*, and other eubacterial species etc.

As used herein, the term "target," as used in reference to a nucleic acid strand or site on a nucleic acid strand, refers to a nucleic acid species or nucleic acid sequence or structure to be detected or characterized.

Accordingly, as used herein, "non-target", e.g., as it is used to describe a nucleic acid such as a DNA, refers to nucleic acid that may be present in a reaction, but that is not the subject of detection or characterization by the reaction.

In some embodiments, non-target nucleic acid may refer to nucleic acid present in a sample that does not, e.g., contain a target sequence, while in some embodiments, non-target may refer to exogenous nucleic acid, i.e., nucleic acid that does not originate from a sample containing or suspected of containing a target nucleic acid, and that is added to a reaction, e.g., to normalize the activity of an enzyme (e.g., polymerase) to reduce variability in the performance of the enzyme in the reaction.

As used herein, the term "amplification reagents" refers to those reagents (deoxyribonucleoside triphosphates, buffer, etc.), needed for amplification except for primers, nucleic acid template, and the amplification enzyme. Typically, amplification reagents along with other reaction components are placed and contained in a reaction vessel.

As used herein, the term "control" when used in reference to nucleic acid detection or analysis refers to a nucleic acid having known features (e.g., known sequence, known copy-number per cell), for use in comparison to an experimental target (e.g., a nucleic acid of unknown concentration). A control may be an endogenous, preferably invariant gene against which a test or target nucleic acid in an assay can be normalized. Such normalizing controls for sample-to-sample variations that may occur in, for example, sample processing, assay efficiency, etc., and allows accurate sample-to-sample data comparison. Controls may also be external. For example, in quantitative assays such as qPCR, QuARTS, etc., a "calibrator" or "calibration control" is a nucleic acid of known sequence, e.g., having the same sequence as a portion of an experimental target nucleic acid, and a known concentration or series of concentrations (e.g., a serially diluted control target for generation of calibration curved in quantitative PCR). Typically, calibration controls are analyzed using the same reagents and reaction conditions as are used on an experimental DNA. In certain embodiments, the measurement of the calibrators is done at the same time, e.g., in the same thermal cycler, as the experimental assay. In preferred embodiments, multiple calibrators may be included in a single plasmid, such that the different calibrator sequences are easily provided in equimolar amounts. In particularly preferred embodiments, plasmid calibrators are digested, e.g., with one or more restriction enzymes, to release calibrator portion from the plasmid vector. See, e.g., WO 2015/066695, which is included herein by reference.

As used herein the term "fish DNA" refers to bulk (e.g., genomic) DNA isolated from fish, e.g., as described in U.S. Pat. No. 9,212,392. Bulk purified fish DNA is commercially available, e.g., provided in the form of cod and/or herring sperm DNA (Roche Applied Science, Mannheim, Germany) or salmon DNA (USB/Affymetrix). "Fish DNA" is distinct from any particular gene from a fish that is in isolated form, e.g., that has been separately synthesized or that has been separated from the other DNA of the fish genome.

As used herein, the term "kit" refers to any delivery system for delivering materials. In the context of nucleic acid purification systems and reaction assays, such delivery systems include systems that allow for the storage, transport, or delivery of reagents and devices (e.g., chaotropic salts, particles, buffers, denaturants, oligonucleotides, filters etc. in the appropriate containers) and/or supporting materials (e.g., sample processing or sample storage vessels, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain materials for sample collection and a buffer, while a second container contains capture oligonucleotides and denaturant. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, online (e.g., at a website or web address) on recordable media (e.g., diskette, CD, DVD, flash drive, etc.). In some embodiments, instructions direct a user to an online location, e.g., a website for viewing, hearing, and/or downloading instructions. In some embodiments, instructions or other information are provided as an application ("app"), e.g., for a computer or for a mobile device, such as a smart phone.

DESCRIPTION OF THE DRAWINGS

These and other features, aspects, and advantages of the present technology will become better understood with regard to the following drawings:

FIGS. 1A, 1B, and 1C provide schematic diagrams of invasive cleavage structures formed from three nucleic acid strands, two nucleic acid strands, or one nucleic acid strand, respectively.

FIGS. 3A-3D illustrate three 5' hairpin FRET reporter molecules. FIG. 3A shows the linear sequences for 5' hairpin FRET reporter molecules 1, 2, and 3, and schematic representations of secondary structures showing a 5' hairpin on each of the 5' hairpin FRET reporter molecules are shown in FIGS. 3B, 3C, and 3D. The different stems used in the 5' portion of 5' hairpin FRET reporter molecules 1, 2, and 3 result in different calculated melting temperatures for these portions of the reporter molecules.

FIGS. 13A and 13B illustrate titration of a reference material (e.g., a 5' hairpin test substrate) showing a differential response that results in a linear standard curve. This standard curve provides a means for determining relative performance of an unknown lot of enzyme. The rate of fluorescence increased over time (log[RFU/s]) for the linear portion of the reaction is graphed vs. enzyme concentration (log[FEN-1 (nM)]).

FIG. 14A illustrates an invasive cleavage structure formed on a target strand by hybridization of a probe oligonucleotide having a 5' hairpin-forming region and an upstream invasive oligonucleotide. At flap assay reaction temperatures, typically above the calculated melting temperature of the 5' hairpin, flap endonuclease cleavage at the target cleavage site is not suppressed, and cleavage can occur to release the 5' flap arm from the probe oligonucleotide. The released flap can form invasive cleavage structures with both standard FRET cassette and 5' hairpin FRET reported molecules, as illustrated in FIGS. 14B and 14C, respectively.

FIGS. 14B and 14C are schematic diagrams invasive cleavage structures formed with a released flap oligonucleotide either a standard FRET cassette (FIG. 14B) or a 5' hairpin FRET reporter molecule (FIG. 14C).

DETAILED DESCRIPTION OF THE INVENTION

The technology relates to structures cleavable by flap endonucleases. In particular, the technology relates to the formation of nucleic acid structures that can be manipulated, e.g., by changes in temperature, to modulate or suppress cleavage by flap endonucleases at a reporting cleavage site.

One aspect of designing nucleic acid detection assays is selecting reaction components and conditions that produce a minimum amount of background signal when a target analyte is not present, and that produce a distinctive reporting signal in the presence of the target analyte. In flap endonuclease assays, an aspect of signal generation is specific cleavage of flap oligonucleotides and of reporter molecules such FRET cassettes. Thus, an aspect of minimizing background in flap endonuclease assays is the use of reaction temperatures that are high enough that hybridization between nucleic acids from a test sample and the detection oligonucleotides of the assay (e.g., primers, flap oligonucleotides) is very specific. Typically, thermostable enzymes are used for such assays so that the assay reactions can be performed at reaction temperatures that minimize or eliminate non-specific binding of the assay oligonucleotides.

Assay reactions mixtures for high-temperature assays such as PCR and PCR-flap endonuclease assays are often assembled at temperatures well below the final reaction temperature, e.g., at room temperature or on ice. At these lower temperatures, cleavage of reporter oligonucleotides may occur in a non-specific fashion, e.g., by errant hybridization under the less stringent conditions.

In one aspect, the technology provides modified oligonucleotide substrates that repress flap endonuclease cleavage at a target or reporting cleavage site at low temperatures but that permit cleavage at the reporting cleavage site at a selected assay reaction temperature or range of temperatures. In some embodiments, a modified assay oligonucleotide, e.g., a flap oligonucleotide or FRET assay reporter, comprises a 5' flap region that includes a structure or moiety that suppresses cleavage at the reporting cleavage site at a lower temperature, but that loses the structure or moiety at the temperature at which the assay is performed, such that cleavage at the reporting cleavage site can occur. In preferred embodiments, the modified assay oligonucleotide comprises a 5' hairpin.

Figures 1A, 1B, 1C:
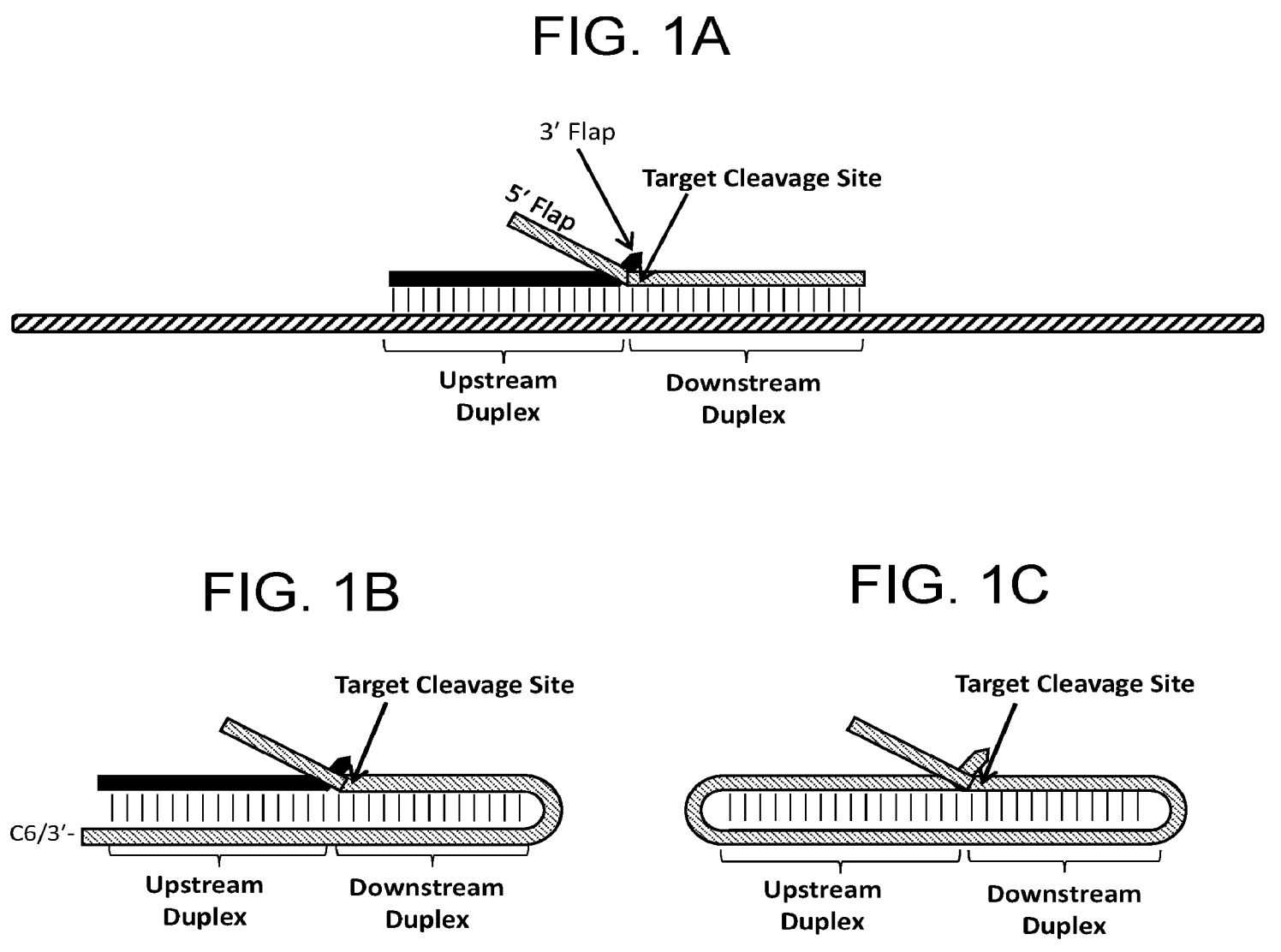
Figure 1D:
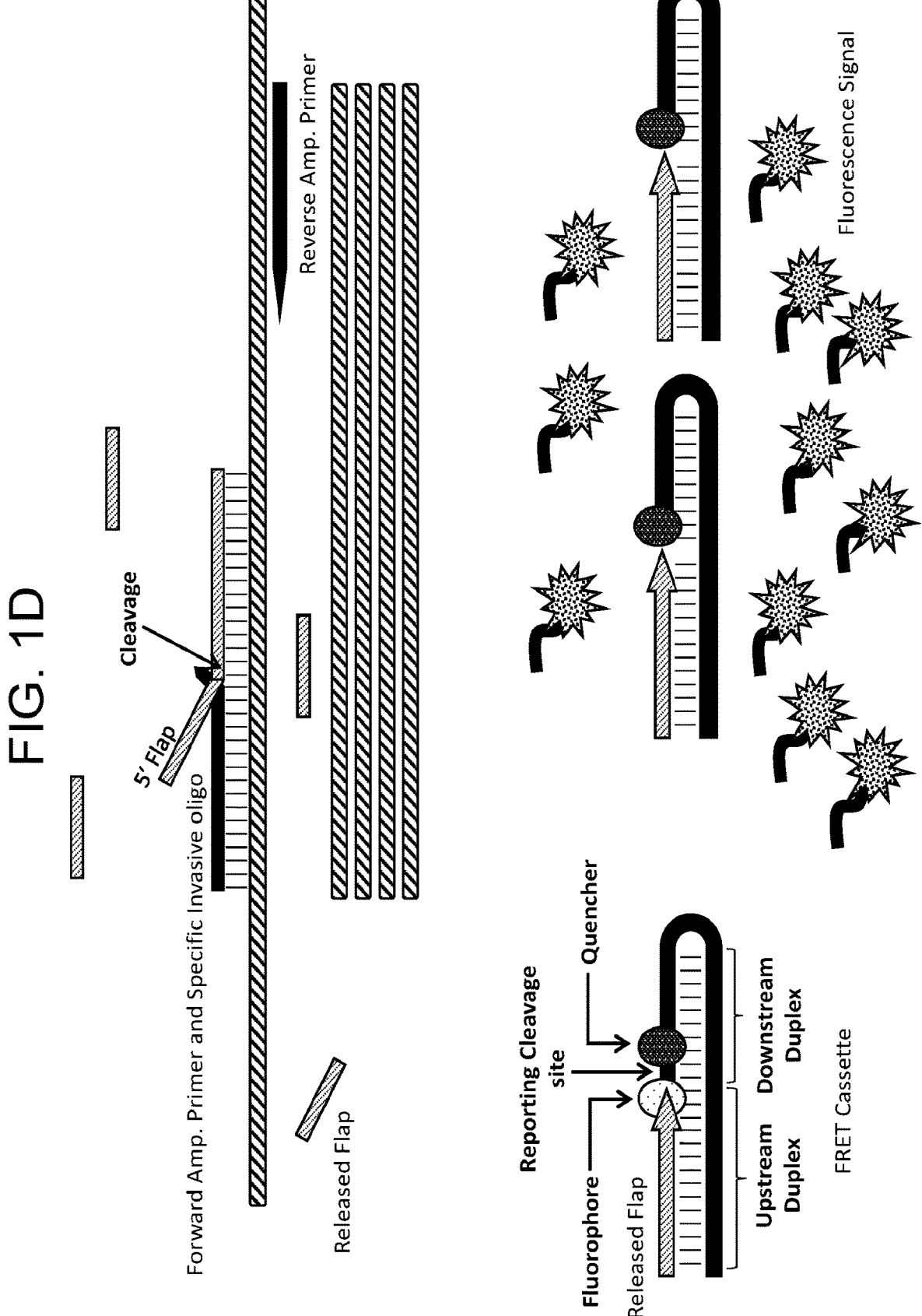
FIG. 1D provides a schematic diagram of a combined PCR-invasive cleavage assay ("PCR-flap assay"), e.g., a QuARTS assay, comprising a FRET cassette reporter oligonucleotide

In some embodiments, the technology find use in flap endonuclease assays, including, e.g., PCR-flap assays such as the QuARTS assays described in U.S. Pat. Nos. 8,361,720; 8,715,937; and 8,916,344, and the amplification assays of U.S. Pat. No. 9,096,893. See, e.g., FIG. 1, which provides a schematic diagram of an embodiment of a PCR-flap assay. As shown, a target-specific probe is cleaved by a flap endonuclease to release a 5' flap during amplification of a region of a target strand. In the secondary reaction, released 5' flap serves as an invasive oligonucleotide on a fluorescence resonance energy transfer (FRET) cassette to again create the structure recognized by the flap endonuclease. When the fluorophore and quencher on a single FRET cassette are separated by cleavage, a detectable fluorescent signal above background fluorescence is produced. Consequently, cleavage of this second structure results in an increase in fluorescence, indicating the presence of the target nucleic acid. In embodiments in which multiple different targets are to be detected, the FRET cassettes may have a distinct label (e.g. resolvable by difference in emission or excitation wavelengths, or resolvable by time-resolved fluorescence detection) for each allele or locus to be detected, such that the different alleles or loci can be detected in a single reaction. In such embodiments, the flap assay oligonucleotides for multiple target sequences may be combined in a single reaction mixture, allowing comparison of the signals from each allele or locus in the same sample.

The technology herein provides modified substrates for flap endonucleases. In particular embodiments, assay oligonucleotides, e.g., a flap oligonucleotide or the FRET reporter comprise a hairpin structure, preferably a DNA hairpin, in a 5' flap of the oligonucleotide to be cleaved in a flap assay reaction.

Figure 2:
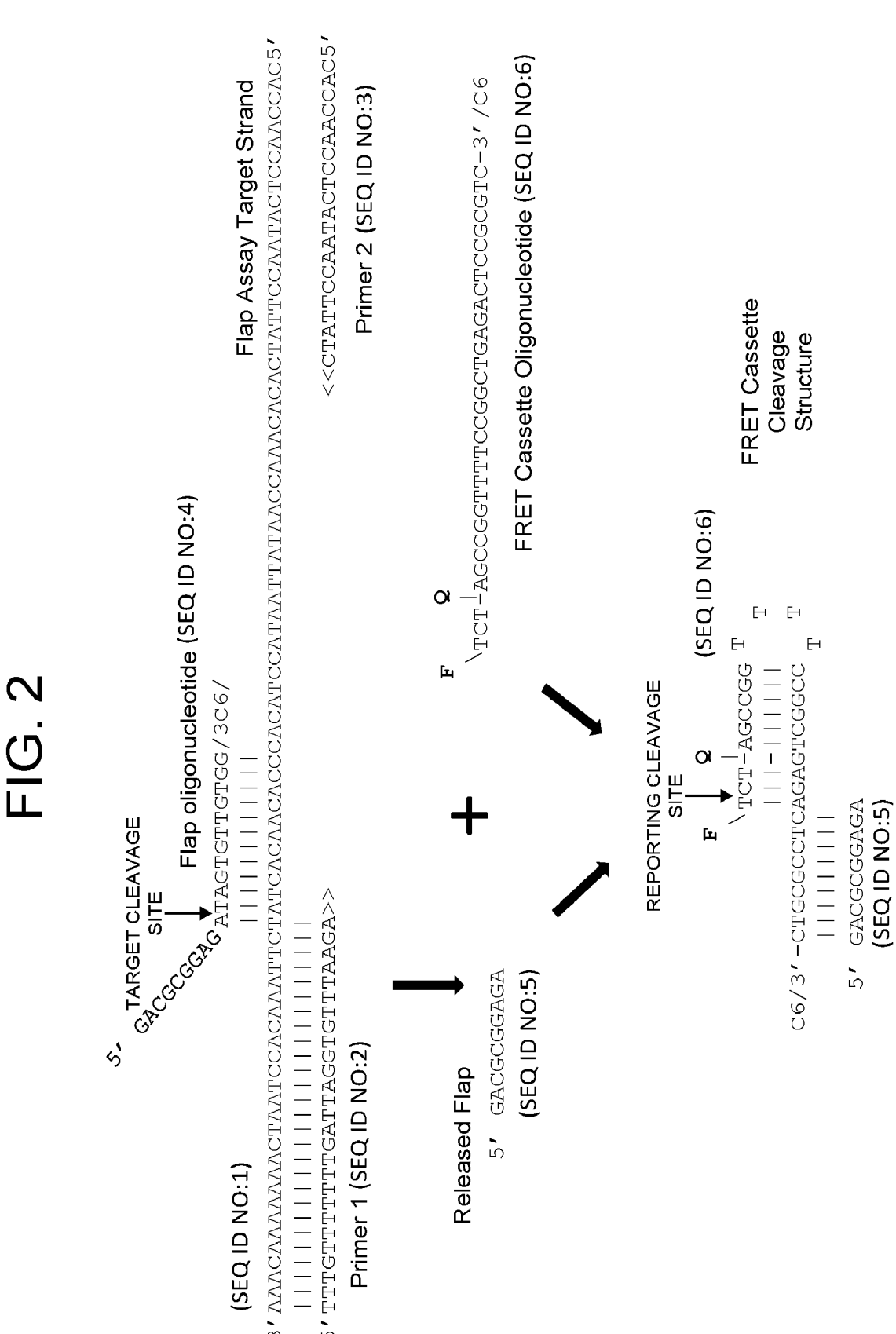
FIG. 2 shows nucleic acid sequences and schematic structures for an exemplary PCR-flap assay in which a flap is released by cleavage of a flap oligonucleotide, and the flap hybridizes to a 3' region of a FRET cassette oligonucleotide to form a second cleavage structure. Cleavage of the flap-FRET cassette complex separates a fluorophore from a quencher moiety and results in an increase in detectable fluorescence from the fluorophore.

The present technology is readily contrasted from a standard FRET assay reporter by considering the number of hairpins present, as a standard FRET cassette generally contains a single hairpin (see, e.g., FIG. 2), while the 5' hairpin molecules of the present technology generally comprise two or three hairpins.

| Structure | Downstream duplex | 5' hairpin | Upstream duplex (Intrinsic or Foldback) |
|---|---|---|---|
| Standard FRET cassette | X | | |
| 5' hairpin FRET assay reporter | X | X | |
| 5' hairpin test substrate | X | X | X |

While the technology is discussed herein by reference to embodiments in which the 5' hairpin-containing molecules are labeled with a FRET system, the technology is not limited to such embodiments. Applications of the technology to unlabeled oligonucleotides and structures and to oligonucleotides and structures using different types of labels are also contemplated and are within the scope of this technology.

Figure 4A:
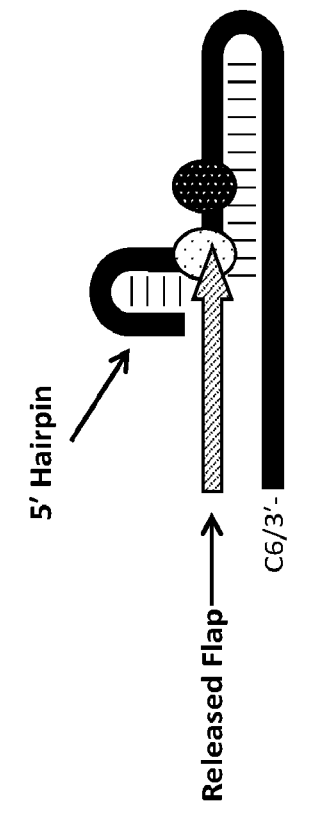
FIGS. 4A-4C provide schematic representations of 5' hairpin FRET assay reporter molecules in cleavable and suppressed cleavage configurations. While not limiting the technology to any particular mechanism of action, a 5' hairpin may form at low temperatures, thereby suppressing flap endonuclease cleavage at the reporting cleavage site between the fluorophore and quencher moieties when an assay reaction mixture is not at a preferred reaction temperature (as shown in FIGS. 4A-4B). At flap assay reaction temperatures, typically above the calculated melting temperature of the 5' hairpin, flap endonuclease cleavage at the reporting cleavage site is not suppressed, and cleavage can occur to release the fluorophore from proximity to the quencher, resulting in an increase in fluorescence signal from the fluorophore (FIG. 4C).
Figure 4B:
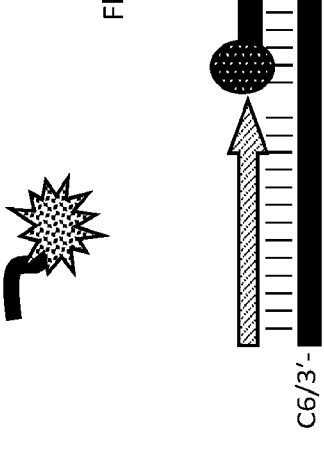
Figure 4C:
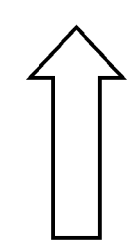
Figure 4C:
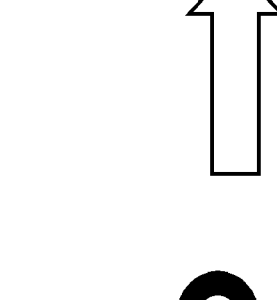
Figure 4C:
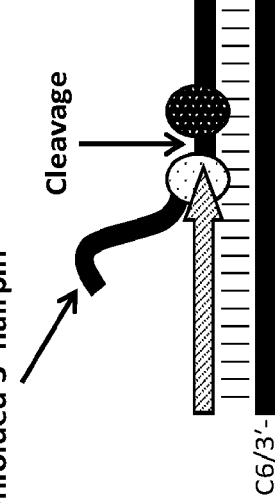
Figure 5:
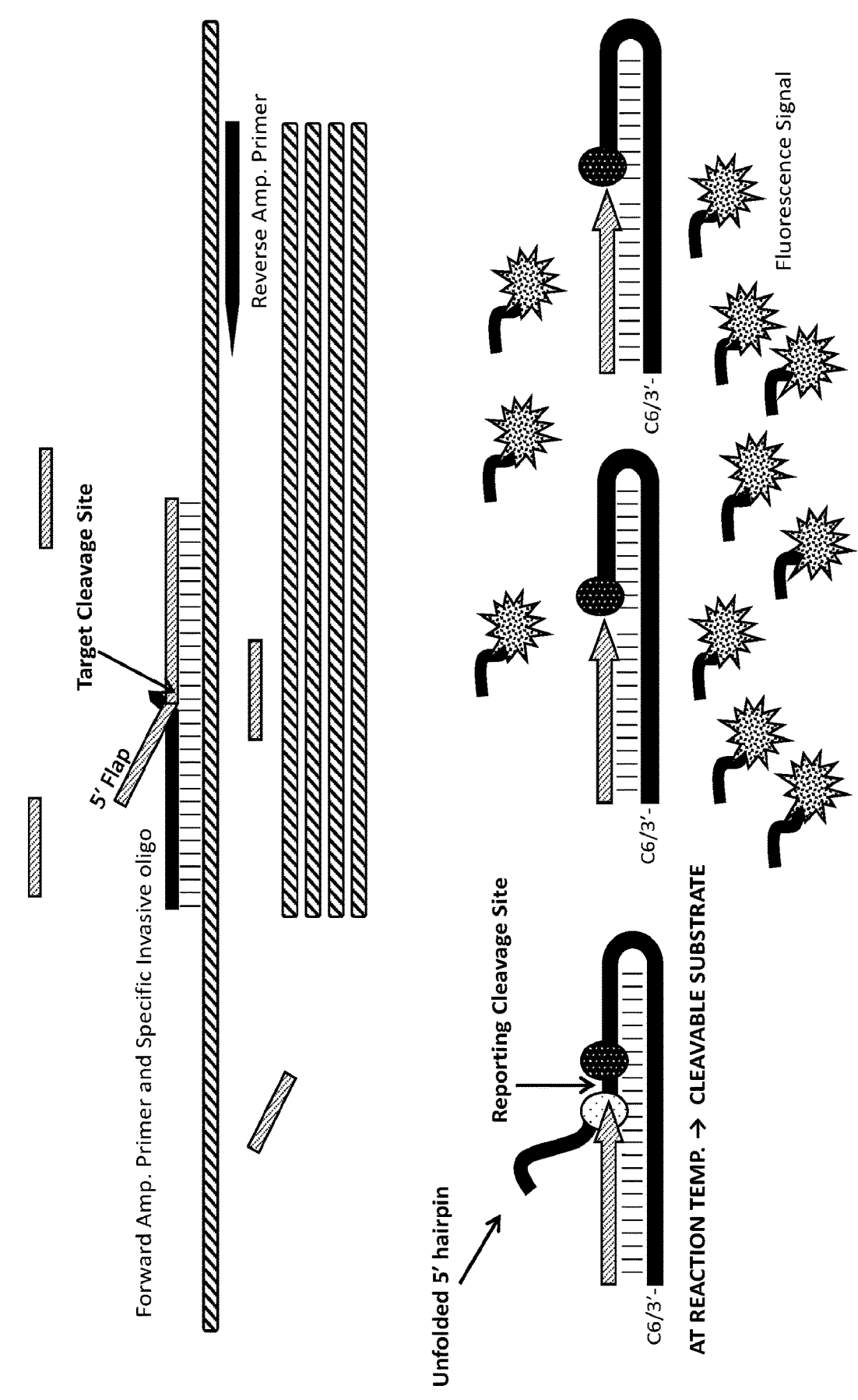
FIG. 5 provides a schematic diagram of a PCR-flap assay, e.g., a QuARTS assay, incorporating a 5' hairpin FRET assay reporter.

During development of the technology, it has been observed that the presence of a 5' hairpin improves invasive cleavage chemistry by reducing background cleavage. The technology can be incorporated into flap cleavage substrates, e.g., into a FRET cassette structure, to improve signal-to-noise separation in flap assay reactions, including PCR-flap assay reactions. A FRET cassette modified to have a 5' hairpin typically comprises two hairpins: the 5' hairpin that modulates cleavage at the reporting cleavage site and the hairpin that forms the downstream duplex that is characteristic of an invasive cleavage structure, as is shown schematically in FIG. 4A. For convenience, such a modified FRET cassette may be referred to as a "5' hairpin FRET reporter."

The 5' hairpin FRET reporter contains a sequence in a 5' flap calculated to form a hairpin that has a melting temperature that is lower than the reaction incubation temperature. When this 5' hairpin FRET reporter is mixed with the flap endonuclease enzyme at room temperature, cleavage is limited. While the technology is not limited to any particular mechanism of action, the data indicate that as the incubation temperature of the reaction increases beyond the melting point of the repressive hairpin, the hairpin melts, providing a single-stranded 5' arm upon which a FEN enzyme can thread to access a reporting cleavage site between the moieties of the FRET labeling system. Thus, when the melting temperature of the repressive arm is reached or surpassed, the flap endonuclease can cleave the reporter molecule to separate the fluorophore from the portion of the substrate containing the quencher, resulting in a measurable increase in fluorescence signal.

Figure 8A:
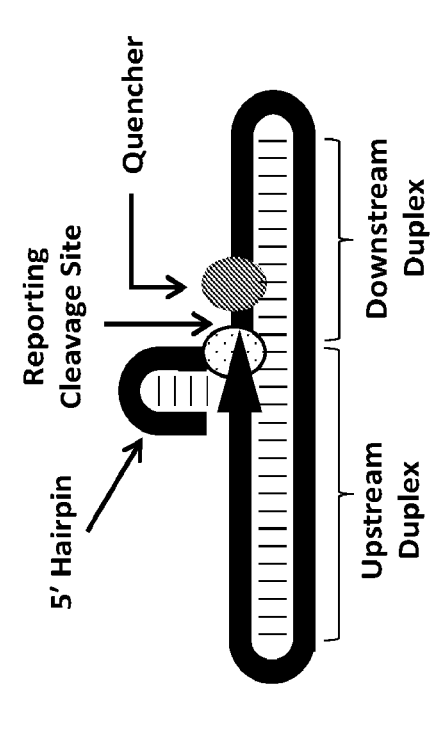
FIGS. 8A and 8B provide schematic diagrams of a 5' hairpin test substrate for flap endonucleases. In addition to a 5' hairpin-forming region and a downstream duplex hairpin-forming region, the test substrate includes a 3' hairpin-forming region configured to form an upstream duplex, to position the 3' end of the substrate oligonucleotide to act as an invasive oligonucleotide in an invasive cleavage structure.

The technology also finds use as part of an all-in-one test substrate comprising three hairpins that is useful for, e.g., characterizing flap endonuclease activities. FIG. 8A provides a schematic diagram of such a 3-hairpin test substrate. In preferred embodiments, a 3-hairpin substrate comprises a FRET labeling system in which a fluorophore and quencher are separable by flap endonuclease cleavage at a reporting cleavage site. As described above for flap endonuclease assays, when this 5' hairpin-containing substrate is mixed with the flap endonuclease enzyme at low temperature, e.g., at room temperature, cleavage is suppressed. Cleavage can be initiated by elevation of the temperature of the reaction mixture. While not limiting the technology to any particular mechanism of action, the 5' hairpin of the test substrate is calculated to melt at elevated reaction temperatures, such that the reporting cleavage site is made accessible to the flap endonuclease and the test substrate is cleaved at the reporting cleavage site. The 5' hairpin test substrate thus permits precise initiation of cleavage assay reactions. Use of a FRET labeling system has a further advantage of permitting real-time detection of cleavage of the test substrate as it occurs in the reaction. In combination, the features of the 3-hairpin test substrate permit precise characterization of the enzyme's activity.

The technology also finds application in synchronizing initiation of multiple assays, e.g., in different reaction vessels or in different wells of a multi-well assay plate. In such embodiments, the reactions mixtures may be assembled at different times and may be initiated by elevating the temperature in all vessels essentially simultaneously. Such synchronized reaction initiation by temperature shift is useful, for example, when the process of pipetting of assay reagents makes simultaneous mixing of reagents for multiple different reaction mixtures impractical or impossible.

In some embodiments, different 5' hairpin structures are used to provide different assay start times. For example, 5' hairpin FRET reporters may be configured to contain 5' hairpins that melt at different temperatures. Using FRET reporters with 5' repressive hairpins that melt at 40° C., 50° C., and 60° C., a set of reactions may be assembled at a temperature below 40° C., then the different reactions may be initiated at will, by elevation of the temperature to 40° C., 50° C., then 60° C., at times defined to suit the needs of a particular experiment.

In some embodiments, 5' hairpin modulation of cleavage activity is used to adjust cleavage rates for assays that exhibit different reaction rates. For example, use of different FRET labeling systems (e.g., different fluorophore-quencher combinations) may change cleavage activity exhibited by a flap endonuclease on different FRET reporters that otherwise have the same primary sequence and predicted secondary structure. It is contemplated that different 5' hairpin modifications (e.g., hairpins having different lengths or stabilities) find use in normalizing rates of cleavage among different FRET reporters, e.g., FRET reporters having different fluorophores. This embodiment finds application, for example, in multiplexed assays in which multiple different dyes are used, and wherein it may be desirable for all FRET reporters to be cleaved at approximately the same rate.

Characterizing Flap Endonucleases

The technology also finds application in other types of assays, e.g., assays for characterizing flap endonuclease activities. Model nucleic acid structures composed of one or more oligonucleotides, typically synthetic oligonucleotides, may be used in assays designed to detect or measure flap endonuclease activity, e.g., in enzymes suspected of having such activity (e.g., DNA polymerases, repair nucleases) or in organisms suspected of producing such enzymes, and to measure flap endonuclease activity, e.g., under different assay conditions. For example, various synthetic flap structures have been used to characterize the activities and structure specificity of recombinant FEN-1 endonucleases (see, e.g., U.S. Pat. No. 7,122,364 to Lyamichev, et al., and Kaiser M. W., et al. J. Biol. Chem., 274:21387 (1999), each of which is incorporated herein by reference). The structures tested by Lyamichev and Kaiser did not comprise a 5' hairpin structure of the present technology.

Figure 8B:
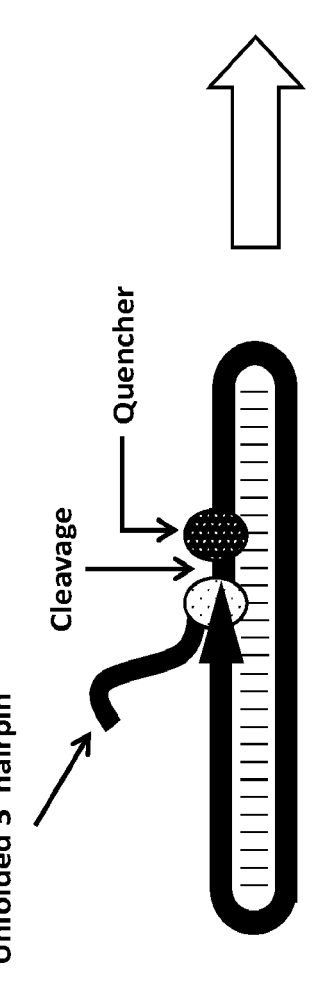

The technology herein provides a 3-hairpin substrate comprising an upstream duplex and a downstream duplex of an invasive cleavage structure, as shown in FIG. 8A, that finds use in characterizing the activities of flap endonucleases. While not limiting the technology to any particular mechanism of action, it is observed that the presence of a 5' hairpin represses invasive cleavage at the preferred site in the downstream duplex, which is indicated as the reporting cleavage site in FIG. 8A. As the incubation temperature of the reaction increases and surpasses the calculated melting temperature of the repressive 5' hairpin, the preferred structure for flap endonuclease cleavage is formed and the cleavage reaction is initiated (see FIG. 8B).

When a FRET labeling system is used, cleavage at the target cleavage site separates a fluorophore from a quencher, resulting in an increase in fluorescence. This signal can be monitored in real-time and corresponds to flap endonuclease cleavage activity in the reaction.

In some embodiments, 5' hairpin reporters and test substrates may include a 5' hairpin containing base analogs, spacers, (e.g., a 9-carbon spacer), and/or base analogs (e.g., non-standard bases, abasic sugars or linkers, etc.). In some embodiments, a 5' arm may be configured to make use of an alternative means of blocking flap endonuclease access to a target cleavage site. For example, two-molecule approach in which a short oligonucleotide is annealed to a single stranded 5'-arm is contemplated, or the 5' arm may be conjugated to a blocking moiety in a thermolabile manner, in which the conjugated blocker releases or is otherwise rendered neutral at elevated temperature.

EXPERIMENTAL EXAMPLES

The QuARTS and LQAS/TELQAS flap assay technologies combine a polymerase-based target DNA amplification process with an invasive cleavage-based signal amplification process. The QuARTS technology is described, e.g., in U.S. Pat. Nos. 8,361,720; 8,715,937; 8,916,344; and 9,212,392, and a flap assay using probe oligonucleotides having a longer target-specific region (Long probe Quantitative Amplified Signal, "LQAS") is described in U.S. Pat. No. 10,648,025, each of which is incorporated herein by reference in its entirety for all purposes. In the QuARTS assays described herein, the flap oligonucleotides have a target specific region of 12 bases, while the LQAS assays use flap oligonucleotides have a target specific region of at least 13 bases, and use different thermal cycling procedures for amplification. Fluorescence signal generated by the QuARTS and LQAS reactions are monitored in a fashion similar to real-time PCR, permitting quantitation of the amount of a target nucleic acid in a sample.

An exemplary QuARTS PCR-flap assay reaction typically comprises approximately 200-600 nM (e.g., 500 nM) of each primer and detection probe, approximately 100 nM of the invasive oligonucleotide, approximately 600-700 nM of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies, and comprising a "black hole" quencher, e.g., BHQ-1, BHQ-2, or BHQ-3, BioSearch Technologies), 6.675 ng/µL FEN-1 endonuclease (e.g., Cleavase® 2.0, Hologic, Inc.), 1 unit Taq DNA polymerase in a 30 µL reaction volume (e.g., GoTaq® DNA polymerase, Promega Corp., Madison, WI), 10 mM 3-(n-morpholino) propanesulfonic acid (MOPS), 7.5 mM MgCl$_2$, and 250 µM of each dNTP.

Exemplary QuARTS cycling conditions are as shown below:

| QuARTS Reaction Cycle: | | | |
|---|---|---|---|
| Stage | Temp/Time | Number of Cycles | Acquisition |
| Pre-incubation | 95° C./3 min. | 1 | none |
| Amplification 1 | 95° C./20 sec. | 10 | none |
| | 63° C./30 sec. | | none |
| | 70° C./30 sec. | | none |
| Amplification 2 | 95° C./20 sec. | 35 | none |
| | 53° C./1 min. | | single |
| | 70° C./30 sec. | | none |
| Cooling (hold) | 40° C./30 sec. | 1 | none |

An exemplary LQAS reaction typically comprises approximately 200-600 nmol/L of each primer, approximately 100 nmol/L of the invasive oligonucleotide, approximately 500 nmol/L of each flap oligonucleotide probe and FRET cassette. LQAS reactions may, for example, be subjected to the following thermocycling conditions:

| Stage | Temp/Time | # of Cycles |
|---|---|---|
| Denaturation | 95° C./3' | 1 |
| Amplification | 95° C./20" | 40 |
| | 63° C./1' | |
| | 70° C./30" | |
| Cooling | 40° C./30" | 1 |

Targeted Pre-Amplification

Pre-amplification is often done in multiplex form, i.e., multiple different target nucleic acids are amplified together. A pre-amplification is conducted, for example, in a reaction mixture containing 7.5 mM MgCl$_2$, 10 mM MOPS, 0.3 mM Tris-HCl, pH 8.0, 0.8 mM KCl, 0.1 µg/µL BSA, 0.0001% Tween-20, 0.0001% IGEPAL CA-630, 250 µM each dNTP, oligonucleotide primers, (e.g., for 12 targets, 12 primer pairs/24 primers, in equimolar amounts (including but not limited to the ranges of, e.g., 200-500 nM each primer), or with individual primer concentrations adjusted to balance amplification efficiencies of the different target regions), 0.025 units/µL HotStart GoTaq concentration, and 20 to 50% by volume of bisulfite-treated target DNA (e.g., 10 µL of target DNA into a 50 µL reaction mixture, or 50 µL of target DNA into a 125 µL reaction mixture). Thermal cycling times and temperatures are selected to be appropriate for the volume of the reaction and the amplification vessel. For example, the reactions may be cycled as follows:

| Stage | Temp/Time | #of Cycles |
|---|---|---|
| Pre-incubation | 95° C./5' | 1 |
| Amplification 1 | 95° C./30" | 10-12 |
| | 64° C./30" | |
| | 72° C./30" | |
| Cooling | 4° C./Hold | 1 |

After thermal cycling, aliquots of the pre-amplification reaction (e.g., 10 µL) are diluted to 500 µL in 10 mM Tris, 0.1 mM EDTA, with or without fish DNA. Aliquots of the diluted pre-amplified DNA (e.g., 10 µL) are used in a QuARTS PCR-flap assay, e.g., as described above. See also U.S. Patent Appl. Ser. No. 62/249,097, filed Oct. 30, 2015; application Ser. No. 15/335,096, filed Oct. 26, 2016, and PCT/US16/58875, filed Oct. 26, 2016, each of which is incorporated herein by reference in its entirety for all purposes.

A combined pre-amplification and LQAS assay is referred to as the TELQAS assay (for "Target Enrichment Long probe Quantitative Amplified Signal").

Using the pre-amplified sample, QuARTS and TELQAS reactions are set up as follows:

| Mastermix (per reaction) | Volume per reaction (µL) |
|---|---|
| Water (mol. biol. grade) | 15.50 |
| 10X Oligo Mix* | 3.00 |
| 20X QuARTS/LQAS Enzyme Mix** | 1.50 |
| Total Mastermix volume | 20.0 |
| Reaction Mix | |
| Mastermix | 20 |
| Pre-amplified Sample | 10 |
| Final Reaction volume | 10 |

*10X oligonucleotide mix = 2 µM each primer and 5 µM each probe and FRET oligonucleotide
**20X enzyme mix contains 1 unit/µL GoTaq Hot start polymerase (Promega), 292 ng/µL Cleavase 2.0 flap endonuclease(Hologic).

As noted above, the flap oligonucleotides in the QuARTS assays have a target specific region of 12 bases, while the LQAS assays use flap oligonucleotides have a target specific region of at least 13 bases and are subjected to different thermal cycling conditions.

QuARTS reactions are subjected to the following thermocycling conditions:

QuARTS Assay Reaction Cycle:

| Stage | Temp/Time | Ramp Rate (° C. per second) | Number of Cycles | Signal Acquisition |
|---|---|---|---|---|
| Pre-incubation | 95° C./3 min | 4.4 | 1 | No |
| Amplification 1 | 95° C./20 sec | 4.4 | 5 | No |
| | 63° C./30 sec | 2.2 | | No |
| | 70° C./30 sec | 4.4 | | No |
| Amplification 2 | 95° C./20 sec | 4.4 | 40 | No |
| | 53° C./1 min | 2.2 | | Yes |
| | 70° C./30 sec | 4.4 | | No |
| Cooling | 40° C./30 sec | 2.2 | 1 | No |

LQAS/TELQAS reactions are subjected to the following thermocycling conditions:

TELQAS Assay Reaction Cycle:

| Stage | Temp/Time | Ramp Rate (° C. per second) | Number of Cycles | Signal Acquisition |
|---|---|---|---|---|
| Pre-incubation | 95° C./3 min | 4.4 | 1 | No |
| Amplification | 95° C./20 sec | 4.4 | 40 | No |
| | 63° C./1 min | 2.2 | | Yes |
| | 70° C./30 sec | 4.4 | | No |
| Cooling | 40° C./30 sec | 2.2 | 1 | No |

LQAS/TELQAS for RNA Detection ("RT-LQAS" or "RT-TELQAS")

An exemplary RT-LQAS reaction contains 20 U of MMLV reverse transcriptase (MMLV-RT), 219 ng of Cleavase® 2.0, 1.5 U of GoTaq® DNA Polymerase, 200 nM of each primer, 500 nM each of probe and FRET oligonucleotides, 10 mM MOPS buffer, pH 7.5, 7.5 mM MgCl$_2$, and 250 µM each nNTP. An exemplary protocol is as follows:

1. Remove the required oligonucleotide mixes needed from the −20° C. freezer and allow to thaw.
2. Thaw controls from the −80° C. for a brief time at room temperature, then place on ice.
3. Thaw sample plate from the −80° C. for a brief time at room temperature, then place on ice.
4. Prepare master mix for the oligo mixtures in an appropriately sized tube.
5. Dilute MMLV-RT 1:20 in H$_2$O mRNA Reverse Transcription 10X Master Mix Formulation

| Component | µL/reaction |
|---|---|
| Nuclease Free-H$_2$O (Promega) | 14.5 |
| MMLV_RT Diluted in NF H$_2$O | 1.0 |
| 10X Oligo Mix | 3.00 |
| 20X Enzyme Mix | 1.5 |
| Total Volume Master Mix (µL) | 20.0 |
| Sample Vol. (µL) | 10 |
| Final RT-LQAS Reaction Vol. (µL) | 30 |

6. Pipette 20 µL of master mix into a 96-well RT-LQAS plate, using a matrix pipet OR an eight-channel P20 pipet, per the plate layout.
7. Load 10 µL of samples (target nucleic acid), controls, calibrators (dilution series for calibration) (per plate layout).
8. Seal plate and briefly centrifuge.
9. Run plates with following reaction conditions on the Reactions are typically run on a thermal cycler configured to collect fluorescence data in real time (e.g., continuously, or at the same point in some or all cycles). For example, a Roche LightCycler 480 instrument or an Applied Biosystem QuantStudioDX Real-Time PCR instrument may be used under the following conditions:

RT-LQAS Assay Reaction Cycle:

| Stage | Temp/Time | Ramp Rate (° C. per second) | Number of Cycles | Signal Acquisition |
|---|---|---|---|---|
| Reverse Transcription | 42° C./ 30 min | 4.4 | 1 | No |
| Pre-incubation | 95° C./3 min | 4.4 | 1 | No |
| Amplification | 95° C./20 sec | 4.4 | 45 | No |
| | 63° C./1 min | 2.2 | | Single |
| | 70° C./30 sec | 4.4 | | No |
| Cooling | 40° C./30 sec | 2.2 | 1 | No |

In some embodiments, RT-LQAS assays may comprise a step of multiplex reverse transcription and pre-amplification, e.g., to pre-amplify 2, 5, 10, 12, or more targets in a sample (or any number of targets greater than 1 target), as described above, and may be referred to as "RT-TELQAS." In preferred embodiments, an RT-pre-amplification is conducted in a reaction mixture containing, e.g., 20 U of MMLV reverse transcriptase, 1.5 U of GoTaq® DNA Polymerase, 10 mM MOPS buffer, pH7.5, 7.5 mM MgCl$_2$, 250 µM each dNTP, and oligonucleotide primers, (e.g., for 12 targets, 12 primer pairs/24 primers, in equimolar amounts (e.g., 200 nM each primer), or with individual primer concentrations adjusted to balance amplification efficiencies of the different targets). Thermal cycling times and temperatures are selected to be appropriate for the volume of the reaction and the amplification vessel. For example, the reactions may be cycled as follows:

| Stage | Temp/Time | #of Cycles |
|---|---|---|
| RT | 42° C./30' | 1 |
| | 95° C./3' | 1 |
| Amplification | 95° C./20" | 10 |
| | 63° C./30" | |
| | 70° C./30" | |
| Cooling | 4° C./Hold | 1 |

After thermal cycling, aliquots of the RT-pre-amplification reaction (e.g., 10 µL) are diluted to 500 µL in 10 mM Tris, 0.1 mM EDTA, with or without fish DNA. Aliquots of the diluted pre-amplified DNA (e.g., 10 µL) are used in LQAS/TELQAS PCR-flap assays, as described above. In some embodiments, LQAS/TELQAS PCR flap assays are performed using additional amounts of the same primer pairs Example 1

Figure 6A:
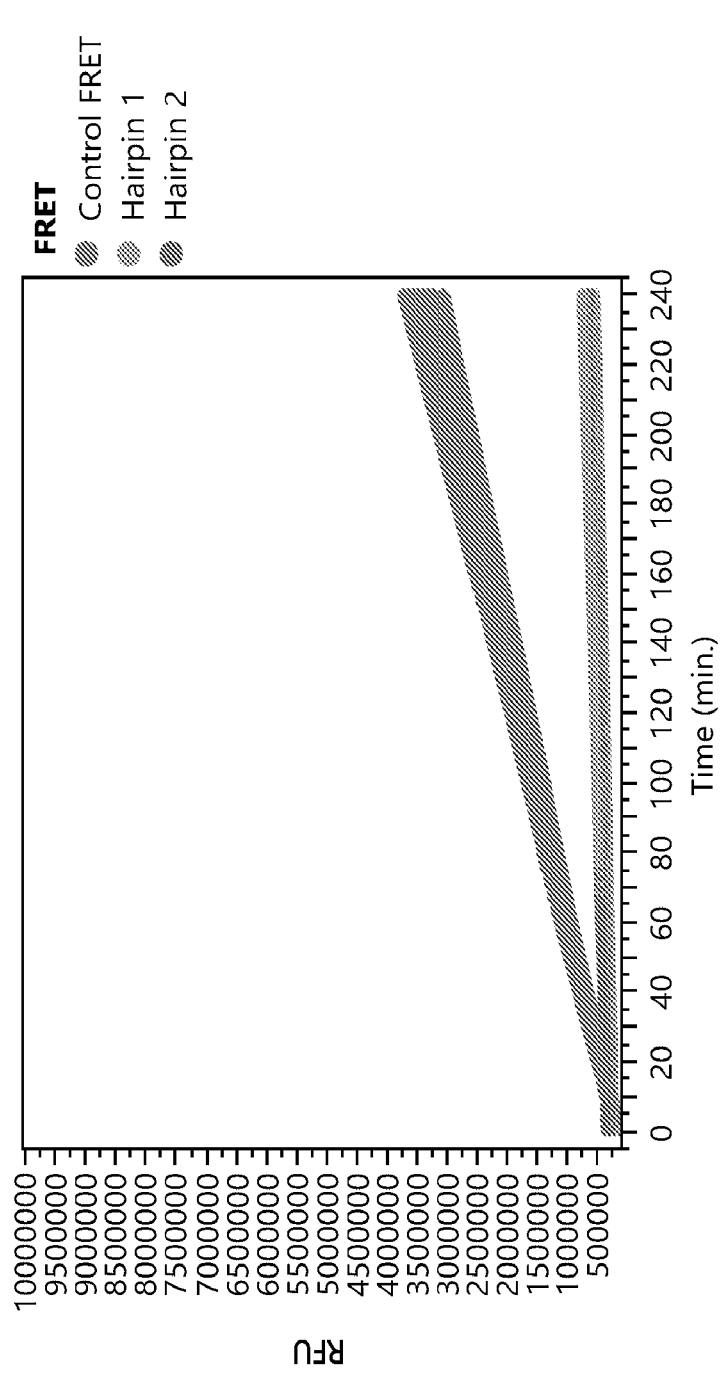
FIG. 6A provides a graph comparing background fluorescence from a standard FRET cassette and from two 5' hairpin FRET reporters (hairpin 1 and hairpin 2) used in a serial invasive signal amplification reaction in the absence of target template.
Figure 6B:
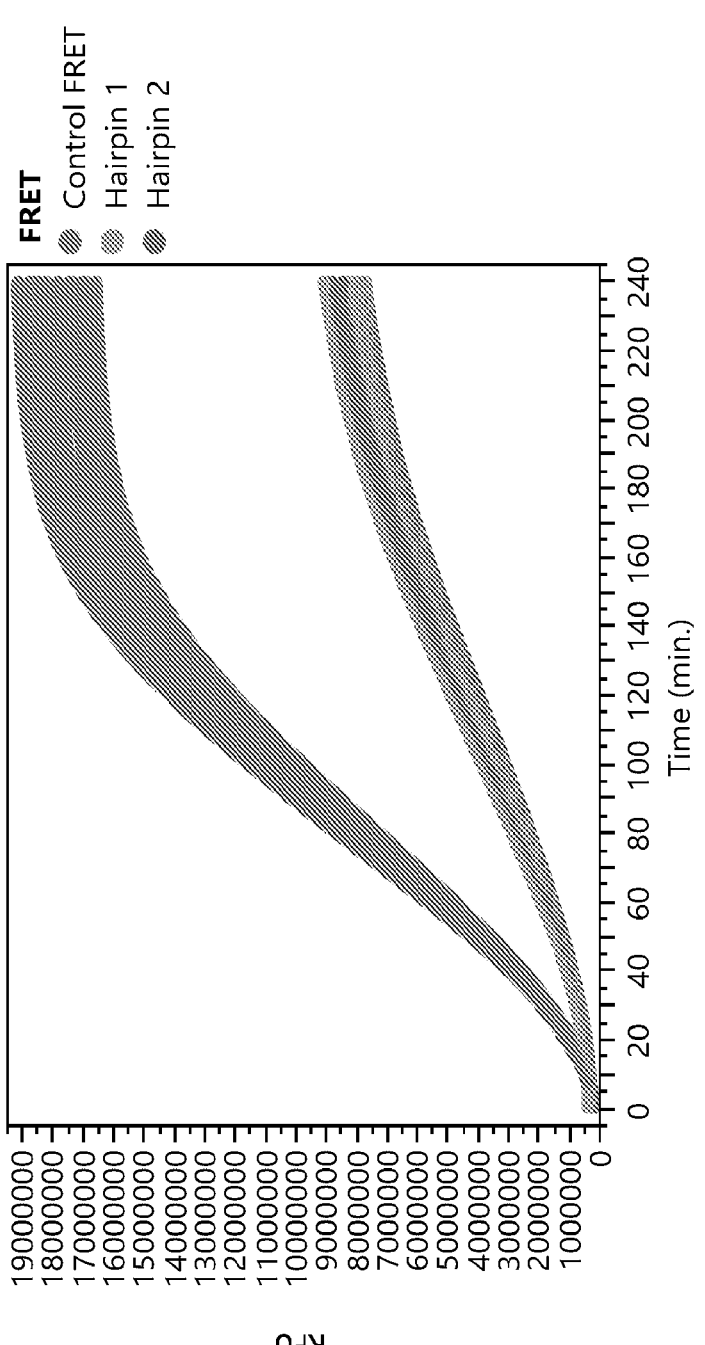
FIG. 6B provides a graph comparing signal from a standard FRET cassette and from two 5' hairpin FRET reporters (hairpin 1 and hairpin 2), used in a serial invasive signal amplification reaction in the presence of target template.
Figure 7A:
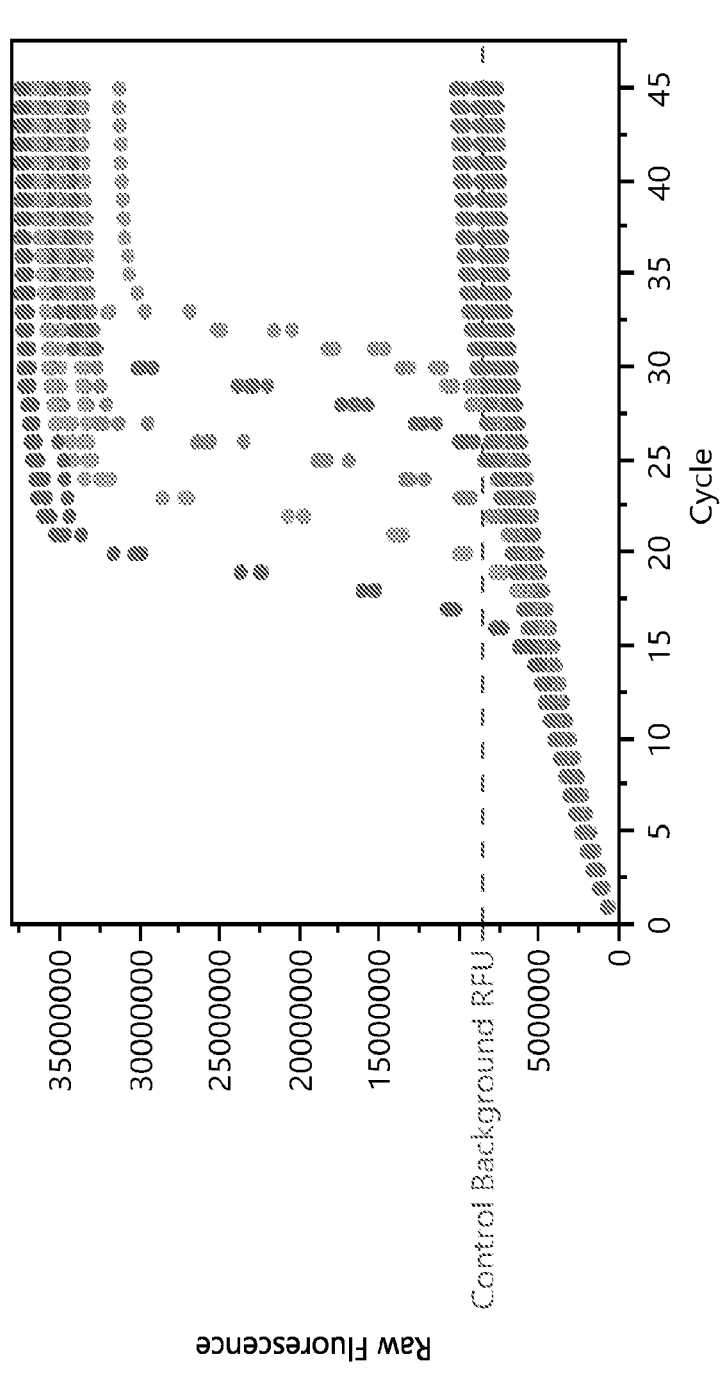
FIGS. 7A, 7B, 7C, and D provide graphs comparing signal from a standard FRET cassette (FIG. 7A) and from three 5' hairpin FRET reporters (FIGS. 7B, 7C, and 7D, showing data for hairpins 1, 2, and 3, respectively) used in real-time PCR reactions combined with invasive cleavage chemistry (Long-probe Quantitative Amplified Signal, LQAS). FRET assay reporters were designed with and without a 5' hairpin and tested in an assay design that demonstrated high background signal with a standard FRET cassette (FIG. 7A). The inclusion of the 5' hairpin resulted in a reduction of background signal (FIGS. 7B, 7C, and 7D), resulting in cleaner amplification curves and improved signal to noise ratio.
Figure 7B:
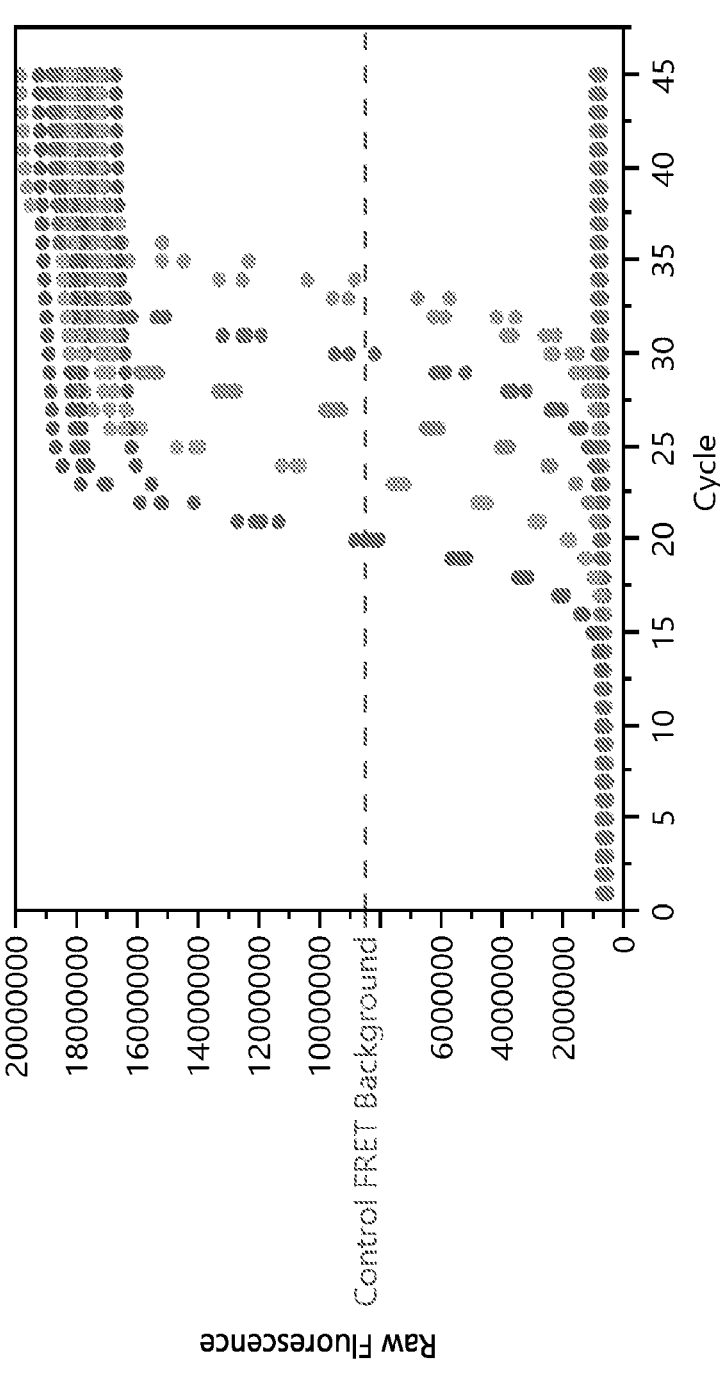
Figure 7C:
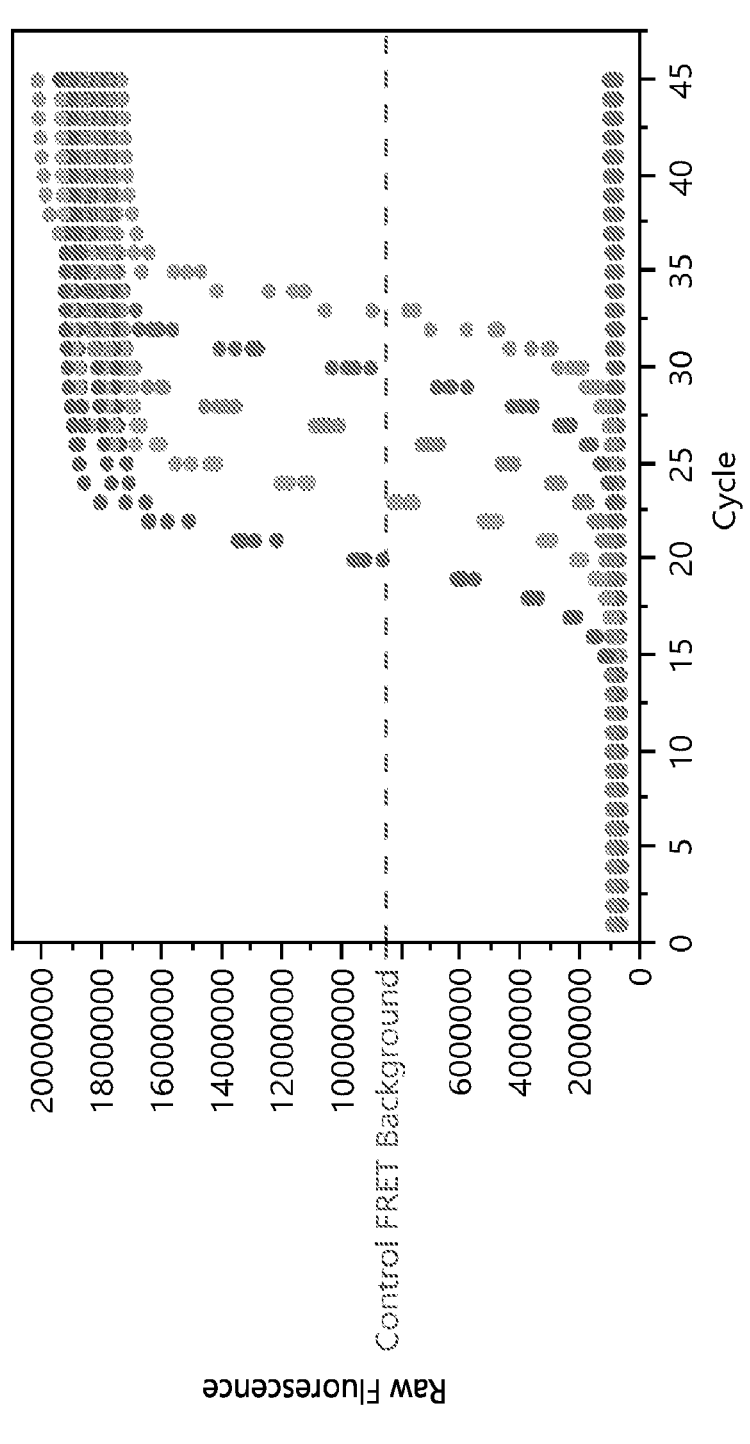
Figure 7D:
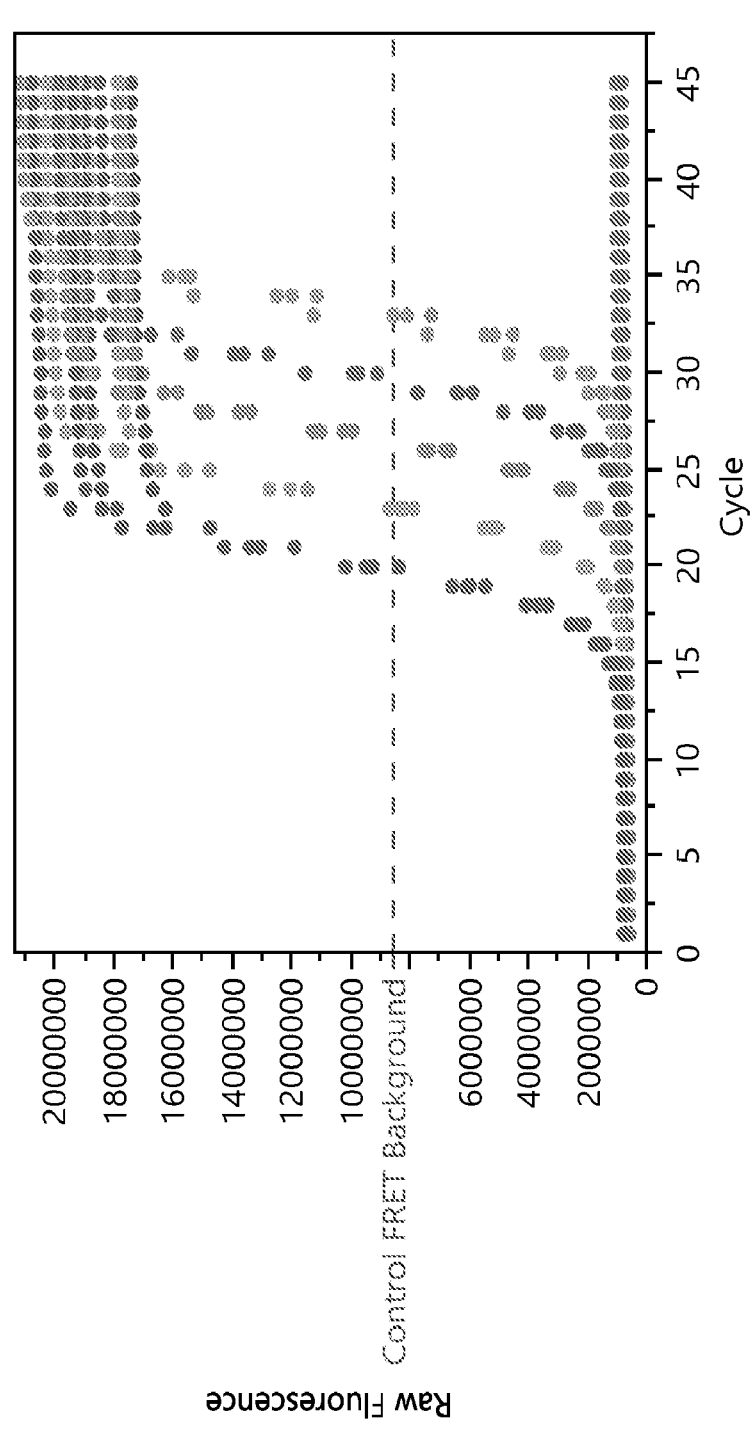

Comparison of Standard FRET Cassette to 5' Hairpin FRET Reporters in Serial Invasive Cleavage and PCR-Flap Endonuclease Assays A standard FRET cassette design (see FIG. 2, e.g.) was modified to include one of two different 5' hairpins (see FIGS. 3A-3D). These two 5' hairpin FRET reporters were tested alongside a standard FRET cassette (no 5' hairpin) in a serial invasive cleavage assay in the presence or absence of a target DNA recognized by the assay oligonucleotides. Each 5' hairpin assay reporter used FAM as a fluorophore and Black Hole Quencher® 1 ("BHQ1," Biosearch Technologies) as a quencher, incorporated on T nucleotides as indicated in FIG. 3. Serial invasive cleavage assays were performed as described by Hall J G, et al., *Proc Natl Acad Sci USA* 97:8272-8277 (2000) and fluorescence signal was measured in real time. The results are shown in FIGS. 6A (no target control) and 6B (with target).

background slope for reactions that used any of the 5' hairpin FRET reporters (FIGS. 7B-7D). The reduction in background slope resulted in improved signal-to-noise ratios when these reactions were compared to the no-template control reactions.

Shown below are the sequences of the three 5' hairpin FRET reporter molecules tested in these flap assay reactions. These reporters comprised different 5' hairpin designs having different calculated melting temperatures, as indicated below.

| Oligo Name | Sequence | Tm (° C.) of hairpin, calculated |
|---|---|---|
| 5' hairpin-FRET-1 | 5'-CAGTTTTCTG-(T-FAM)-TCT-(T-BHQ-1)-AGCCGGTTTTCCGGCTAAGACGTCCGTGGCCT-C6 3' (SEQ ID NO: 7) | 41.7 |
| 5' hairpin-FRET-2 | 5'-CAACTTTTGTTG-(T-FAM)-TCT-(T-BHQ-1)-AGCCGGTTTTCCGGCTAAGACGTCCGTGGCCT-C6 3' (SEQ ID NO: 8) | 51.4 |
| 5' hairpin-FRET-3 | 5'-GCGTTTTCGC-(T-FAM)-TCT-(T-BHQ-1)-AGCCGGTTTTCCGGCTAAGACGTCCGTGGCCT-C6 3' (SEQ ID NO: 9) | 59.2 |

These data show that use of a FRET cassette without a 5' hairpin resulted in higher fluorescence levels both without and with target DNA in the reaction. While the 5' hairpin FRET reporters exhibited lower fluorescence signal in template-positive reactions, the separation between the negative and positive template reactions increased relative to the control FRET cassette. Signal-to-noise ratios were calculated for each FRET reporter to determine the separation between signals from positive (with target template) and negative (without target template) reactions, for each of the different FRET assay reporter designs.

$$\text{Signal to Noise} = \frac{\text{Average } (RFU\,sample)}{\text{Average } (RFU\,negctrl)}$$

| FRET Reporter | Time (min) | Signal to noise |
|---|---|---|
| Control (standard FRET cassette) | 225 | 5.45 |
| 5' Hairpin 1 | 225 | 13.21 |
| 5' Hairpin 2 | 225 | 13.60 |

These data show that use of the FRET reporter molecules containing a 5' hairpin-forming sequence resulted in greater separation between signal and noise. The greater separation is largely due to a reduction in background signal generated in the negative (no target) sample sets.

PCR-Flap Assay Reactions

FRET cassettes used in real-time PCR-flap endonuclease assays (LQAS assays, as described above) were replaced with FRET assay reporters that include a 5' hairpin. Primary structures for 5' hairpin FRET reporters 1, 2, and 3 are shown in FIG. 3A, and secondary structures are shown in 3B-3D. The FRET assay reporters with and without 5' hairpin-forming sequences were compared in PCR-flap assay reactions. These data are shown in FIGS. 7A (using a standard FRET cassette), 7B (using 5' hairpin FRET reporter 1), 7C (using 5' hairpin FRET reporter 2), and 7D (using 5' hairpin FRET reporter 3). These data show a reduction in Example 2

Single Molecule Flap Endonuclease Substrate

Figure 8B:
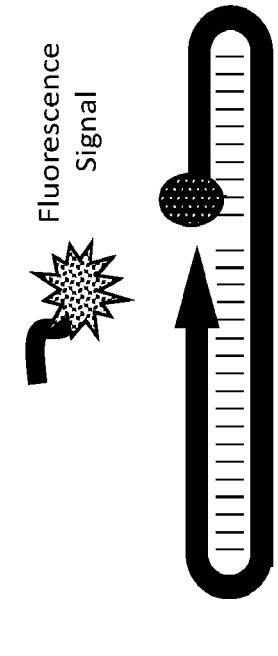
Figure 9:
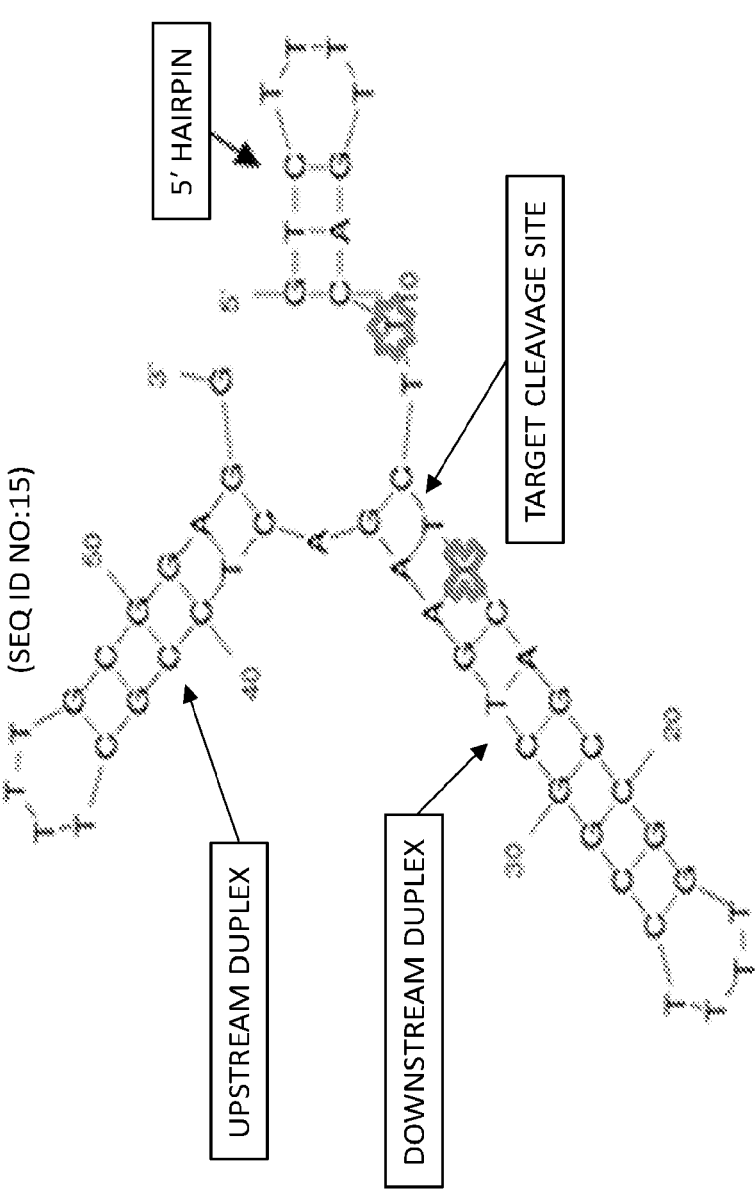
FIG. 9 provides a predicted secondary structure of an embodiment of a 5' hairpin test substrate, with upstream and downstream duplexes, target cleavage site, and 5' hairpin in a repressive 5' flap indicated.

Cleavage reactions on single molecule substrates without and with cleavage-suppressing 5' hairpins were compared. Each substrate comprised a fluorophore and a quencher, as shown schematically in FIG. 8. An example of a secondary structure for a single molecule test substrate is shown in FIG. 9. The linear sequence of this molecule is shown as 'v3' in table below. Other iterations of the design include a 5' hairpin containing a 9-carbon spacer (C9), a set of abasic internal modifications (dS), or a two-molecule approach where a shorter oligo is annealed to a single stranded 5'-arm.

Real-time monitoring of fluorescence over time provides a direct indication of enzymatic activity. Identification of the linear portion of the reaction allows linear regression to assign an RFU/s value indicative of flap endonuclease activity (see FIG. 10).

Assays comprise one of the single molecule substrates, flap endonuclease enzyme, $MgCl_2$ or $MnCl_2$, and a buffering agent. A carrier protein, such as Bovine Serum Albumin (BSA) may also be used in the assay. To perform an assay, a reference lot of a flap endonuclease enzyme is diluted in a standard curve. An unknown enzyme (e.g., a FEN-1 endonuclease) is then diluted to target the center of the reference titration. Below is an example of the reaction concentrations that may be used.

TABLE 1

| Flap Endonuclease Test Reaction Formulation | |
|---|---|
| Reagent | Reaction Concentration |
| Water | NA |
| MOPS, pH 7.5 | 10 mM |
| MgCl2 | 7.5 mM |
| Substrate | 5 μM |
| Enzyme | 15-150 nM |

Figure 12:
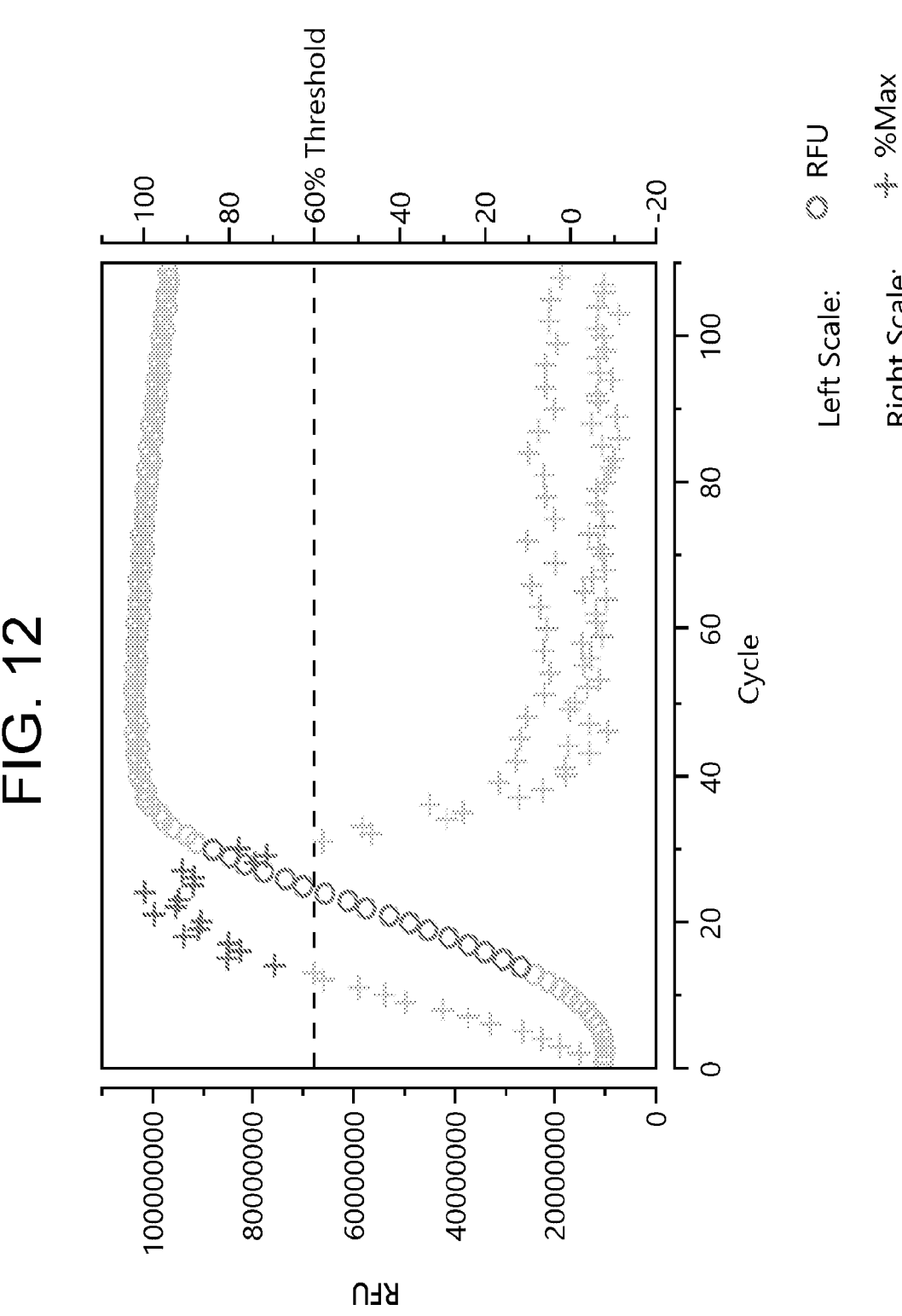
FIG. 12 provides a graph showing fluorescent signal measured during a reaction as a direct measure of the amount of cleaved 5' hairpin test substrate v3, as described below.

The enzyme dilutions are mixed with substrate, buffer, and $MgCl_2$. These reactions are then incubated at an isothermal temperature at which kinetic fluorescence is monitored. The detected rate that fluorescence increases over time is a direct indication of enzyme activity. As a result, the reference titration provides a differential response based on enzyme concentration that may be used to generate a standard curve (FIG. 12). This standard curve may be used to perform linear regression to determine a relative percent activity for an unknown lot of enzyme.

Figure 11A:
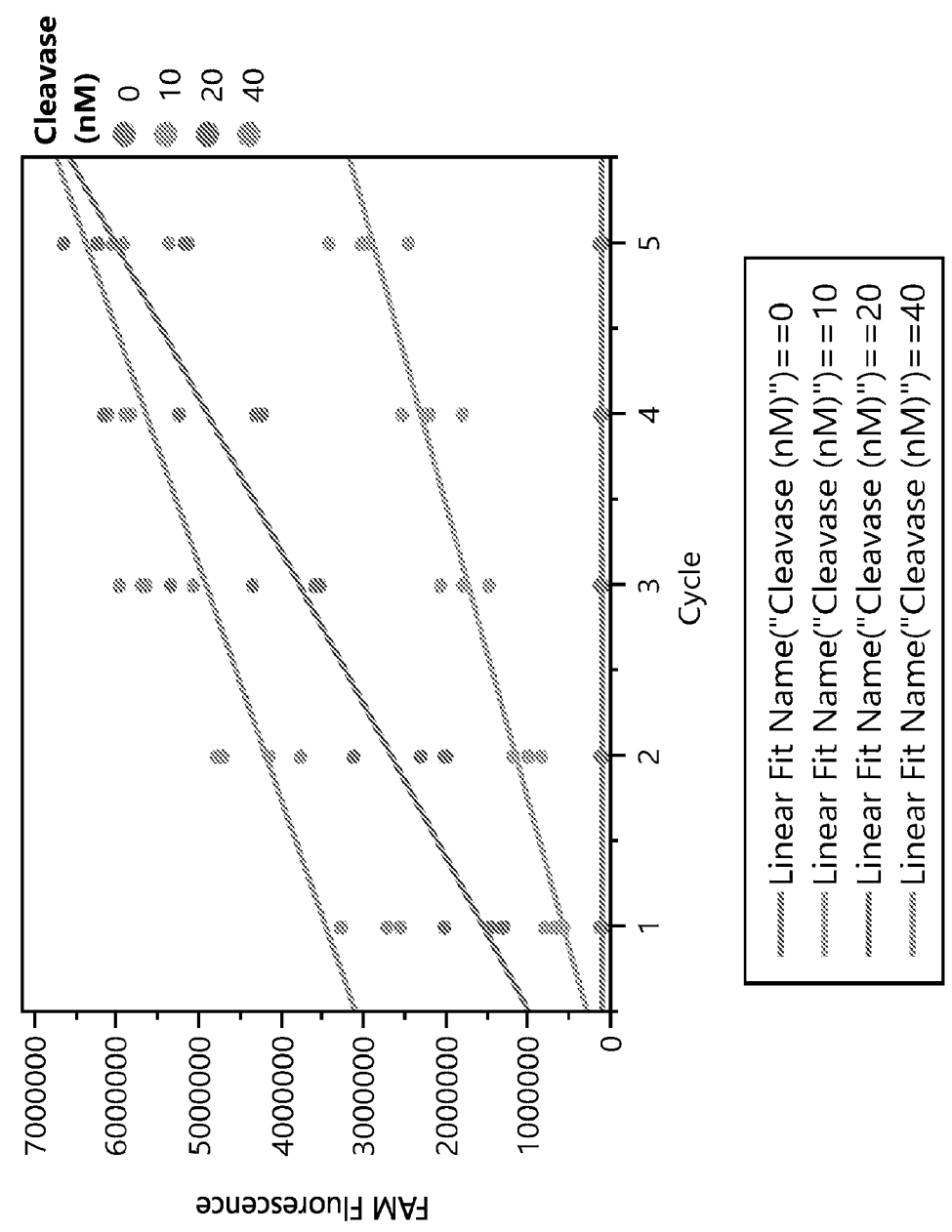
FIGS. 11A and 11B provide graphs illustrating the ability of the 5' hairpin structures to repress flap endonuclease cleavage at the reporting cleavage site (FIG. 11B), compared to flap endonuclease activity measured on a substrate lacking a repressive 5' hairpin (FIG. 11A).
Figure 11B:
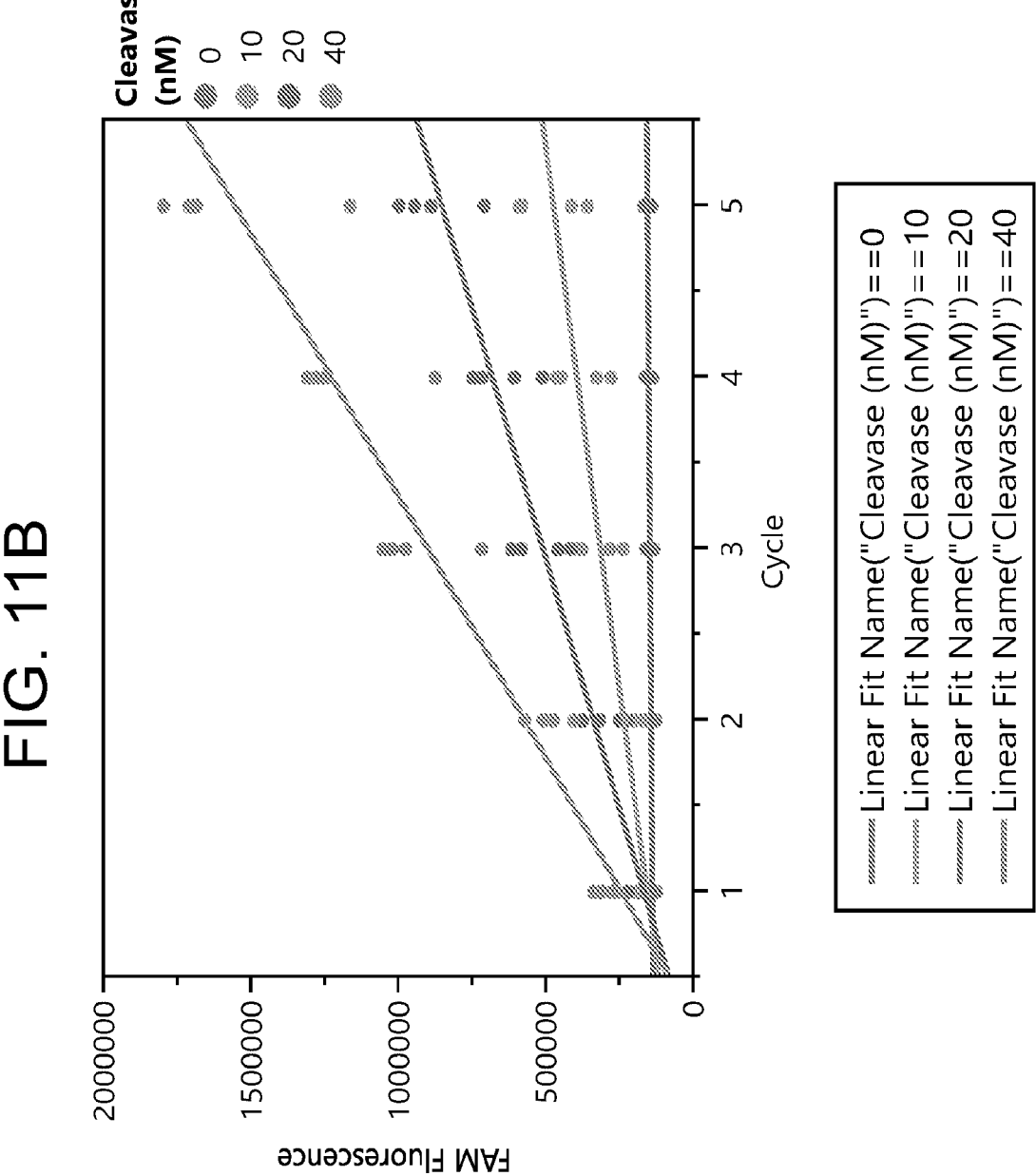

The table below provides the primary sequences of exemplary single molecule substrates:

v1 (FAMS and FAML)=No Repressive Arm (no 5' hairpin)

v2 (dS)=5' hairpin oligonucleotide with "dSpacer" internal modifications used for the loop of the 5' hairpin.

v2(C9)=5' hairpin oligonucleotide with "Spacer9" internal modification used for the loop of the 5' hairpin.

v2 (HP)=5' hairpin oligonucleotide with "T" used as the loop sequence in the 5' hairpin.

the control FRET cassette lacking a 5' hairpin described above. The graph shows fluorescence measured at an incubation temperature of 53° C. for reactions on single substrates without (FIG. 11A) or with (FIG. 11B) a repressive arm. The oligonucleotides containing the repressive 5' hairpins showed low fluorescence at the start of data collection, suggesting successful repression of enzymatic cleavage during reaction setup, while the substrate without the repressive arm showed higher initial fluorescence, indicative of cleavage that occurred during the reaction setup. The 5' repressive arm also resulted in better uniformity and separation of slope across a range of enzyme concentrations (0-40 nM).

FIG. 12 shows that fluorescent signal measured during the reaction is a direct measure of the amount of cleaved substrate (test substrate v3, above). Therefore, quantitation of fluorescence over time (RFU/s) is a direct measure of enzyme activity. Identification of the linear portion of the reaction allows an RFU/s value to be determined for a given

TABLE 2

| Single-molecule Invasive Cleavage Test Substrates | |
|---|---|
| | Oligo Sequence (5'->3') |
| v1 (FAMS) | 5'-FAM-TCT-T(BHQ1)-AGCCGGTTTTCCGGCTGAGACTCCGCTTTTGCGGAGG-3' (SEQ ID NO: 10) |
| v1 (FAML) | 5'-FAM-TCT-T(BHQ1)- AGCCGGTTTTCCGGCTGAGACGTCCGTGGCCTTTTTAGGCCACGGACGG-3' (SEQ ID NO: 11) |
| v2 (HP) | 5'-TCCTTATTACTTTTGTAATAAGGA-T(FAM)-TCT-T(BHQ1)- CAGCCGGTTTTCCGGCTGAAGACTCCGCTTTTGCGGAGG-3' (SEQ ID NO: 12) |
| v2 (C9) | 5'-TCCTTATTAC-Spacer9-GTAATAAGGA-T(FAM)-TCT-T(BHQ1)- CAGCCGGTTTTCCGGCTGAAGACTCCGCTTTTGCGGAGG-3' (SEQ ID NO: 13) |
| v2 (dS) | 5'-TCCTTATTAC-dSpacer-dSpacer-dSpacer-d-Spacer-GTAATAAGGA-T(FAM)-TCT- T(BHQ1)-CAGCCGGTTTTCCGGCTGAAGACTCCGCTTTTGCGGAGG-3' (SEQ ID NO: 14) |
| v3* | 5'-GTCTTTTGAC-(T-FAM)-TCT-(T-BHQ1)- CAGCCGGTTTTCCGGCTGAAGACGCCGCTTTTGCGGCGG-3' (SEQ ID NO: 15) |
| v4 | 5'-GTCATTTTTGAC-(T-FAM)-TCT-(T-BHQ-1)- CAGCCGGTTTTCCGGCTGAAGACGCCGCTTTTGCGGCGG-3' (SEQ ID NO: 16) |
| V5 | 5'-GTCAC-(iSpacer9)-GTGAC-(T-FAM)-TCT-(T-BHQ1)- CAGCCGGTTTTCCGGCTGAAGACGCCGCTTTTGCGGCGG-3' (SEQ ID NO: 17) |

Figure 10:
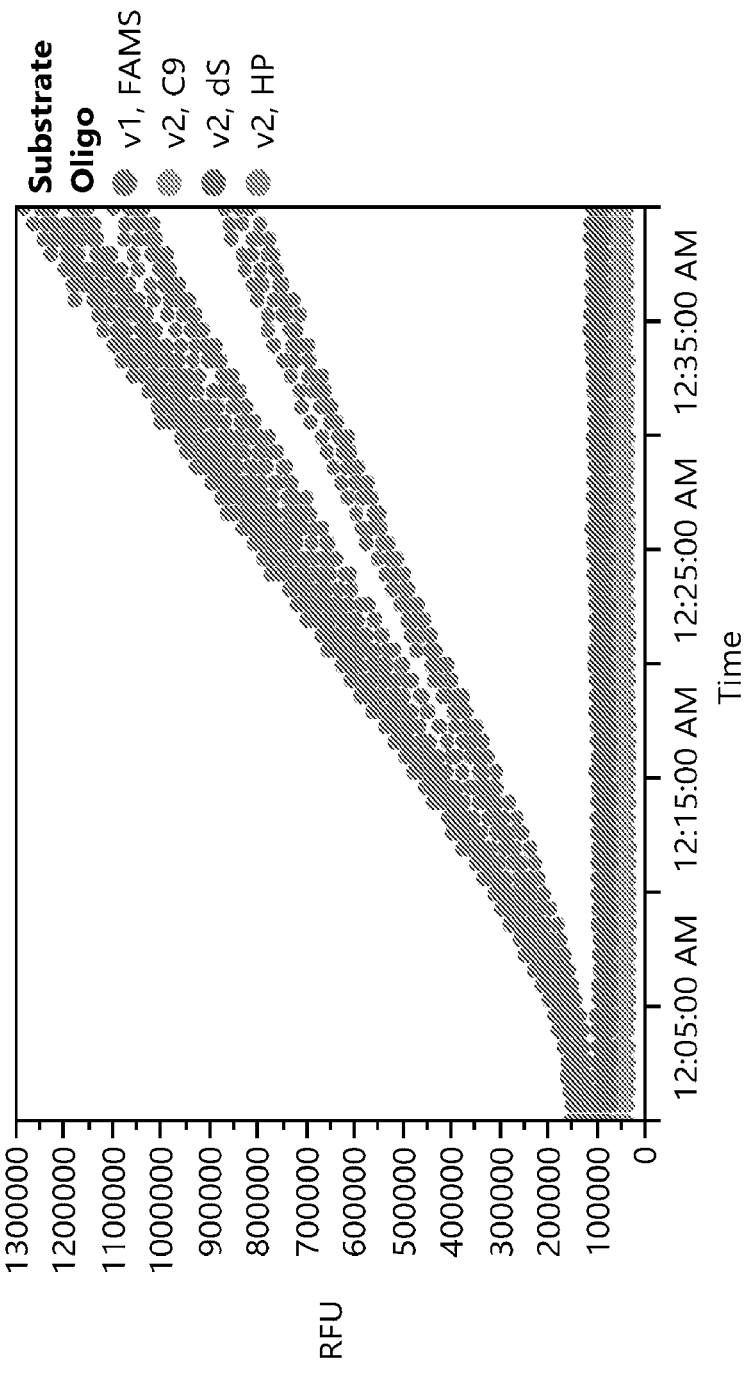
FIG. 10 provides a graph showing fluorescence using single molecule substrates with or without a repressive 5' hairpin, incubated at 35° C.

The graph in FIG. 10 shows fluorescence measured during incubation at a temperature of 35° C. using single substrates with or without a repressive 5' arm. Tests were conducted using the v3 test substrate, above, or a control FRET cassette having the same sequence but lacking the 5' hairpin portion, and using Cleavase® 2.0 (Hologic, Inc.) The oligonucleotides containing the repressive hairpins showed consistent low fluorescence throughout the incubation, while the substrate without the repressive arm showed higher initial fluorescence, indicative of cleavage occurring during transfer of the reaction mix to the reaction plate. These data also show fluorescence increasing over time for the substrate lacking the repressive arm, which suggests continuing cleavage occurring at this low incubation temperature.

The data in FIG. 11 illustrate the ability of the 5' structures to repress enzymatic cleavage at the target cleavage site. Tests were conducted using the v3 test substrate, above, or reaction. In order to do this, raw fluorescence data from each reaction is used to determine the first derivative at each time point across the dataset. The first derivative provides a direct indication of the rate of change. The first derivative data is then used to identify the maximum for each reaction, which is used to express the derivative data as a % maximum value. A threshold is applied to the % max data to determine a linear subset of RFU data for each reaction that can be used in linear regression to determine an RFU/s activity for each reaction. FIG. 12 illustrates a reaction curve (blue crosses) plotted alongside % max first derivative (red circles). The highlighted portion of the reaction curve is used for linear regression.

Figure 13A:
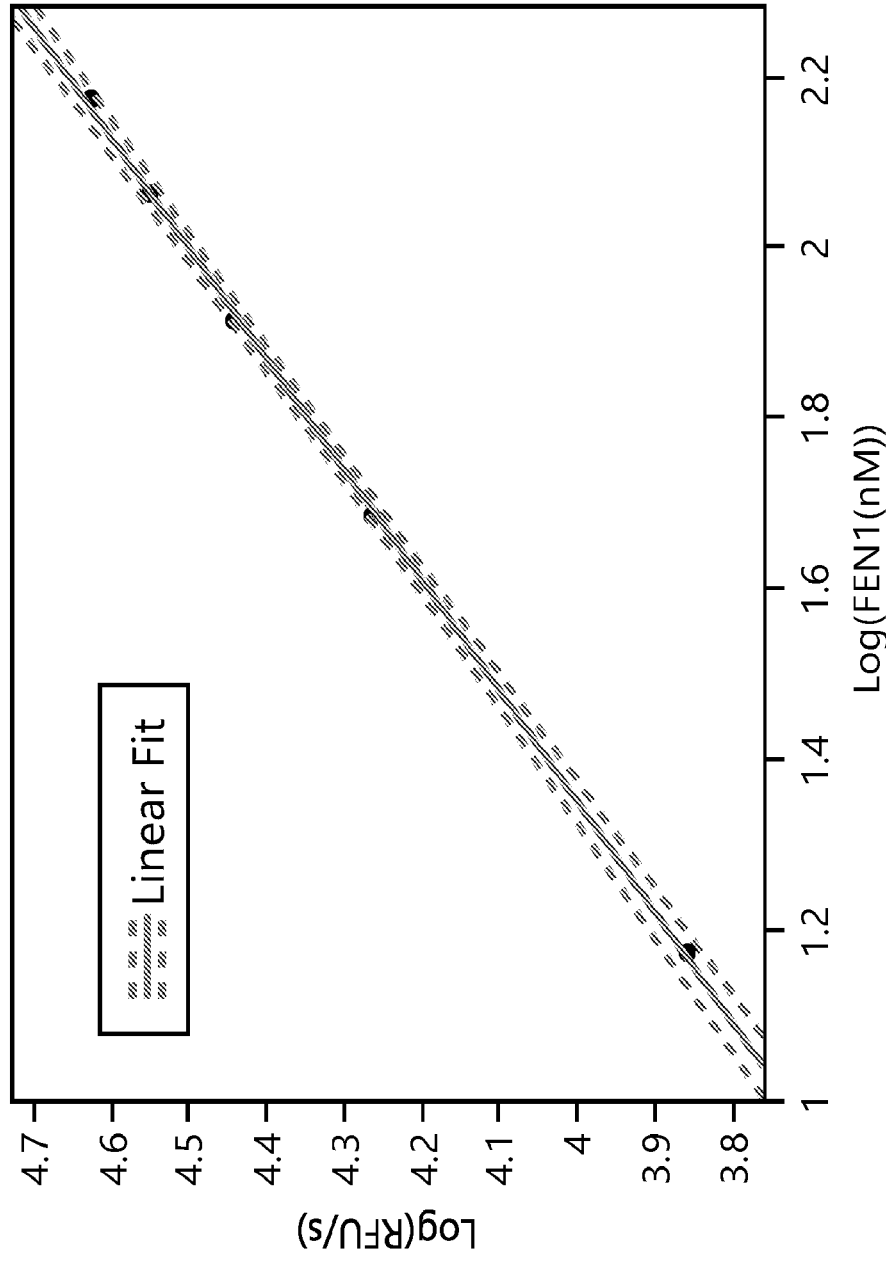

FIG. 13 illustrates that performing a titration of a reference material shows a differential response that results in a linear standard curve. This standard curve provides a means for determining relative performance of an unknown lot of enzyme. The rate of fluorescence increased over time (RFU/s) for the linear portion of the reaction is graphed vs. enzyme concentration.

Use of a repressive 5' modification, e.g., a 5' hairpin, reduces cleavage at the target cleavage site at ambient temperature. Because the substrate used in the assay is a single molecule, there is no need for an annealing reaction, and equimolarity of the quencher and fluorophore is ensured. As a result, the assay using the 3-hairpin single molecule substrate with a FRET labeling system (e.g., as illustrated in FIGS. 8 and 9) provides a means of monitoring flap endonuclease activity in real-time, reduces background cleavage, and provides a user-friendly setup. Previous assays used to characterize flap endonuclease activity did not control the start of the reaction and monitor in real time without the need for hybridization. The present technology provides an assay that is reproducible and that provides greater sensitivity.

Testing was performed to determine whether the assay was capable of distinguishing between different activity levels of lots of flap endonuclease enzyme. Low, centered, and high performing lots of Afu FEN-1 endonuclease (as determined by QuARTS assay performance) were tested against a reference dilution series. The results are shown in the table below.

TABLE 3

| Enzyme Performance Discrimination (on v3 test substrate, Table 2) | | | | | | | | |
|---|---|---|---|---|---|---|---|---|
| | FEN1 | | Log | Standard Curve | | | Relative Activity | Rel |
| FEN1 | (nM) | RFU/s | (RFU/s) | Slope | Intercept | R-Sq | (nM) | % Activity |
| High | 82.5 | 36674 | 4.56 | 0.719 | 3.122 | 0.998 | 102 | 123 |
| Mid | 82.5 | 32945 | 4.52 | 0.719 | 3.122 | 0.998 | 88 | 106 |
| Low | 82.5 | 23076 | 4.36 | 0.719 | 3.122 | 0.998 | 53 | 65 |

Results show that the assay using a 5' repressive arm test substrate has the ability to distinguish between a high, centered, and low performing lots of enzyme using linear regression against a standard curve. Further characterization of the assay included a multi-site study involving multiple operators, instruments, and reagent lots showed the reproducibility of the assay to be excellent, with % CV across all runs of 7-8% (data not shown).

This assay provides a simple workflow that can be performed in under 60 minutes. Data collection and analysis is straightforward and minimizes variables that may impact results. For instance, there is no need for temperature cycling, oligo hybridization, or Taq polymerization. Additionally, the use of kinetic fluorescence for real-time detection of enzyme activity provides a more sensitive approach for activity assessment than end point technologies.

Example 3

5' Hairpin Flaps on Probe Oligonucleotides in Invasive Cleavage Structures

Serial invasive cleavage assays were tested using 5' hairpins on the primary probe oligonucleotide, on the FRET reporter oligonucleotide, and on both. Also compared were primary probe oligonucleotides having 5' hairpins of different thermal stabilities, i.e., having a calculated Tm of 59° C. ("high" temp) or of 51° C. ("low" temp). Serial invasive cleavage assays were performed as described by Hall J G, et al., Proc Natl Acad Sci USA 97:8272-8277 (2000) except that the reactions were first incubated at a temperature in which cleavage at a targeted cleavage site should be blocked, followed by a shift to a temperature at which the 5' hairpin should unfold and cleavage at the targeted cleavage sites should occur. Fluorescence signal was measured in real time, at one-minute intervals.

In the experiments discussed below, the "probe" refers to the target-specific flap assay probe in a serial invasive cleavage reaction, sometimes referred to as a "primary probe." Digested plasma DNA containing a region of the LASS4_4482 gene was used as target material in the assays.

Oligonucleotides used in the serial invasive cleavage assays were as follows:

| Oligo Name | Sequence (5' to 3') | Tm (° C.) of hairpin, calculated |
|---|---|---|
| Forward Primer/Invader Oligonucleotide for LASS4_4482 target DNA | ACGGGTGTTCGAGGACG (SEQ ID NO: 18) | N/A |
| LASS4_4482_Probe (no HP) | AGGCCACGGACGGCGGTTGTGAAACGG/3C6/ (SEQ ID NO: 19) | |
| LASS4_4482_Probe HP1 ("low") | CAACTTTTGTTGAGGCCACGGACGGCGGTTGTGAAACGG/3C6/ (SEQ ID NO: 20) | 51.4 |
| LASS4_4482 Pb HP2 ("High") | CGAGTTTTCTCGAGGCCACGGACGGCGGTTGTGAAACGG/3C6/ (SEQ ID NO: 21) | 59.2 |

| Oligo Name | Sequence (5' to 3') | Tm (° C.) of hairpin, calculated |
|---|---|---|
| 5' hairpin-FRET-1 | 5'-CAGTTTTCTG-(T-FAM)-TCT-(T-BHQ-1)-AGCCGGTTTTCCGGCTAAGACGTCCGTGGCCT-C6 3' (SEQ ID NO: 7) | 41.7 |

Bench area was cleaned using 10% Bleach followed by a diH2O rinse and allowed to air dry. While air drying, pipettes were wiped down with 6% hydrogen peroxide. Oligonucleotides and reagents were removed from cold storage and allowed to equilibrate to room temperature for 30 minutes.

Reagents were prepared as follows:

1. Prepare a dilution of BSA:

| Component | Ci (mg/mL) | Cf (mg/mL) | Volume (uL) |
|---|---|---|---|
| BSA | 100 | 10 | 100 |
| nuclease free H2O | NA | NA | 900 |
| Total (1:10 BSA) | | | 1000 |

2. Prepare a 1:10 dilution of the Forward Primer/Invasive oligonucleotide

| Component | Ci (uM) | Cf (uM) | Volume (uL) |
|---|---|---|---|
| Invasive oligonucleotide | 100 | 10 | 10 |
| nuclease free H2O | NA | NA | 90 |
| Total (1:10 FP) | | | 100 |

3. Prepare a 10× Oligo Mix for each assay configuration to be tested:

| Description | Ci | Cf | 10X | Units | Volume to add (uL) |
|---|---|---|---|---|---|
| Water, dispensed | NA | NA | NA | NA | 612.50 |
| Invasive oligonucleotide | 10 | 0.05 | 0.500 | μM | 35.00 |
| Probe | 100 | 0.5 | 5.000 | μM | 35.00 |
| FRET reporter | 100 | 0.25 | 2.500 | μM | 17.50 |
| | | | | Total | 700 |

4. The following combinations of oligonucleotides were tested:

i. Control Mix—All standard components (no hairpins on FRET assay reporter or probe)

ii. Hairpin FRET+Standard probe iii. Hairpin Probe+Standard FRET cassette iv. Hairpin FRET+Hairpin Probe Serial invasive cleavage reactions were set up with a matrix of Standard or Hairpin FRETs (Arm 5 FAM) and Hairpin Probes. A control mix of a Standard Arm 7 FAM FRET and Arm 7 Probe was set up for comparison. The reactions were assembled as follows:

5. Make 10× reaction mix:

| Description | Ci | Cf* | Units | 10× | Volume to add (uL) |
|---|---|---|---|---|---|
| Nuclease FreeWater | NA | NA | NA | NA | 2741.25 |
| 1M MOPS pH 7.5 | 1000 | 10 | mM | 100 | 750 |
| 1M MgCl2 | 1000 | 7.5 | mM | 75 | 562.5 |
| 1M Tris-HCl, pH 8.0 | 1000 | 2 | mM | 20 | 150 |
| 1M KCl | 1000 | 5 | mM | 50 | 375 |
| 1:10 BSA | 10 | 0.002 | mg/mL | 0.02 | 15 |
| 20% Tween 20 | 20 | 0.05 | % | 0.5 | 187.5 |
| 10% Igepal CA-630 | 10 | 0.05 | % | 0.5 | 375 |
| 80% Glycerol | 80 | 2.5 | % | 25 | 2343.75 |
| Cleavase | 4380 | 7.3 | ng/uL | 73 | 125.00 |
| | | | | Total: | 7500 |

6. Make Serial invasive cleavage assay reaction mix:

| Description | Ci | Cf* | Volume to add (uL) |
|---|---|---|---|
| 10× Reaction Mix | 10 | 1 | 210 |
| 10× Oligo Mix | 10 | 1 | 210 |
| Nuclease Free H2O | NA | NA | 980 |
| Total | NA | NA | 1400 |
| Target | NA | NA | 700 |

7. Transfer 20 μL of master mixes to wells of a 96 well LightCycler Plate.
8. Transfer 10 μL of targets DNAs into plate wells. "no target" control reactions contained fish DNA diluent.
9. Seal plate and briefly spin in the plate spinner.
10. Run plate on the Quantstudio Dx per parameters below with reaction volume of 30 uL.

Cycling Conditions

| | | | | | |
|---|---|---|---|---|---|
| Invader Reaction Cycle: | | | | | |
| Stage | | Temp/ Time | Ramp Rate | Number of Cycles | Acquisition |
| Preincubation | | 40° C., or 50° C./1' | 1.6 | 180 | Single |
| Denaturation | | 95 C./5' | 1.6 | 1 | none |
| Invader | | 63° C./1' | 1.6 | 240 | Single |
| Cooling | | 40° C./30" | 1.6 | 1 | none |

As described above, the assay plates were incubated at 40° C. or 50° C. for 180 minutes, with data collected every minute. This incubation period shows the efficacy of blocking cleavage of the probes and hairpin FRET assay reporters at temperatures in which 5' hairpins are configured to block cleavage at the target cleavage sites. Plates were then incubated at 63° C. for 240 minutes, with data collected every minute. This incubation period shows the efficacy of the serial invasive cleavage assay reagents in generating signal in response to different amounts of the target DNA. "High" DNA reactions contained $2\times10^9$ strands, "Med" DNA reactions contained $2\times10^8$ strands, and "Low" DNA reactions contained $2\times10'$ strands of target DNA.

Figure 15A:
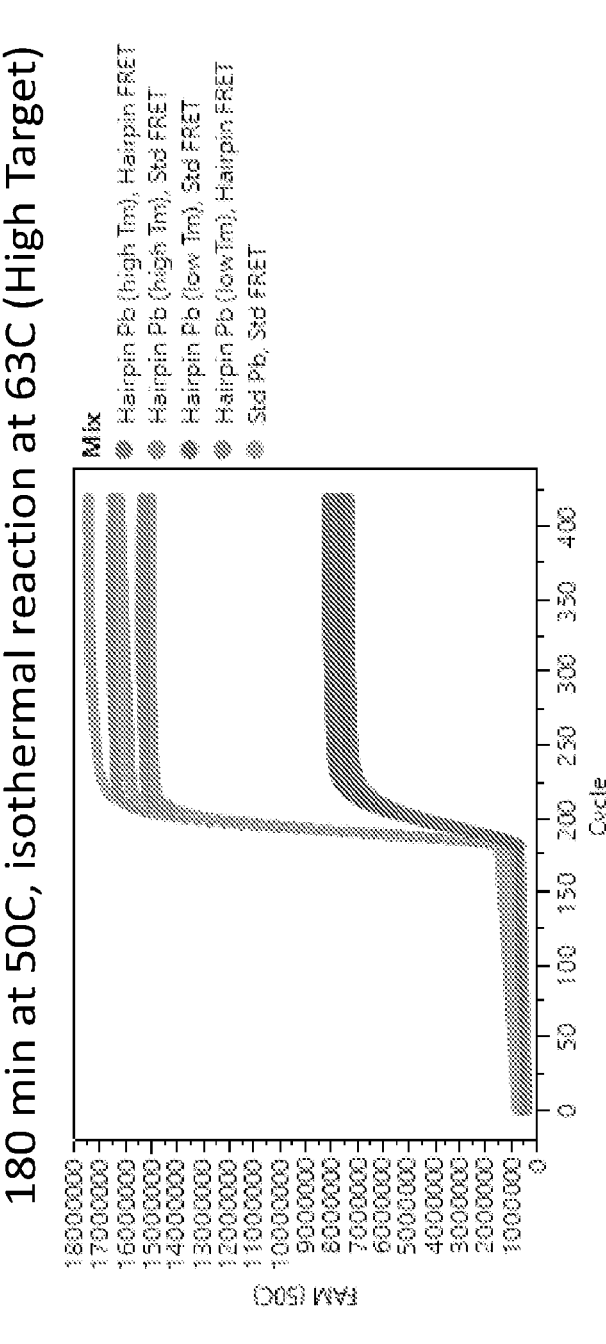
FIGS. 15A-15P provide graphs comparing signal from serial invasive cleavage assays having different amounts of target DNA and using standard probes or 5' hairpin probes, with either a standard FRET cassette or a 5' hairpin FRET cassette, as shown schematically in FIGS. 14A, 14B, and 14C, as described in Example 3.
Figure 15B:
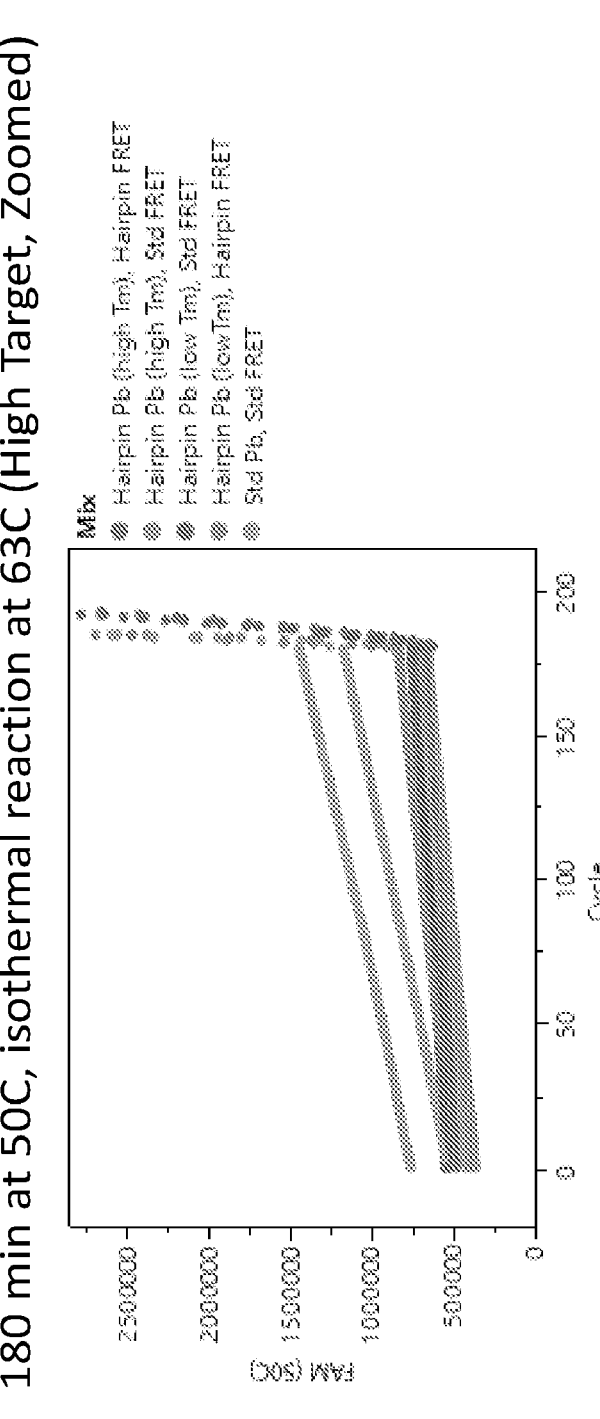
Figure 15C:
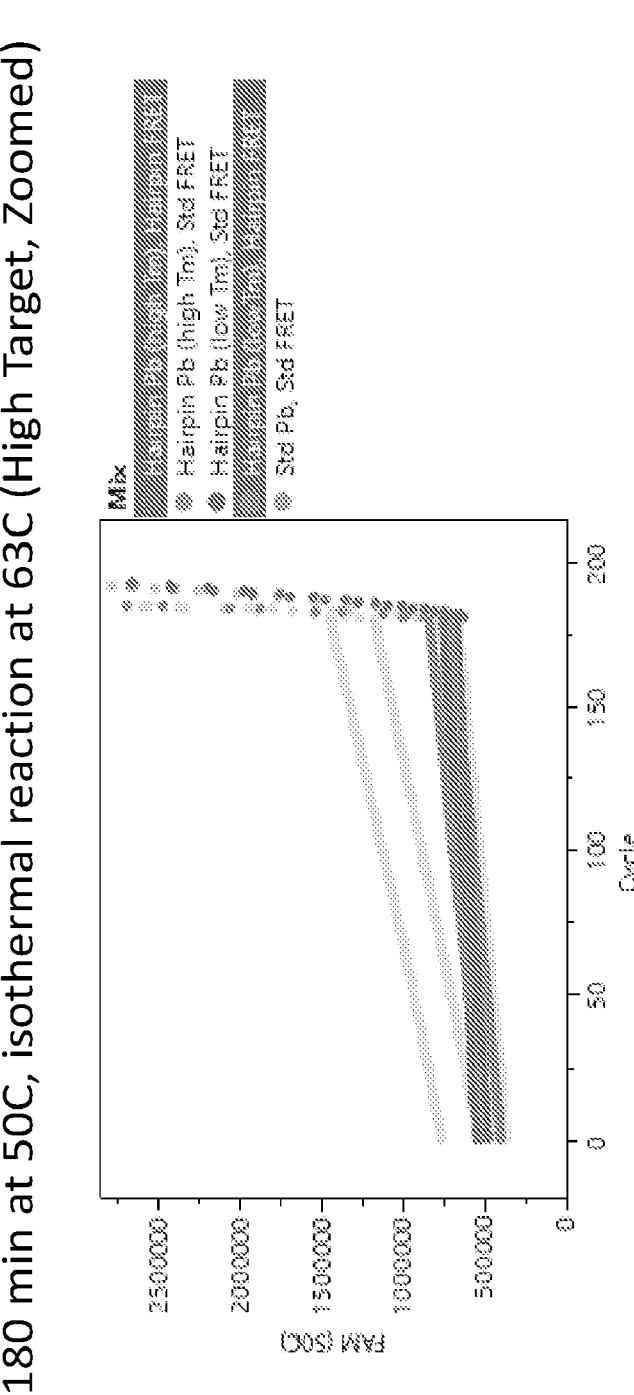
Figure 15D:
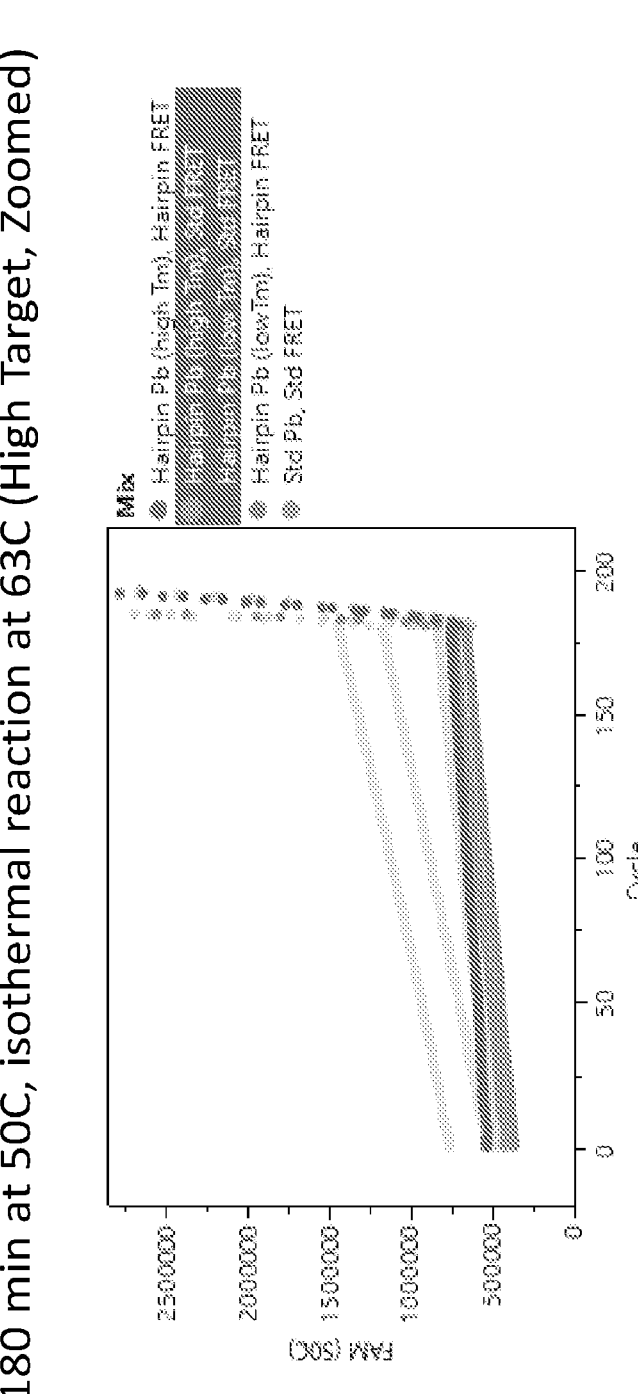
Figure 15E:
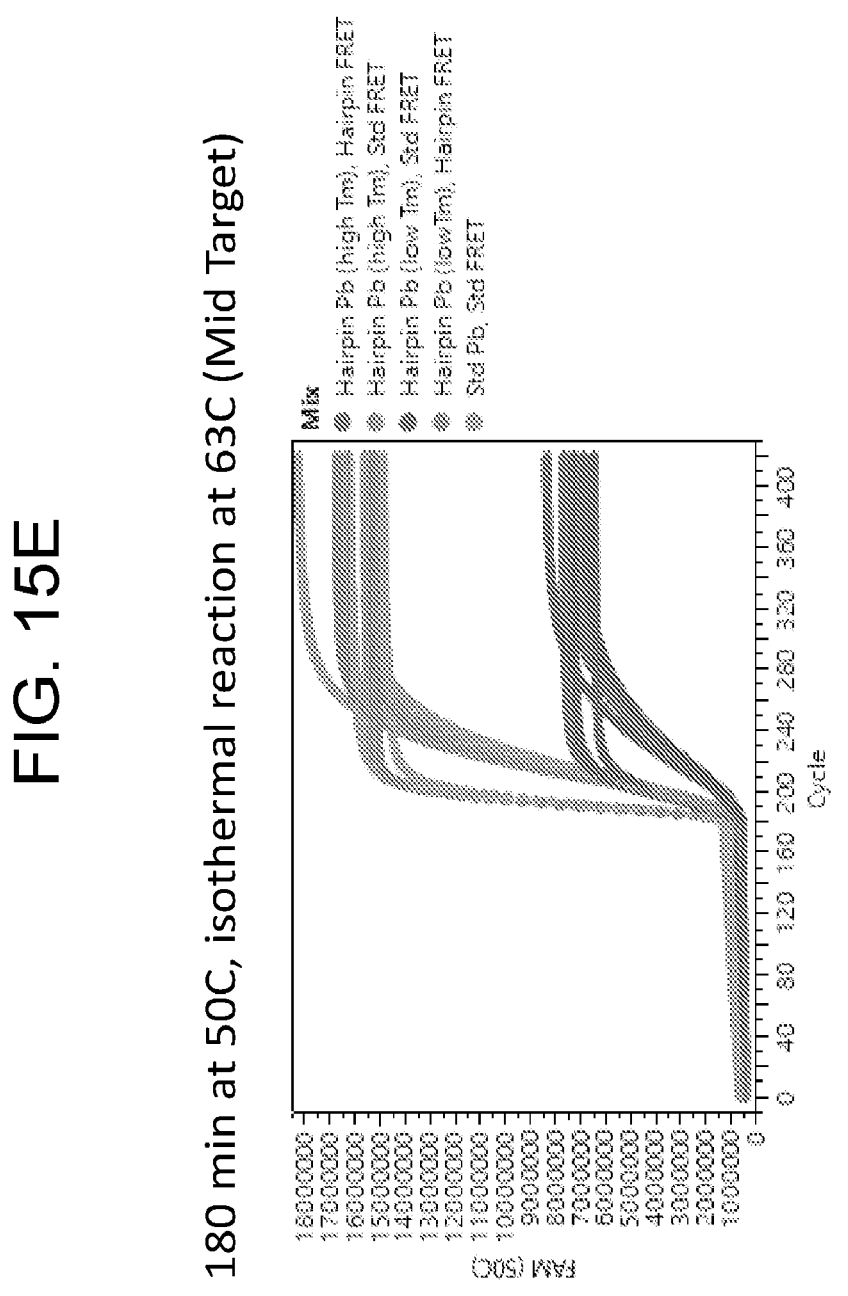
Figure 15F:
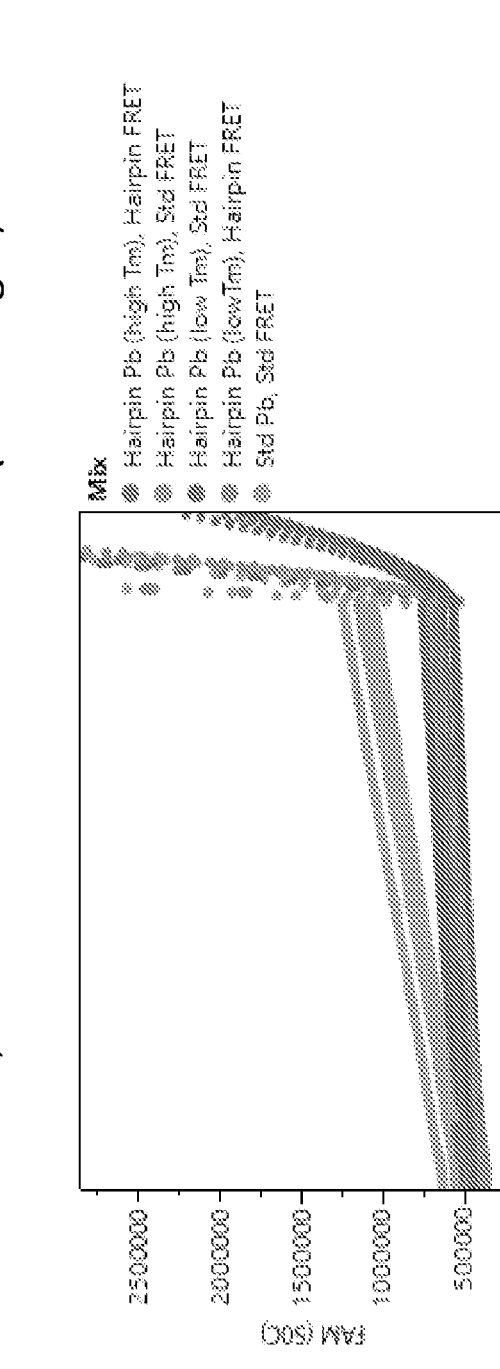
Figure 15G:
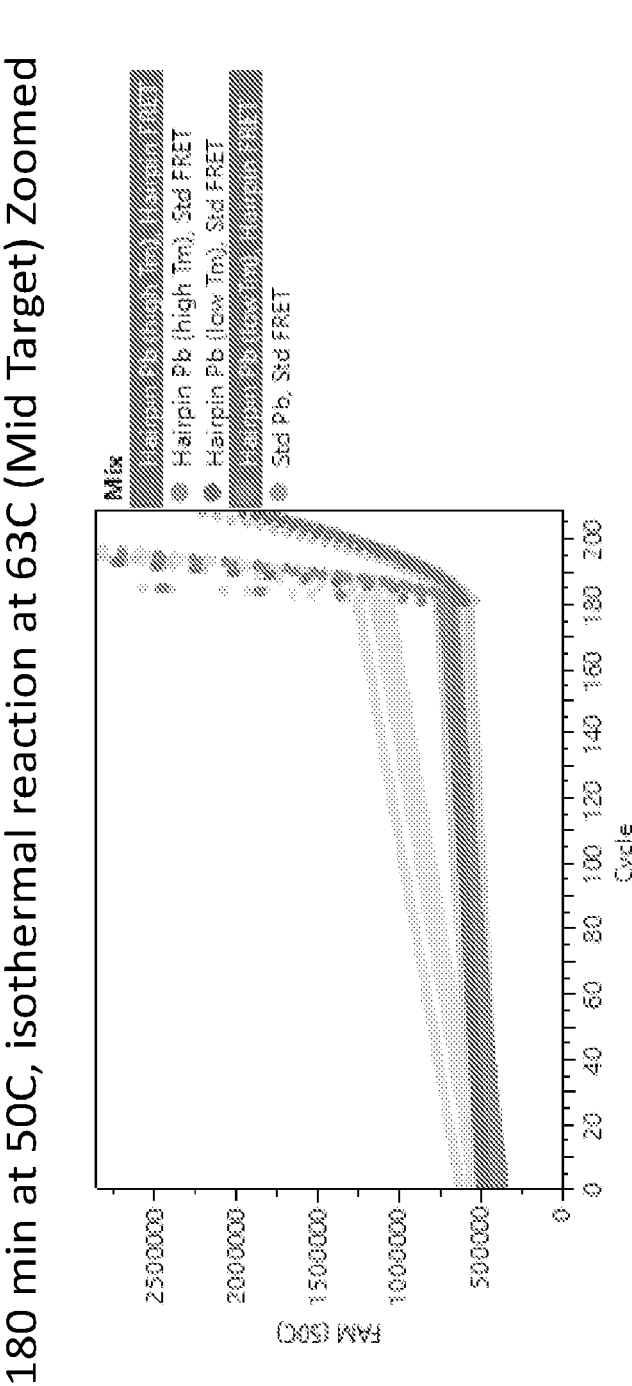
Figure 15H:
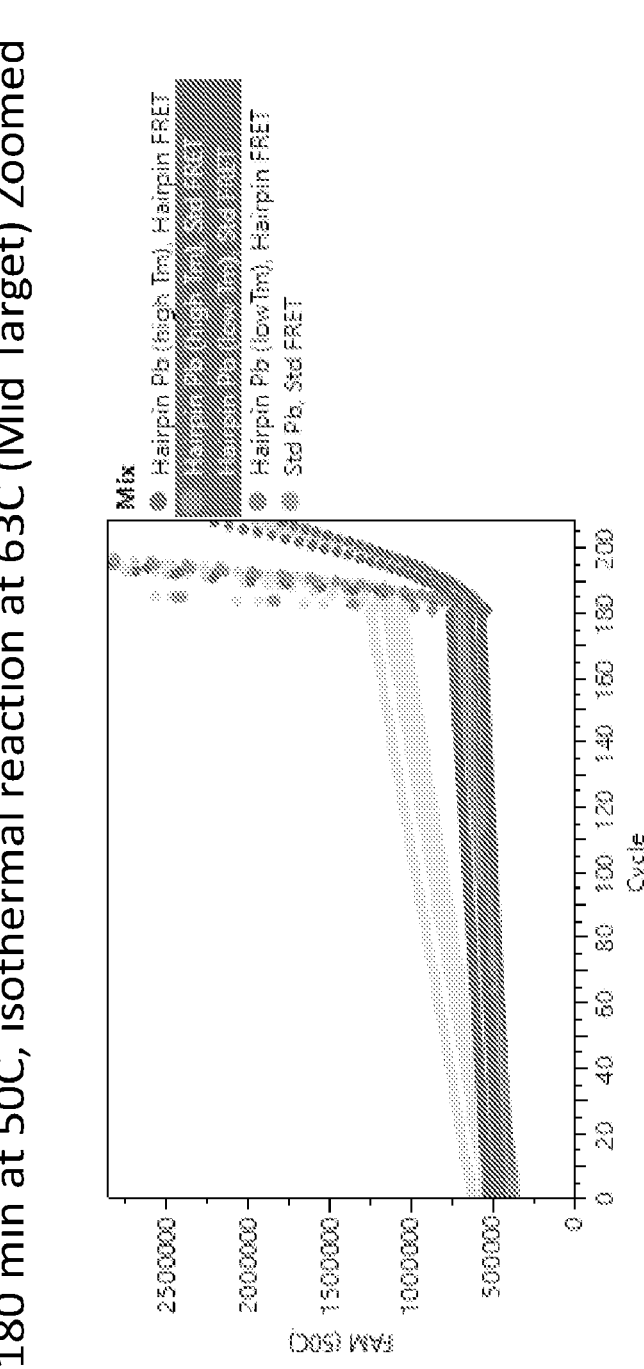
Figure 15I:
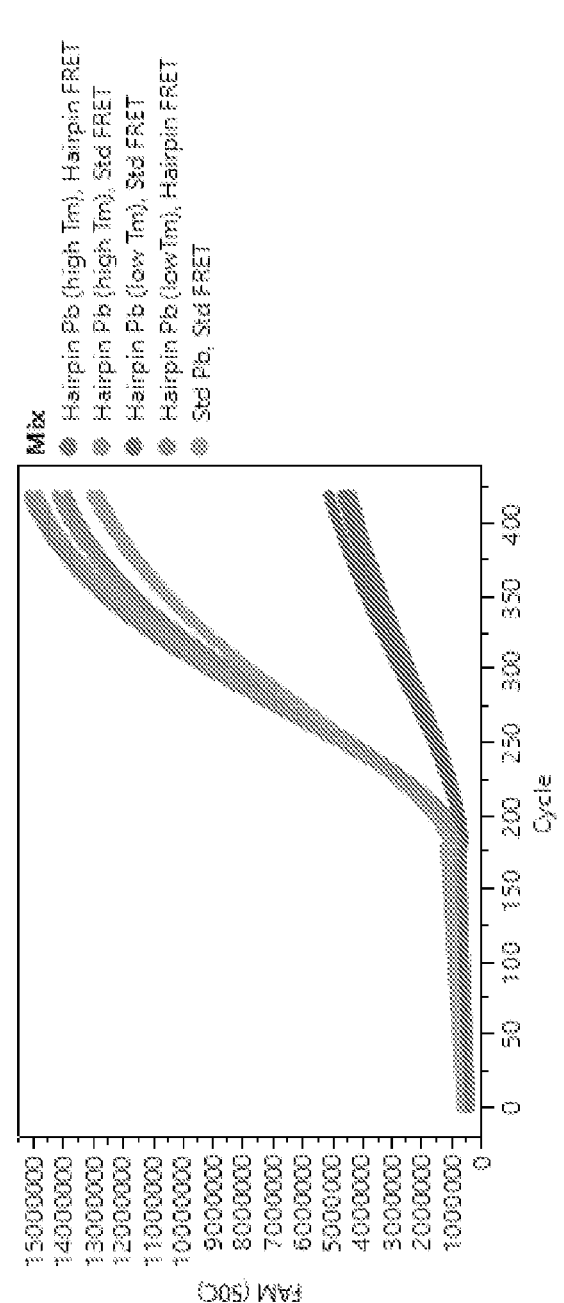
Figure 15J:
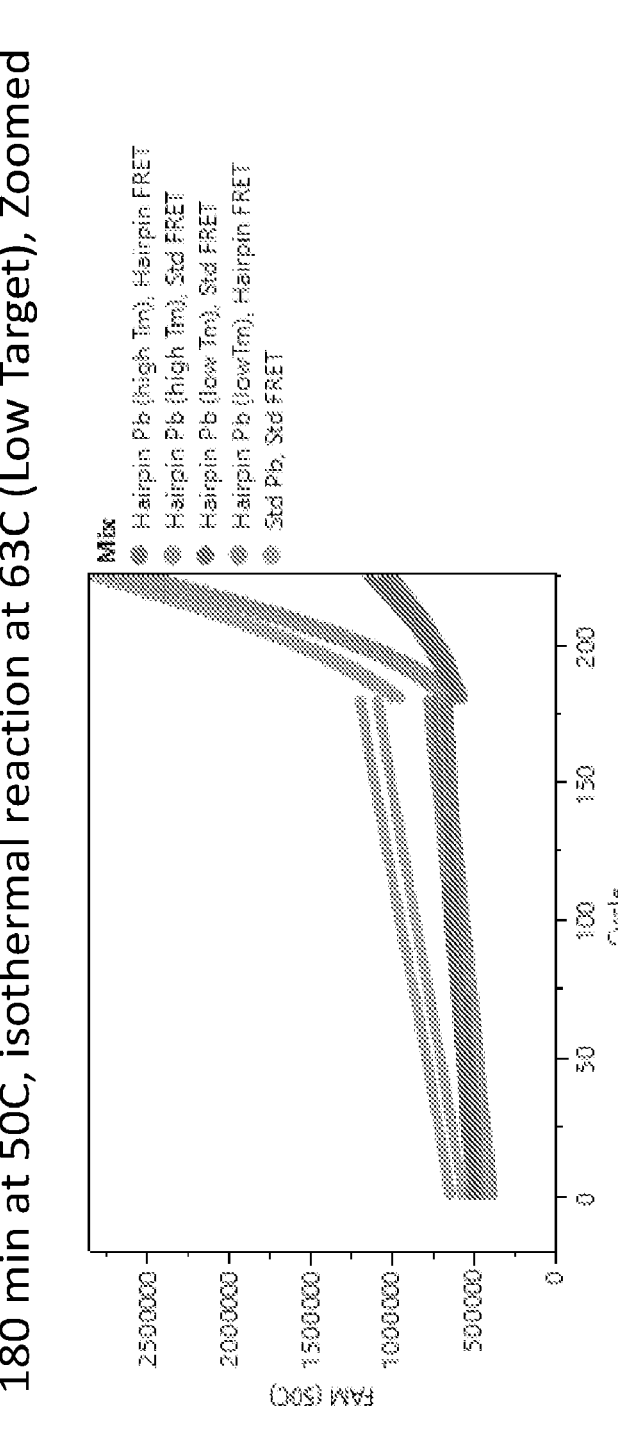
Figure 15K:
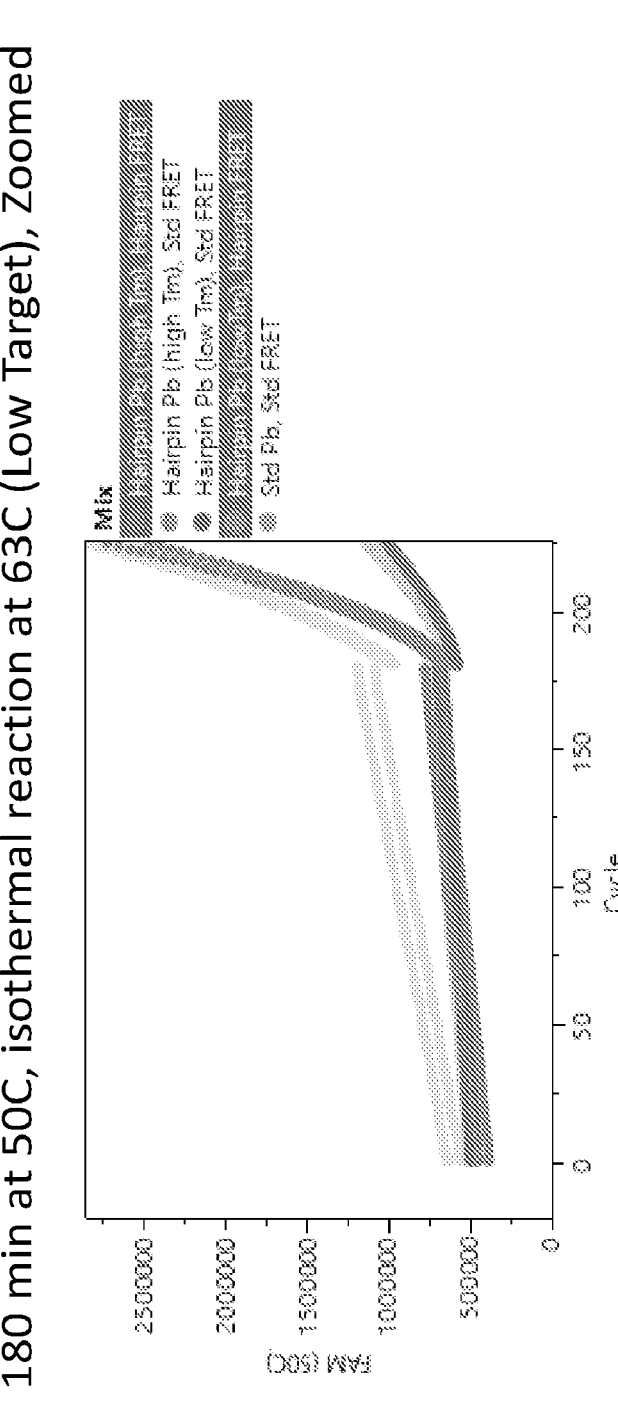
Figure 15L:
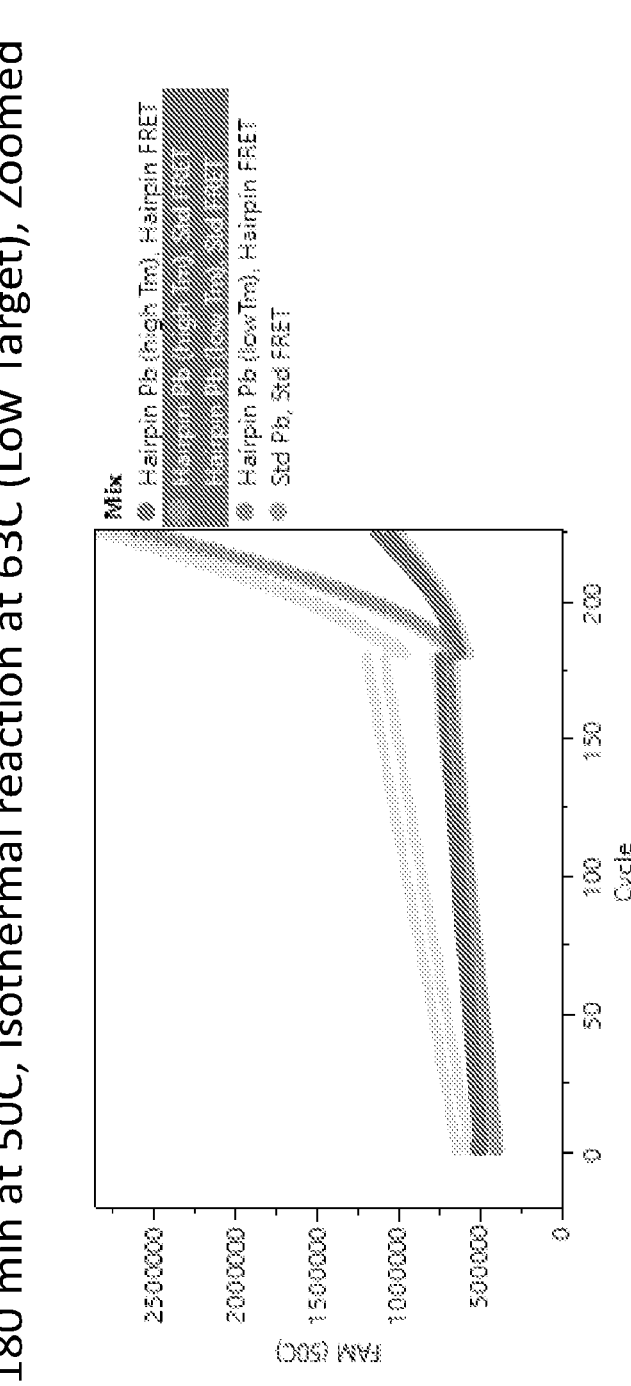
Figure 15M:
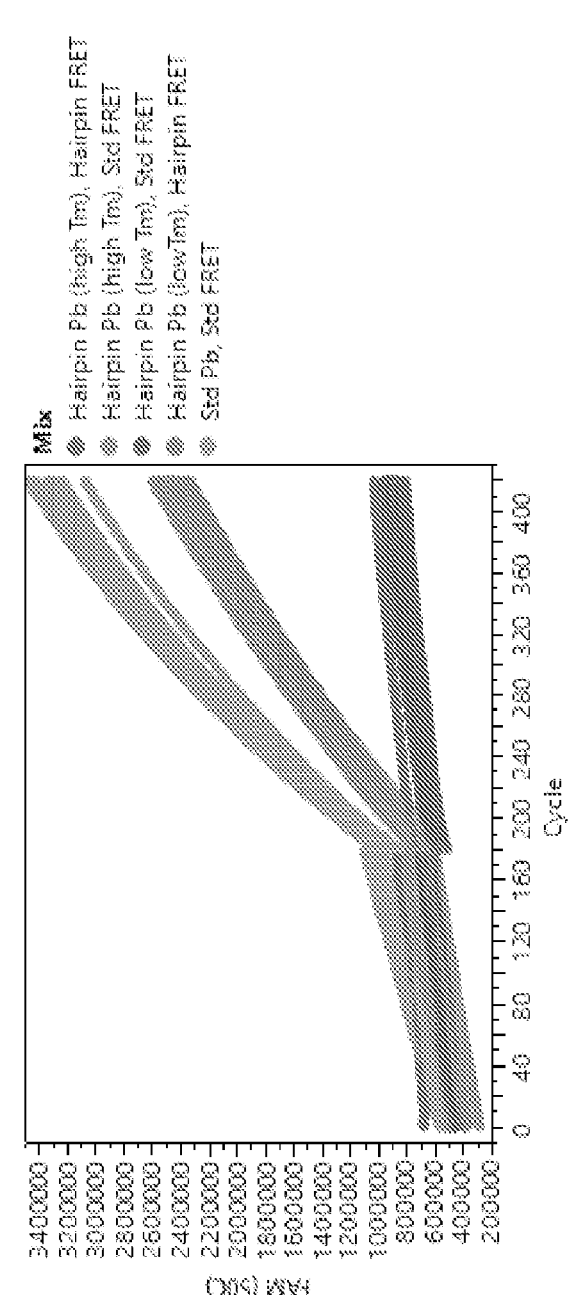
Figure 15N:
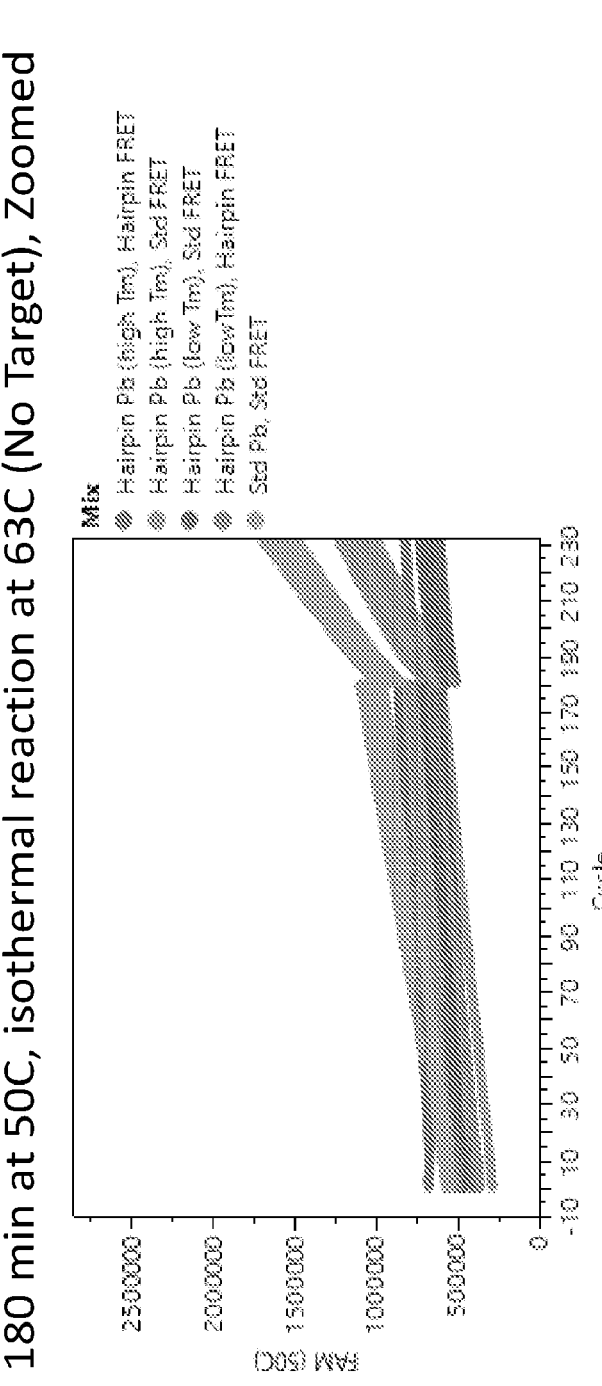
Figure 15O:
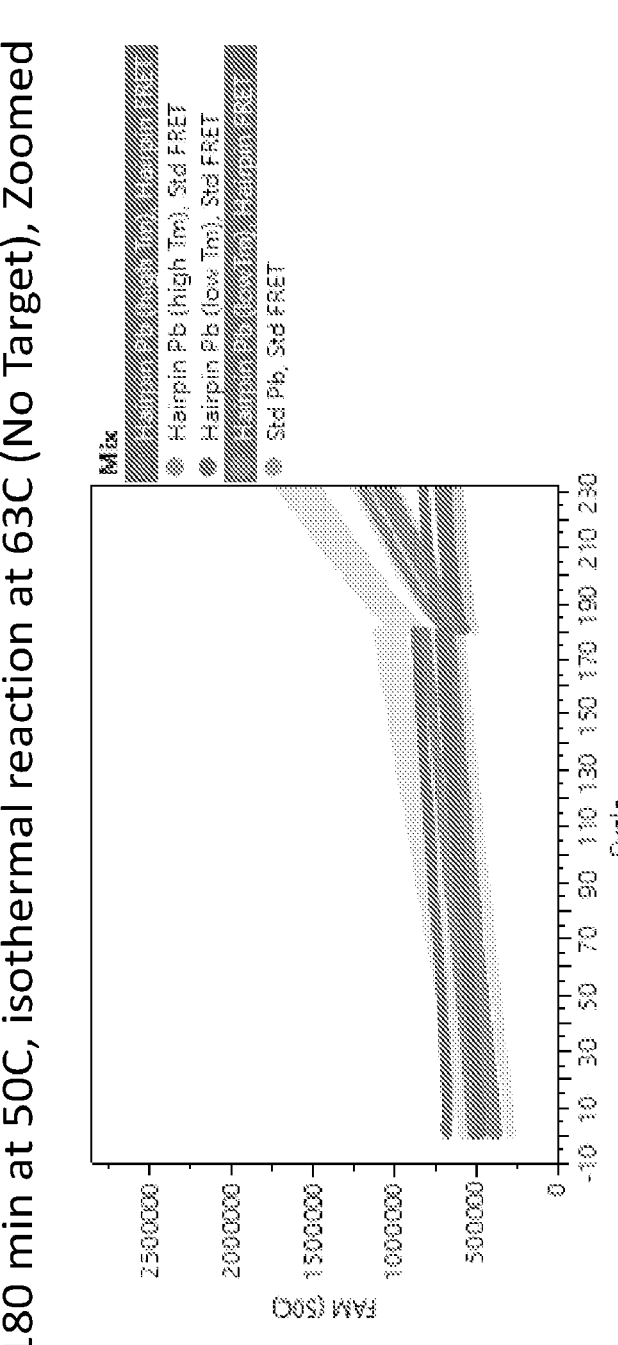
Figure 15P:
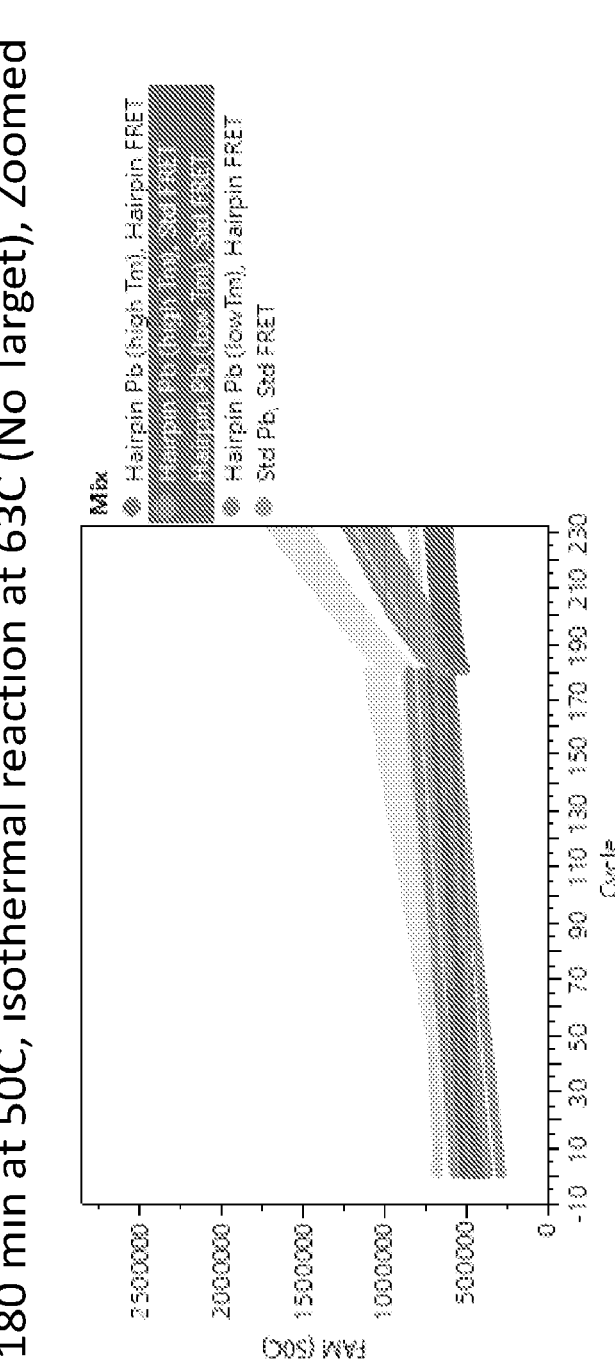

Amplification curves were assessed using MultiComponent Data. Linear fits (RFU/Cycle) were determined per well and compared across mixes. The results are shown in FIGS. 15A-15P, with the specification reaction configurations shown in each title bar. "Zoomed" figures are enlarged to show the transition between the 50° C. (repressed) incubations and the 63° C. (unrepressed) cleavage assay conditions. These data show that a 5' hairpin on the primary probe suppresses background and does not inhibit the assay when the reactions are shifted to the higher "unrepressed" temperature.

REFERENCES

1. Kaiser M, et al. J Biol Chem. 1999. Vol 274, No 30, 21387-21394.
2. Dorjsuren D, et al. Nucleic Acids Research. 2011. Vol 39, No 2 ell
3. Lyamichev V, et al. Biochemistry. 2000. 39, 9523-9532.
4. Tsutakawa S, et al. Cell. 2011. 145, 198-211.
5. Tumey N, et al. Bioorg & Med Chem Let. 2004. 15, 277-281.
6. Hall J G, et al. Proc Natl Acad Sci USA 2000; 97: 8272-8277. Sensitive detection of DNA polymorphisms by the serial invasive signal amplification reaction.

7. Allawi H T, et al. J of Clin Microbio 2006; vol 44, no. 9: 3443-3447. Invader Plus Method Detects Herpes Simplex Virus in Cerebrospinal Fluid and Simultaneously Differentiates Types 1 and 2.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

---

What is claimed is:

1. A composition comprising a 5' hairpin invasive cleavage structure having a target cleavage site and a FRET labeling system, wherein a first member of the FRET labeling system is attached at a first position on the 5' hairpin invasive cleavage structure and a second member of the FRET labeling system is attached at a second position on the 5' hairpin invasive cleavage structure, wherein the target cleavage site is between the first position and the second position;

wherein the 5' hairpin invasive cleavage structure comprises a 5' flap, a downstream duplex stem, and an upstream duplex stem that define an invasive cleavage structure, wherein the 5' flap comprises a hairpin-forming region configured to form a hairpin at a temperature below a 5' hairpin melting temperature, and wherein formation of a hairpin in the hairpin-forming region suppresses FEN-1 endonuclease cleavage of the 5' hairpin invasive cleavage structure at the target cleavage site.

2. The composition of claim 1, wherein the 5' hairpin-forming region of the 5' hairpin invasive cleavage structure is configured to form a hairpin structure at room temperature.

3. The composition of claim 1, further comprising a buffer solution comprising Mg$^{++}$.

4. The composition of claim 1, further comprising a thermostable flap endonuclease.

5. The composition of claim 4, wherein the flap endonuclease comprises a FEN-1 endonuclease from an Archaeal organism.

6. The composition of claim 1, further comprising one or more components selected from:
a DNA polymerase;
deoxynucleoside triphosphates; and
primers.

7. A method, comprising:

i) providing a 5' hairpin invasive cleavage structure having a target cleavage site and a FRET labeling system, wherein a first member of the FRET labeling system is attached at a first position on the 5' hairpin invasive cleavage structure and a second member of the FRET labeling system is attached at a second position on the 5' hairpin invasive cleavage structure, wherein the target cleavage site is between the first position and the second position;

wherein the 5' hairpin invasive cleavage structure comprises a 5' flap, a downstream duplex stem, and an upstream duplex stem that define an invasive cleavage structure, wherein the 5' flap comprises a hairpin-forming region, and wherein formation of a hairpin in the hairpin-forming region suppresses FEN-1 endonuclease cleavage of the 5' hairpin invasive cleavage structure at the target cleavage site;

ii) exposing the 5' hairpin invasive cleavage structure to a flap endonuclease in a reaction mixture; and iii) detecting the presence or absence of cleavage of the 5' hairpin invasive cleavage structure at the target cleavage site.

8. The method of claim 7, wherein the 5' hairpin-forming region of the 5' hairpin invasive cleavage structure is configured to form a hairpin structure at room temperature.

9. The method of claim 7, wherein the 5' hairpin invasive cleavage structure is exposed to the flap endonuclease at a temperature at which the 5' hairpin-forming region is not in the form of a hairpin.

10. The method of claim 7, wherein the reaction mixture comprises a buffer solution comprising Mg$^{++}$.

11. The method of claim 7, wherein the flap endonuclease comprises a thermostable flap endonuclease.

12. The method of claim 11, wherein the thermostable flap endonuclease comprises a FEN-1 endonuclease from an Archaeal organism.

* * * * *